(12) United States Patent
Steidler et al.

(10) Patent No.: US 8,759,088 B2
(45) Date of Patent: Jun. 24, 2014

(54) LACTOCOCCUS PROMOTERS AND USES THEREOF

(75) Inventors: Lothar Steidler, Drongen (BE); Klaas Vandenbroucke, Ghent (BE); Sabine Neirynck, Drongen (BE)

(73) Assignee: Actogenix N.V., Zwijnaade (BE)

( * ) Notice: Subject to any disclaimer, the term of this patent is extended or adjusted under 35 U.S.C. 154(b) by 862 days.

(21) Appl. No.: 12/522,527

(22) PCT Filed: Jan. 14, 2008

(86) PCT No.: PCT/EP2008/050352
§ 371 (c)(1),
(2), (4) Date: Jul. 8, 2009

(87) PCT Pub. No.: WO2008/084115
PCT Pub. Date: Jul. 17, 2008

(65) Prior Publication Data
US 2010/0080774 A1 Apr. 1, 2010

(30) Foreign Application Priority Data

Jan. 12, 2007 (EP) .................................. 07447001
Nov. 14, 2007 (EP) .................................. 07120653

(51) Int. Cl.
| | | |
|---|---|---|
| C12N 15/00 | (2006.01) | |
| C12P 21/06 | (2006.01) | |
| C12N 15/74 | (2006.01) | |
| C07H 21/04 | (2006.01) | |
| C12N 1/20 | (2006.01) | |
| A61K 31/70 | (2006.01) | |

(52) U.S. Cl.
USPC ............... 435/320.1; 435/252.9; 435/471; 435/69.1; 536/24.1

(58) Field of Classification Search
USPC ........... 435/320.1, 471, 69.1, 252.9; 536/24.1
See application file for complete search history.

(56) References Cited

U.S. PATENT DOCUMENTS

| | | | |
|---|---|---|---|
| 7,495,092 B2 * | 2/2009 | Barrangou et al. .......... | 536/24.1 |
| 8,021,653 B2 * | 9/2011 | Kano et al. .................. | 424/93.2 |
| 2002/0137140 A1* | 9/2002 | Vrang et al. ................. | 435/69.1 |
| 2008/0138859 A1 | 6/2008 | Park et al. | |
| 2008/0268502 A1 | 10/2008 | Haefner et al. | |

FOREIGN PATENT DOCUMENTS

| | | |
|---|---|---|
| RU | 2 051 175 | 12/1995 |
| WO | WO 01/02570 | 1/2001 |
| WO | WO 02/090551 | 11/2002 |
| WO | WO 2006/057289 * | 6/2006 |
| WO | WO 2006/065095 | 6/2006 |
| WO | WO 2006/069711 | 7/2006 |

OTHER PUBLICATIONS

Atwood, T.K. The Babel of Bioinformatics. Science 290:471-473, 2000.*
Gerhold et al. It's the genes! EST access to human genome content. BioEssays 18:973-981, 1996.*
Xie et al. Domains of the rat rDNA promoter must be aligned stereospecifically. Mol. Cell Biol. 12:1266-1275, 1992.*
Muller et al. Repression of lac promoter as a function of distance, phase and quality of an auxiliary lac operator. J. Mol. Biol. 257:21-29, 1996.*
Alam et al. Lung surfactant protein B promoter function is dependent on the helical phasing, orientation and combinatorial actions of cis-DNA elements. Gene 282:103-111, 2002.*
GenBank Accession No. AF320915.1. *Lactococcus lactis* strain MG1363 YfaA (YfaA) gene, partial cds; HIIA (hIIA) gene, complete cods; and YfbM (yfbM) gene, partial cds. pp. 1-2, 2001.*
Poquet et al. An export-specific reporter designed for Gram-positive bacteria: Application to *Lactococcus lactis*. J. Bacteriol. 180:1904-1912, 1998.*
Termont, et al. "Intracellular Accumulation of Trehalose Protects *Lactococcus lactis* from Freeze-Drying Damage and Bile Toxicity and Increases Gastric Acid Resistance," *Appl Environ Microbiol.*, vol. 72, No. 12, pp. 7694-7700, Dec. 2006.
Chatel, et al. "Induction of Mucosal Immune Response After Intranasal or Oral Inoculation of Mice with *Lactococcus lactis* Producing Bovine beta-lactoglobulin," *Clinical and Diagnostic Laboratory Immunology*, vol. 8, No. 3, pp. 545-551. May 2001.
Steidler, et al. "Therapeutic Drug Delivery by Genetically Modified *Lactococcus lactis*," *Annals of the New York Academy of Sciences.* vol. 1072. pp. 176-186, Aug. 1, 2006.
Waterfield, et al. "the Isolation of Lactococcal Promoters and Their Use in Investigating Bacterial Luciferase Synthesis in *Lactococcus lactis*," *Gene.* vol. 165, No. 1, pp. 9-15, Nov. 7, 1995.
Nucleotide, The National Center for Biotechnology Information, GenBank Accession No. CP000425 (online) (Feb. 11, 2006).

* cited by examiner

*Primary Examiner* — Quang Nguyen
(74) *Attorney, Agent, or Firm* — Knobbe, Martens, Olson & Bear LLP

(57) ABSTRACT

The invention is in the field of molecular biology, and relates to recombinant engineering and protein expression. More in particular, the invention relates to nucleic acids for recombinant expression of proteins comprising sequences derived from *Lactococcus* and useful as promoters. The invention further relates to vectors comprising the nucleic acids and host cells transformed therewith. The invention also covers the use of host cells comprising the nucleic acids or vectors for expressing heterologous or homologous proteins; and also for delivery, especially therapeutic delivery, of the said proteins to subjects.

31 Claims, 22 Drawing Sheets

FIGURE 1A

GATTTTGTAATTAATATTTGGAGAGGGATTTACTGACAAAAATTCTGTCAGTAAATCTCTAATCTCAAA
ATCGTCTAGCGTTAAATTTATTAGAAGTGGAGAAAGAATTG (SEQ ID NO: 1)

GTTCAGAAACTGCCTGATGGGCTAGATAAGCCTTGAAAATTTCTACAATAAATAGTATAATAGAAATAA
TGGTTTGTCAGCAAAATCTGTGGGATATATTGTCCCCATAGGCTTTGTAAGCAACGAAACACTACTGTT
TTCGTTGCTTTTTTGGCGTCTTTTATATTGAATAAATCAGAAAAGTTATTAAAAAGACAAACTACTGAA
TTTTCGGTTTTTTTAATTAAAAATTCATCAAAAACACAGACTTTTTTAATCAAATCTAAAAAATAGAGG
AGAAAACACTTGAAAAAAAGATTATCTCAGCTATTTTAATG (SEQ ID NO: 2)

GCTAGATAAGCCTTGAAAATTTCTACAATAAATAGTATAATAGAAATAATGGTTTGTCAGCAAAATCTG
TGGGATATATTGTCCCCATAGGCTTTGTAAGCAACGAAACACTACTGTTTTCGTTGCTTTTTGGCGTC
TTTTATATTGAATAAATCAGAAAAGTTATTAAAAAGACAAACTACTGAATTTTCGGTTTTTTTAATTAA
AAATTCATCAAAAACACAGACTTTTTTAATCAAATCTAAAAAATAGAGGAGAAAACACTTG (SEQ ID
NO: 157)

ACTAATCTATACGAAAATTGATTTTGAATGTAACTAAAAATGGAATTAAAAAGAAAATTGGTTTATAAT
ATATTTATAGAAAAGTTAATATTAAATCTCTTTATGACATTTAATATTTAAAAAATGGAGGTTAGTTAT
G (SEQ ID NO: 3)

CTAAGTTACTGCAAATCTGTTTCTAGTTAAGTGTTAAACGCATAATTAGGGCAGAGATATATAATTAAT
CATTATAGGAGAAAAACACAAAATG (SEQ ID NO: 4)

GTTCAGAAACTGCCTGATGGGATAAATTTCACTGACGCAAGCTTCTTTAATTTGTGGTAAAATAGATGT
GATTGTTAGAGTAGTAATTACTATTTAAAACCAATAAAGATTCATTTCTGATAAAAAAGAAGTGAAGAA
ATCAATGAGGAGAATTGGATTAAAATGAAAAAAAAGATTATCTCAGCTATTTTAATG (SEQ ID NO:
5)

AAATTAAGGATAGATTTTTTCTATCCTTTTTCATTATTATTCAAATGATAAAATTTCAAAATGTAAGCG
CAAAACCTTTTGAAGTTTAGGTTTGCGAAGATTTTCACTTGAAAAATCTTTCAAAAAATAGTAAAATCA
AAGATGTATTAAGAGTGCAGACGCACTTAAAAATAATAAGGAGACTAAAATG (SEQ ID NO: 6)

ATTTGGTTGACATAATTTGTCAAGCAAGTTTACAGCGAAAATTTAACTAGGAGAGTAAAGCATG (SEQ
ID NO: 7)

CAAATAAAAAGAACTGATGTGAGAAAATCTCACATTGAAGCTTGACTTTGCGAAAGACAAGGTCTATAA
TGATACGTATGGAGGCGAGATTTGGTGAAAGAACGTGAATTAAGACGCTCTATG (SEQ ID NO: 8)

FIGURE 1B

GTTCAGAAACTGCCTGATGGGATATTATCTTTATCCTCCTTATATATAATCTTTTTAAATAGTATTTTC
AGAATAACATAATAACCTGTAACAAGGTAGGTAATTAAGATGCCAATAAAAGCTCGTTATTAGTGCAGT
TTTTGAAACAATATAAAATGACTACCTAATAACTGTGATACTTATTTGAGTAAAATATTTTGAAGGGAA
ATTTACTGATGAAAGTGGTTAAGAAAAGTTACTTTAATTCATATTTATTAGTACTTATTGCACCATGTT
GAGTAACTATGATACAATAGATAAATATACTACTTCAAGGAGAAGATTATGAAAAAAAGATTATCTCA
GCTATTTTAATG (SEQ ID NO: 9)

GTTCAGAAACTGCCTGATGGGATATTATCTTTATCCTCCTTATATATAATCTTTTTAAATAGTATTTTC
AGAATAACATAATAACCTGTAACAAGGTAGGTAATTAAGATGCCAATAAAAGCTCGTTATTAGTGCAGT
TTTTGAAACAATATAAAATGACTACCTAATAACTGTGATACTTATTTGAGTAAAATATTTTGAAGGGAA
ATTTACTGATGAAAGTGGTTAAGAAAAGTTACTTTAATTCATATTTATTAGTACTTATTGCACCATGTT
GAGTAACTATGATACAATAGATAAATATACTACTTCAAGGAGAAGATTATG (SEQ ID NO: 158)

AAATGAATAGAAATTCTGTTGTTAGACAGAAAATAAAAACAGGAGGAAAAACATTG (SEQ ID NO: 10)

GTTGCTTAGCAAAGCTCAAAAAATCTGTCAGTAAAAATAAAATCAAGAATCTTGTAAAAGTAACCCTTT
ACAAGCTAAAAGTAAAATTCTCAAAGCCAAAATATCCGAATTTGTGATATAATTAACCTATCGATTTGA
ATTGAATCAGCATGGTGCTTTTTCAATCTCAACAAAATTATCTTATAAGGAGAATTTTTCCAAATG
(SEQ ID NO: 11)

GTTCAGAAACTGCCTGATGGGAATAAAAATTACTGTCAGCCTGCTCAGTAATTTTTTTAGTCATATTTT
TAGGTGGAAAGTCAAAGATTATTGCCAAAAGTATTAGCTTTTTTAATGTTAACCGCTTTCAGGAGAAGG
GGAGTTCATTTGCTTTTGTAGAGCGCTTTCTAAGGTAGTTTATGTTTGCAAATTTTAAAAAAAGTGTTA
AAATAAAAGAGTAAGTTAAATTGTTAACTTAGTCAATTTAAAAGGTTTGCCTTTTATAAAATCTAATCC
CTATAAGGAGGAAACTACTAATGAAAAAAAAGATTATCTCAGCTATTTTAATG (SEQ ID NO: 12)

AACCGCTTTCAGAAGAAGGGGAGTTCATTTGCTTTTGTAGAGCGCTTTCTAAGGTAGTTTATGTTTGCA
AATTTTAAAAAAAGTGTTAAAATAAAAGAGTAAGTTAAATTGTTAACTTAGTCAATTTAAAAGGTTTGC
CTTTTATAAAATCTAATCCCTATAAGGAGGAAACTACTAATG
(SEQ ID NO: 159)

AAATAAAAAATTATTGGCTAGTCTGTCAGTAATTTTTTATTGTATAAAATCATTAAAAATGCAAACGCT
TTTTATTTGTAATTGAAATAAAAAAATAACCAAGTGAATCATGGCTGAAAAACACAAAAGAAATTGTAA
TTGTGTTATAATTTAACCGTATTTCAAATTCAAGGAAGGTTTATTAAACATG (SEQ ID NO: 13)

TGTCAGTAATTTTTTATTGTATAAAATCATTAAAAATGCAAACGCTTTTTATTTGTAATTGAAATAAAA
AAATAACTAAGTGAATCATGGCTGAAAAACACAAAAGAAATTGTAATTGTGTTATAATTTAACCGTATT
TCAAATTCAAGGAAGGTTTATTAAACATG
(SEQ ID NO: 160)

FIGURE 1C

ATTGCTCATTTATAAATTTTGAAATTAAGAAGGATAAAAATATG (SEQ ID NO: 14)

GGAGAAAGGAATTGAGTTCGTCCTTCTAAACAGTCAGCAATAATCTGACATCAGAGATATCAGATTATT
GCTGTCCTTGAAGTCTAAGCACTAAAGTGCTAAGACCCTAAGGCGGGCTCACATCTTATAAATAATG
(SEQ ID NO: 15)

GGAGAAAGGAATTGAGTTCGTCCTTCTAAACAGTCAACGATAATCTGACATCAGATTATT
GCTGTCCCTGAAGTCTAAGCACTAAAGTGCTAAGACCCTAGGGCGGGCTCACATCTTATA
AATAATG (SEQ ID NO: 161)

TTAGTCACTCTTGTCACTAATCACTTTTCGCTTTAGAGGAGAACATACATG (SEQ ID NO: 16)

CTATCCTCTTTCTTTTCTTTTTATTCATAGTATTTATGAAAACCATTTTCATTTACAAATTATATCATG
AACTGTAAACCTTTTCAACCTTCAAGTGTGTTTTTTTACGTGATTTTTCAATAAAAATAGCGTAGAATG
GGTATATAATGTTTTTTATTTTCAGGAGAATTTAGAAAACTTATTTTCATTAATATTGGAGGAACCATT
TTG (SEQ ID NO: 17)

CTATCCTCTTTCTTTTCTTTTTATTCATAGTATTTATGAAAACCATTTTCATTTACAAATTATATCATG
AACTGTAAACCTTTTCAACCTTCAAGTGTGTTTTTTTACGTGATTTTTCAATAAAAATAGCGTAGAATG
GATATATAGTGTTTTTATTTTCAGGAGAATTTAGAAAACTTATTTTCATTAATATTGGAGGAACCATT
TTG (SEQ ID NO: 162)

GTTCAGAAACTGCCTGATGGGATAAGATTAATAGTTTTAGCTATTAATCTTTTTTTATTTTTATTTAAG
AATGGCTTAATAAAGCGGTTACTTTGGATTTTTGTGAGCTTGGACTAGAAAAAAACTTCACAAAATGCT
ATACTAGGTAGGTAAAAAAATATTCGGAGGAATTTTGAAATGAAAAAAAAGATTATCTCAGCTATTTTA
ATG (SEQ ID NO: 18)

GATAAGATTAATAGTTTTAGCTATTAATCTTTTTTTATTTTTATTTAAGAATGGCTTAATAAAGCGGTT
ACTTTGGATTTTTGTGAGCTTGGACTAGAAAAAAACTTCACAAAATGCTATACTAGGTAGGTAAAAAAA
TATTCGGAGGAATTTTGAAATG (SEQ ID NO: 163)

GCTTTTCTTGACAAAATAAGGATTTTTGGTATAATAGAAAAGTTGAATATAGCAGTCAGCTAGAAAGCT
CGTCAACATTTTGCTGTTATGTCAAGGAAGATAAGTCATTATGTTCCTTGTGTCAAGTAACTGAAGCTA
TAAGCGAAGGCAAAATGAACGAATTCGAGGCTGTCAATATTCTTCAAATAAAATATTTGGAGGACATAA
ATTATG (SEQ ID NO: 19)

AAATCAAATCATTTGGCAATGATTTCAAAAACGACTATAATGAGAATAGAATTAAAAAATAATCTAACT
GAATTCCATTCTCAATCTGGTCAAAATACCCAAGTATTAAGACTTCAAAATGGATTCACATCTTAAAAG
GAGAATTACTATG (SEQ ID NO: 20)

FIGURE 1D

GTTCAGAAACTGCCTGATGGCTCAAAATATAAGCTTAATCGCTTTTTAAAAAAGGATTGAAAGTAAAAA
ATAGATTGACAATCACTGTAAAAAATGATATTATATTAAACGGTACTTTTTACTTTGGACTCTCAGGAG
AACTTGTATAAGTTGCTAAACTTCTTGTCAGAACTTGGCTTAAGCGACCATATACTGACTAAAAAATTG
ATAAAAGAAATTGAGTTCGATTTCCCATATTCTAGGAAAATAGACAAATGTTTCCAAGGAACTTCGTTC
CTCTCCAACGTTTTCTAATTTTCTACGAATATAAACGGTCAATCTCACATCTTAAATCATCCAATAAAA
AGAAAGGAATGCTTTTGTATTTCTCATCGCTTCGCAGAAATGTGGAAAAATATAAAAAGCAGACAGTAA
AATGAAAAAAAAGATTATCTCAGCTATTTTAATG (SEQ ID NO: 21)

TCAAAATATAGGCTTAATCGCTTTTTAAAAAAGGATTGAAAGTAAAAAAGGAATGCCAGT
TCCTTTTTTACAACTATTCTAAAAAATAGATTGACAATCACTATAAAAATGATATTATA
TTAAACGGTACTTTTTACTTTGGACTCTCAGGAGAACTTGTATAAGTTGCTAAACTTCTT
GTCAGAACTTGGCTTAAGCGACCATATACTGACTAAAAAATTGATAAAAGAAATTGAGTT
CGATTTCCCATATTCTAGGAAAATAGACAAATGTTTCCAAGGAACTTCGTTCCTCTCCAA
CATTTTCTAATTTTCTACGAATATAAACGGTCAATCTCACATCTTAATCATCCAATAAAA
AGAAAGGAATGCTTTTGTATTTCTCATCGCTTCGCAGAAATGTGGAAAAATATAAAAAGC
AGACAGTAAAATG(SEQ ID NO: 164)

GCGTCGGGCTTGCGTCGCTAGCTTTTGCTTTATGTACGTCAGTACGATTCAGCACGGACTTCGTCCTAA
AAGCTGCCTAGCAATCCTTTAGCAAAAAATGTTATCCGTAATTGGTGGTTTGATTTAGGTCAAATTGCC
AGTATTTTGTCAATGCTAACTTTGTTAGACAGACAAAAACTCCCCGCTTGCTGATTATTTTATTAATCA
GTAAGAAAATCGATGGCAAAAACTATCGAAATTTAAAATAATATAGAGGTAGAATTGTG
(SEQ ID NO: 22)

TTTTTGCGTTGGGCTTGCGTCGTTAGCTTTTGCTTTACATACGTCAGTACGCTTCAGCAT
GGACTTCGTCCTAAAAGCTGCCTAGCAATCCTTTAGCAAAAAATGTTATCCGTAATTGGT
GGTTTGATTTAGGTCAAATTGCCAGTATTTTGTCAATGCTAACTTTGTTAGACAGACAAA
AACTCCCCGCTTGCTGATTATTTTATTAATCAGTAAGAAAATCGATGGCAAAAACTATCG
AAATTTAAAATAATATAGAGGTAGAATTGTG(SEQ ID NO: 165)

CTACAAACGCTTTACTGAAAACGCTATAAAGTCATTTTACCACTTTATAATAAAAATAAAAAAATATTT
CGCTAAAAAAATGATAGAATAGAATTAGAATTTAAAATAAAGGAGGAGATACGACAAGGCTGACTTTTA
TCGGCTGAGTTTTGTATCATATATTTTATG (SEQ ID NO: 23)

CTACAAACGCTTTACTGAAAACGCTATAAGGTCATTTTACCACTTTATAATAAAAAAAAA
AAATATTTCGCTTAAAAAATGATAGAATAGAATTAGAATTTAAAATAAAGGAGGAGATA
CTGACAAGGCTGACTTTTATCGGCTGAGTTTTGTATCATATATTTTATG (SEQ ID NO: 166)

FIGURE 1E

GTTCAGAAACTGCCTGATGGCAGCATTAAGATAAAGAGTTATGAGCTAAAAATAAGCACTTGTCAAACT
TCTGATAATCTGTTATACTTATTTAGTATGTTTTTGCATACTAATAAAACTGTTCATCCGCTGAGCTTA
ATTTGCTAAAAGCTGCTTATGATGGGCAAGAGGAGAAAAAAATGAAAAAAAAGATTATCTCAGCTATTT
TAATG (SEQ ID NO: 24)

CAGCATTAAGATAAAGAGTTATGAGCTAAAAATAAGCACTTGTCAAACTTCTGATAATCTGTTATACTT
ATTTAGTATGTTTTTGCATACTAATAAAACTGTTCATCCGCTGAGCTTAATTTGCTAAAAGCTGCTTAT
GATGGGCAAGAGGAGAAAAAAATG (SEQ ID NO: 167)

TAAATCATAAAACCTCTGTCAGAGGTTTTTTATTTTAAATATGAAAAATGAAAGATAAAATTTACTGAC
AGAAAAGTCAACAAGCTTAAAAATAAAAAGAAACACCCGAAAGCATTGCCATAGGTACTCTTATCAGAT
AATCTGAAAATAAAAATGTTGCATTTGTTGTTGAAAAATGCTAAAATACATAAGTCCGACTTTTTAGAT
ATATTTAAATTTGTATTTATATCTTTCGGGAAATTTTTAAGGAGGTACTTTTGCTTG
(SEQ ID NO: 25)

TAAATCATAAAACCTCTGTCAGAGGTTTTTTATTTTAAATATGAAAAATGAAAGATAAAA
TTTACTGACAGAAAAGTCAACAAGCTTAAAAATAAAAAGAAACACCCGAAAGCATTGCCA
TAGGTACTCTTATCAGATAATCTGAAAATAAAAATGGACTCAGGCTAGAAAAATAAAGGC
TTTTATGAAAGAAAGACTTGCATTTGTTGTTGAAAAATGCTAAAATACATAAGTCCGACT
TTTTAGATATATTTAAATTTGTATTTATATCTTTCGGGAAATTTTTAAGGAGGTACTTTT
GCTTG (SEQ ID NO: 168)

GTTCAGAAACTGCCTGATGGAATAGAAGATATTTTTCAGTAGATATAGATTAATAAAAGATAAATAGAT
TTCAAAGTAAGTTTATCCTTGCATTTCTAAAAAAACTTTGATATACTTATTTACGGTTCTAAAAGAACT
GACCGAAGACAGTAGGGGACGAAAGTCATAAACTTCCTACCGAGGACAAATATCAAAATGATAATTGAA
CTCTCTATGTCTTTTGTGTGTAGAGATTTTTTGTTTCTACAACCAAAATAAAATGGAGGTAAAAAAATG
AAAAAAAAGATTATCTCAGCTATTTTAATG (SEQ ID NO: 26)

TTTTTCAGTAGATATAGATTAATAAAAGATAAATAGATTTCAAAGTAAGTTTATCCTTGCATTTCTAAA
AAAACTTTGATATACTTATTTATGGTTCTAAAAGAACTGACCGAAGACAGTAGGGGACGAAAGTCATAA
ACTTCCTACCGAGGACAAATATCAAAATGATAATTGAACTCTCTATGTCTTTTGTGTGTAGAGATTTTT
TGTTTCTACAACCAAAATAAAATGGAGGTAAAAAAATG (SEQ ID NO: 169)

AAGAAGAATCAGCTGCTTAATTATAAGCAACATCACTTATATCGGCGGATTTACGCAACAAACTAAAAA
ATTAATAGGAGAATATTAAAATGGCATTGAACATTGAAAACATCGTTGCTGAA (SEQ ID NO: 27)

TTATAAGCAACATCACTTATATCGGCGGATTTACGCAACAAACTAAAAAATTAATAGGAG
AATATTAAAATG (SEQ ID NO: 170)

AAAACGCCTTAAAATGGCATTTTGACTTGCAAACTGGGCTAAGATTTGCTAAAATGAAAAATGCCTATG
TTTAAGGTAAAAAACAAATGGAGGACATTTCTAAAATG (SEQ ID NO: 28)

FIGURE 1F

CAAAAGCTTGATTTTTTTATTTGAAAAATGTTATAATCAACAAGTATGTTGTTTTTAAGCACATAAAAA
TTCTAATGGGAGGTAAATATAATG (SEQ ID NO: 29)

GTTCAGAAACTGCCTGATGGTAAATTTGTTCCAAATGAAGAAACAAATATTTCAAAATCCTACTATTTG
ATAGTAGGATTTTTAATATATTAGTCCAAAAGCTCAAAAAGGCTGATTTAAAGCAGATGAGTAGACTTT
TCAATTATTTTGTAAAGCACTTTCAAAAAAATAGATAACGCTTGCATTATGAAAATGAAAACGTTATAA
TTATTTTTATAAAGAACGTTAAATTATAAAACGTTAAGAATAAGGAGAAATAATTATGAAAAAAAAGAT
TATCTCAGCTATTTTAATG (SEQ ID NO: 30)

TAAATTTGTTCCAAATGAAGAAACAAATATTTCAAAATCCTACTATTTGATAGTAGGATTTTTAATATA
TTAGTCCAAAAGCTCAAAAAGGCTGATTTAAAGCAGATGAGTAGACTTTTCAATTATTTTGTAAAGCAC
TTTCAAAAAATAGATAACGCTTGCATTATGAAAATGAAAACGTTATAATTATTTTTATAAAGAACGTTA
AATTATAAAACGTTAAGAATAAGGAGAAATAATTATG   (SEQ ID NO: 171)

TCAGGATAGAAAAATTTTCTTCCTTTGTTAAAAACTTAGTGGAGAATTTTTCAAACTCAAAATGTTAAA
CTTTTGAAAACATGCAAAGGTAATTTTAAAACTTGCTTATTCATGCTCAAAAAGTATAACTGCAGTTTA
AAGCTAAATAGCCTTGAACTAGTAAAAATTTCTAGAAGGGAGCATATTTTTG (SEQ ID NO: 31)

TCAGGATAGAAAAATTTTCTTCCTTTGTTAAAAACTTAGTGGAGAATTTTTCAAACTCAAACTGTTAAA
CTTTTGAAAACATGCAAAGGTAATTTTAAAACTTGCTTATTCATGCTCAAAAAGTATAACTGCAGTTTA
AAGCTAAATAGCCTTGAACTAGTAAAAAATTTCTAGAAGGGAGCATATTTTG
(SEQ ID NO: 172)

TAAATGATAAAAGTTGCTGACAGAGTTGTCAGTGACTTTTTTTGATGCTGTCAGCAAAAAGAAAAGATA
ATTTTAAATTTATGAATAAGAGTGTGGTTTAATTGCTAGCCTGTCAGTAATTTGTGCAAACTGCCCAAA
AGATTTAGGCACTTATCTTATTGTTTTAGAAAACGTTTACAGTAGAATATAAACAAAGAACAAAAGTT
ACTAGAGGAGAAATAATG (SEQ ID NO: 32)

ATGATAAAAGTTGCTGACAGAGTTGCCAGTGACTTTTTTTGATTCTGTCAGCAAAAAGAA
AAGATAATTTTAAAATTGTGAATAAGCGTGTGGTTTAATTGCTAGCCTGTCAGTAATTTG
TGCAAACTGCCCAAAAGATTTAGGCACTTATCTTATTGTTTTAGAAAACGTTTACAGTA
GAATATAAACAAAGAACAAAAGTTACTAGAGGAGAAATAATG   (SEQ ID NO: 173)

CTTATTTCACAAGCATAACCTTAGGAAATTTCTCCAAAAAATGATAAATTTCTAATTATAGACACATAA
AAAAGAAAGGGAATCTATTATG (SEQ ID NO: 33)

CTTATTTCACAAGCATAACCTTAGGAAATTTCTCCAAAAAATGATAAATTTCTAATTATAGACACATAA
AATAGAAAGGGAATCTATTATG (SEQ ID NO: 174)

FIGURE 1G

TTTAATAAAAAACTGAAAAAATCACAGCTAAACTCTTGTTTTACTGTGATTTTATGTTAAAATAATTAA
TGAGTGTAATTGTATATAAAATTATCTGTACACTTAACTAATTTATTAAAAAAAAATATGAATCGTGAT
GTGTGAGGGAAAGGAGTCGCTTTTATG (SEQ ID NO: 34)

TTTAATAAAAAACTGAAAAAATCACAGGTAAACTCTTGTTTTACTGTGATTTTATGTTAA
AATAATTAATGAGTGTAATTGTATATAAAATTATCTGTACACTTACCTAATTTATTGAAA
AAAATATGAATCGTGATGTGTGAGGGAAAGGAGTCGCTTTTATG (SEQ ID NO: 175)

ACTAATTTAATTACCAGTAAAAATCACTTGTTATTAAGTTAAAGGTTGAGTTTCAAAAGATGAAAGTTA
GGAAAAATTG (SEQ ID NO: 35)

ATGGAAATTTTAACATATTTCTTGGTATAATTATAGTGTAAATCATCAAAAGAATTACTGACAGATTTG
TCAGTAAATTTTTCAGTATCCCGGAGGAGAAAAATG (SEQ ID NO: 36)

AATTCGCTCACTTACCGCACGAAGCAATTTTAAACTATCAACGTTTTTAGATTACAACACTTAATCATT
TCCTTTTGTAAGGAATTTAATAGGTTAATTTTTACTGACAGTTCTGTCAGTAAATTTTCGTACGTCAAA
TCTACTTAGAAAGGAACTGAATTCAGTGAGTAATTTACTTGCTGAATCGTATTTAATCTTATG  (SEQ
ID NO: 37)

AATTCGCTCACTTACCGCACGAAGTAATTTTAAACTATCAACGTTTTTAGATTACAACAC
TTAATCATTTCCTTTTGTAAGGAATTTAATAGGTTAATTTTTACTGACAGTTCTGTCAGT
AAATTTTCGTACGTCAAATCTACTTAGAAAGGAACTGAATTCAGTGAGTAATTTACTTGC
TGAATCGTATTTAATCTTATG(SEQ ID NO: 176)

ATTTCTCTCCTCACAAACTATTTTATTTACTATAATTATTTTATCACAAAAAAAGCGTTTTCAGCAAAA
ATATTAATTTTATTCTTAGAAAAAAATGCAAAATCTCCCTTAAGGGGATTATATTGGCAAAAATATTA
GTTAAATTTGTCAGATAACATTGAGATATAAAAAACAGAATAAAAAGAAAGTGGAGTAGGATAGCTTTC
ACTTACTCATATTGATAAAAGAAATAAATGAATAGATGCTTGCAAAAGTAGCTTAAACAATGTATAATG
AGAGAGTTGCTATGCAACCATCTCGCATTTCGTCTCGACAAAGTCGTAGTGTACGCAAGTATTGCGGCT
GCGGATGACAGATGAAAGAGGAAAAACTATTTTAAAAGGAGACATTAATATGT (SEQ ID NO: 38)

TTCTCTCCTCACAAACTATTTTATTTACTATAATTATTTTATCACAAAAAAAGCGTTTTC
AGCAAAAATATTAATTTTATTCTTAGAAAAAAATGTAAAAATCTCCCTTATGGGGATTAT
ATAGGCAAAAATATTCGTTAAATTTGTCAGACAACATTGAGATATAAAAAACAGAATAAA
AAGAAAGGGGAGTAGGATAGCTTTCATTTACTCATATTGATAAAAGAAATAAATGAATAG
ATGCTTGCAAAAGTAGCTTAAACAATGTATAATGAGAGAGTTGCTATGCAACCATCTCGC
ATTTCGTCTCGACAAAGTCGTAGTGTACGCAAGTATTGCGGCTGCGGATGACAGATGAAA
GAGGAAAAACTATTTTAAAAGGAGACATTAACATG (SEQ ID NO: 177)

FIGURE 1H

GTTGTGTATCTGCCATTTTATTCTCCTTTCGTATTTTTATTTTATTATAATCATTTTATCATTTAATTA
TCATTTTACTAAATGATATGATGCATTTTGAAGATAATAAAATGCTAGTAATAAGAGCTGGCCTAATAT
TCTAAAATTGTAATATATATATATCTAAATAATAAAATTAATCTTAAAAGTCATCTAAAACAATCAGTC
AAAAGTTGATAAAGAATTAGGGCTTGACAAGTTCTAAAATAATTGATAGAATAATAGAGTTGAAAAGCA
GAAGCACCCGCTTCTCGCCTTAGAGGTTATAGCCCTGGGCAAACAAATG (SEQ ID NO: 39)

TATTTTTATTTTATTATAATCATTTCATCATTTAATTATCATTTTGCTAAATGATATGAT
GCATTTTGAAGATAATAAAATGCTAGTAATAAGAGCTGGCCTAATATTCTAAAATTGTAT
TATATATATCTAAATAATAAAATTAATCTTAAAAGTCATCTAAAACAATCAGTCAAAAGT
TGATAAAGAATTAGGGCTTGACAAGTTCTAAAATAATTGATAGAATAATAGAGTTGAAAA
GCAGAAGCACCCGCTTCTCGCCTTAGAGGTTATAGCCCTGGGCAAACAAATG (SEQ ID NO: 178)

TTAAGAAAGGTAATTCTCATGTCAAAAGGAATCTTAGGGAAAAAAGTGGGAATGACTCAAATCTTCACA
GACAACGGTGAATTAATTCCTGTTACTGTGATCGAAGCGACTCCAAACACAGTTCTTCAAGTTAAATCT
GTCGAAACAGACGGTTACGAAGCAACTCAAGTTGGTTTCGATACACTTCGTGAAGTTTTGACCAACAAA
CCTGCCAAAGGTCATGCTGCTAAAGCTAATACGACTCCTAAGCGCTTCGTTCGTGAATTCAAAGGACTC
GAAGGCGCTGAAGTAGGAGCAGAAATCACTGTTGATACATTTGCAGCCGGAGATGTTGTTGATGTTACC
GGAACTTCTAAAGGTAAAGGTTTCCAAGGCCCAATCAAAACGTCATGGTCAATCACGTGGTCCTATGGC
CCACGGTTCACGTTACCACCGTCGTCCTGGTTCAATGGGTCCTGTTGCAGCTAACAAAGTTCCAAAAGG
TAAAAAACTTGCTGGACGTATGGGTAACAAACGCGTTACTGTACAAAACCTTGTTATTGCACAAGTGCT
TCCTGAAAAGAACGTTATCCTTGTAAAAGGTAATGTCCCAGGTGCTAAGAAATCATTGATTGTTGTTAA
ATCAGCAATCAAAGCTAAATAAGAAGGAAAGGAGATAGAAATCTATAATG (SEQ ID NO: 40)

AAATCCTCCTATATAAATAGTTTATAAAACCTTTAATCAAATTATATCAAAAAGTTTAAA
GATGACAAAGTGTGGGTTCTTGTCTTTTTCAGTAAATTCATTGATTTTATTTAAAATTTT
AAAAGATATACAAAAAGAACAGGAAAGAATGAAAAAAAGTCTAAAAAGTCCTTGACAAGG
CACATCTCCTTTGATAGAATAGACAAGTGCTGTTAAAAACAGTATGTAGCGATGAAACGA
GAGGTTGCGACACACCCGAAGGTATTGCCATACCTAACGTGTCGGTTTTCCCGTGGAGCT
AGCCTATTGAATACAATAGACGAGAGGAGAAAAAATGGCAACTAAAAAAATTCGCATTCG
CTTGAAAGCATACGAACATCGTATCCTTGACGCAGCTGCAGAAAAAATCGTAGAAACTGC
TAAACGTACAAACGCAGAAGTAAGTGGTCCAATTCCACTTCCAACTGACCGTAGCGTCTA
CACTGTTATCCGCGCGACTCACAAATATAAAGACTCACGCGAACAATTCGAAATGCGTAC
ACACAAACGCTTGATCGACATCATCGAACCAACACAAAAAACTGTTGATTCACTTATGAA
ACTCGATTTGCCAAGTGGTGTAAACATCGAAATTAAACTCTAATTAAGAAAGGTAATTCTCATGTCAAA
AGGAATCTTAGGGAAAAAAGTGGGAATGACTCAAATCTTCACAGACAACGGTGAATTAATTCCTGTTAC
TGTGATCGAAGCGACTCCAAACACAGTTCTTCAAGTTAAATCTGTCGAAACAGACGGTTACGAAGCAAC
TCAAGTTGGTTTCGATACACTTCGTGAAGTTTTGACCAACAAACCTGCCAAAGGTCATGCTGCTAAAGC
TAATACGACTCCTAAGCGCTTCGTTCGTGAATTCAAAGGACTCGAAGGCGCTGAAGTAGGAGCAGAAAT
CACTGTTGATACATTTGCAGCCGGAGATGTTGTTGATGTTACCGGAACTTCTAAAGGTAAAGGTTTCCA
AGGCCCAATCAAACGTCATGGTCAATCACGTGGTCCTATGGCCCACGGTTCACGTTACCACCGTCGTCC
TGGTTCAATGGGTCCTGTTGCAGCTAACAAAGTTCCAAAAGGTAAAAAACTTGCTGGACGTATGGGTAA
CAAACGCGTTACTGTACAAAACCTTGTTATTGCACAAGTGCTTCCTGAAAAGAACGTTATCCTTGTAAA
AGGTAATGTCCCAGGTGCTAAGAAATCATTGATTGTTGTTAAATCAGCAATCAAAGCTAAATAAGAAGG
AAAGGAGATAGAAATCTATAATG (SEQ ID NO: 179)

FIGURE 1I

GACTGATTTCTTGAGGTAAAATGGAGTCAAATACTGACCATTGATAAATCCAGAAATATATTCTATAAT
AATCACTGTTAAGAAATTAAAAGGGAAAATTTAAAAATG (SEQ ID NO: 41)

AGTATGATTGATTTTGATTTAACTAAAAAGAAAAGTTTATAATAAAAGGAAAGAAATAAAATG
(SEQ ID NO: 42)

AACACATAAAAGTGAGGCATCAGCCTCACTTTTATGAATATTTTCTTTTTATTTGTAAAAGTTTAAAAG
AACGGTTACAATTATAAAAGAAAAATTTAATTATTGAGCGAGAGCTAATCATAAGGAGAACAAATTTG
(SEQ ID NO: 43)

GCCATAATTATAACAAATTTGAAAGCGTTAAGAAAGTTTAAACTCTTTTTTTAATAATTTTAGTAAAAG
TTGCTAAAAAAAAACAATTTTCTTTGACCTTTTTTGACCAATGAGTTATAATATAGAAAAATAAACAAT
TGAACTTAATTTATTCCTAAATTGAGTCCATATCTTATTTATAAAGGAGATTCATTCTATG
(SEQ ID NO: 44)

ATAAAATAACAATCCTATCTTTACTGATAGGATTTTTTCCTTAAAAAATCCGTCAGTAATTTAAAAAC
TTGTAAATTTTATCTCACCAATTCAAAAGATAACTTTAGAATTGTAAAATGCAGGACAAACGAGGAAAT
GGCTTGTAATTCCAATCGAAAAATAGTAAAATAATAGGAGTCTGTTAATAGACAAATAAATATATTGAA
GTATCGGCGAGTTTAATTTTCACGTTCCTTACATGAAAATTAGGCGACAGCAAGGTACAAAATAAGGAG
AAAAAAATG (SEQ ID NO: 45)

GAGTGCTCTTTTTTGGATATAATACTCGGGTATGTGAATTTTCACATATAAGGCGTGGAAGCTGTAAAA
TACAGCATCATACCACATCACGAAAACAAAATATAAGGAGAATTTATCGTG (SEQ ID NO: 46)

TTGTAAAGAAAAATGTTGACAGAGTGCGGAACTTCTGCTATACTAATTAAGTTCGGTCTTTTTATGAAA
AAGACCTCATTAATTTGAAAGTGGGATTTGAACAAGCCCAAACTACAAATAAGGAGAAATTACACTATG
(SEQ ID NO: 47)

AAAAGAAGTAGTATAATAATATAGTTGTCTTTGTGAAATCTCATAAAGTGCAACCGCACGAAGTTTCGT
AATAAGTGGCGTAAGCCCACGAACAAAGGCGAGTCTAACAGTCGCTTGACTTAAAAGCGATGAAATCTA
ACAAGGAGGAATCACAATG (SEQ ID NO: 48)

CTGTCAGAGGTTTTTTATTTTAAATATGAAAAATGAAAGATAAAATTTACTGACAGAAAAGTCAACAAG
CTTAAAAATAAAAAGAAACACCCGAAAGCATTGCCATAGGTACTCTTATCAGATAATCTGAAAATAAAA
ATGGACTCAGGCTAGAAAAATAAAGGCTTTTATGAAAGAAAGACTTGCATTTGTTGTTGAAAAATGCTA
AAATACATAAGTCCGACTTTTTAGATATATTTAAATTTGTATTTATATCTTTCGGGAAATTTTTAAGGA
GGTACTTTTGCTTG (SEQ ID NO: 49)

FIGURE 1J

GAGCCTTCTCGGCGTCTTGTTAAATTTGATAAAACTTATTATCAAATTTAATGAGATGTCGAAAGTGCA
TCTATAAATTCCGCCAACTCCGCCTTAGTAGCGGCAGTGGTACAAATATTTAAAGGAGAAACTCGCAAA
ATG (SEQ ID NO: 50)

ATGACGAAATTGATAACATCGTTTAAGAAAGCTCCGTAAGTAAATTTAGTCTTACCAACAGTTACTGAT
AAGTGGGCAAGAGCGCTGCTTTGGACGAACATTCCAATCAAAGGGTTAATCAAATTATCAACCAAAGAT
TTAACTAAAGCAGTAAAAGCTGCCCCGATGATAACCCCAACGGCCAAGTCTAAGACATTGCCACGCAAA
ATAAAGTTTTTAAATTCCTTTAACATAAATCCTCCTATATAAATAGTTTATAAAACCTTTAATCAAATT
ATATCAAAAAGTTTAAAGATGACAAAGTGTGGGTTCTTGTCTTTTTCAGTAAATTCATTGATTTTATTT
AAAATTTTAAAAGATATATAAAAAGAACTGGAAAGAATAAAAAAAGTCTAAAAAGTCCTTGACAAGGCA
CATCTCCTTTGATAGAATAGACAAGTGCTGTTAAAAACAGTATGTAGCGACGAAACGAGAGGTTGCGAC
ACACCCGAAGGTATTGCCATACCTAACGTGTCGGTTTTCCCGTGGAGCTAGCCTATTGAATACAATAGA
CGAGAGGAGAAAAAATG (SEQ ID NO: 51)

AAATCTAAATGTTTTCTCTTGACTAAATCTGACCATTGAGATAAAATAAGAATATGTTAGCACACAACT
ATTAAGAGTGCTAAAAATAAAAAATGGAGTAAAGTATAATG (SEQ ID NO: 52)

AAATCTAAATGTTTTCTCTTGACTAAATCTGACCATTGAGATAAAATAAGAATATGTTAG
CACTCAACTATTAAGAGTGCTAAAAATAAAAAATGGAGGAAAGTATAATG (SEQ ID NO: 180)

ATGGTTTTGTCGGAAAAATTTTTTGACAGAGTCATATTTTACTGTTATTATTAACAGAATAGTCCCCTG
ATAGTAAAATATGAGGGTGCCCATCGGGCGTAAGAAAGGAAATAAACATG (SEQ ID NO: 53)

TATTTGGTGATTTTTCAAATTAGAATTCATATTTTATTTAAAAGTCTTTTCTAAAGACTTTTGTTTACT
TTACTAGAGAAAACGGTTGAATTCAGGCAAAAAATAACGTATAATTAACATGTATCTAAGAAATTTTTA
ATGAGATATTTCTGTCAGTATTAGAAAATGTAAAGTTCTCTAAAGATGAGAAAGTTAAGTAACTGACAG
AAGTGAAATTATTAGTTTTTAGTTTGATCTGGCTTTTTACAGATAAATTTAAAGGAGGTGTCTTATG
(SEQ ID NO: 54)

TGGATATTTTTTATAAATCTGGTTTGAACAAATTATATTGACATCTCTTTTTCTATCCTGATAATTCTG
AGAGGTTATTTTGGGAAATACTATTGAACCATATCGAGGTGGTGTGGTATAATGAAGGGAATTAAAAAA
GATAGGAAAATTTCATG (SEQ ID NO: 153)

TCCGGACATTCATTGAGTGCATGATGCACAGTAACCATAGAAAGGAAGACACAATG
(SEQ ID NO: 154)

LACTOCOCCUS PROMOTERS AND USES THEREOF

CROSS-REFERENCE TO RELATED APPLICATIONS

This application is the U.S. National Phase under 35 U.S.C. §371 of International Application PCT/EP2008/050352, filed Jan. 14, 2008, which claims priority to EP 07447001.4, filed Jan. 12, 2007 and EP 07120653.6, filed Nov. 14, 2007.

FIELD OF THE INVENTION

The invention is in the field of molecular biology, and relates to recombinant engineering and protein expression. More in particular, the invention relates to nucleic acids for recombinant expression of proteins comprising sequences derived from *Lactococcus* and useful as promoters. The invention further relates to vectors comprising the said nucleic acids and host cells transformed therewith. The invention also covers the use of host cells comprising the said nucleic acids or vectors for expressing heterologous or homologous proteins; and also for delivery, especially therapeutic delivery, of the said proteins to subjects.

BACKGROUND OF THE INVENTION

Lactic acid bacteria are increasingly becoming important as hosts for recombinant expression of heterologous polypeptides in vitro (e.g., U.S. Pat. No. 5,559,007) as well as for in vivo or in situ expression and delivery of antigens and/or therapeutically relevant polypeptides (e.g., WO 97/14806).

Lactic acid bacteria, and particularly *Lactococcus*, are considered as GRAS-microorganisms (i.e., regarded as generally safe) and may thus be relatively readily administered to humans and animals.

However, achieving strong level of heterologous expression in lactic acid bacteria often requires the introduction of promoters and other sequences that are exogenous to these bacteria (e.g., see Wells et al., 1993A) and therefore may compromise the GRAS perception thereof.

Accordingly, there exists a need to provide further promoters which are derived from lactic acid bacteria, more preferably from *Lactococcus*, and can be favourably used for expression of proteins, preferably heterologous protein expression, therein.

Also needed are such promoters which can achieve high expression levels in order to obtain sufficient amounts of so-expressed proteins in industrial and/or therapeutic settings.

SUMMARY OF THE INVENTION

The aspects of the present invention address at least some, e.g., one or more, of the above discussed needs of the art.

In particular, the present inventors recognised nucleic acids and nucleic acid sequences derived from *Lactococcus* that can be advantageously used as further promoters for recombinant expression, such as preferably expression of polypeptides, in host cells, preferably in bacteria, and more preferably in *Lactococcus*.

More in particular, the inventors set out and succeeded to identify nucleic acids and nucleic acid sequences from *Lactococcus* that can function as strong promoters, i.e., ones that achieve high level of expression, for recombinant expression, such as preferably expression of polypeptides, in host cells, preferably in bacteria, and more preferably in *Lactococcus*.

Strong expression can favourably increase the quantity of expression products, e.g., polypeptides, recombinantly produced by the host cells, that become available for further uses, such as, e.g., for purification from or for therapeutic delivery by the host cells.

Even more surprisingly, the inventors realised that the nucleic acids and nucleic acid sequences of the invention may act as promoters that are even stronger, especially when used in *Lactococcus*, than promoters previously derived from *Lactococcus*. More specifically, the nucleic acids and sequences of the invention may so-function as even stronger promoters, e.g. even stronger constitutive promoters, than the promoter of the thymidylate synthase gene (thyA) of *Lactococcus lactis* which, to the inventors' best knowledge, is the strongest *Lactococcus*-derived promoter, more in particular the strongest constitutive *Lactococcus*-derived promoter, to date. The thyA promoter of *Lactococcus lactis* is, to the inventors' best knowledge, also the strongest currently known promoter for recombinant, e.g., heterologous, gene expression in *Lactococcus*, and preferably in *Lactococcus lactis*.

Surprisingly, a combined transcriptome analysis as outlined in the examples together with sophisticated proteomics data was not proficient in suggesting the strength or activity of candidate promoters. In particular, some promoters identified were only weakly active when tested. In addition, some potential promoter sequences were not active outside the natural environment or native configuration, i.e. when tested with heterologous genes.

As an added advantage, particularly high expression is observed using the promoters of the invention inter alia for human IL-10, human peptide YY (PYY), human glucagon-like peptide-1 (GLP-1), human GLP-2 (GLP-2) and human trefoil factors (TTF) as preferred targets.

It shall also be appreciated that the nucleic acids and nucleic acid sequences identified by the inventors are derived from *Lactococcus*, which is established as a GRAS microorganism (i.e., "generally regarded as safe"). Consequently, compositions, e.g., host cells, comprising such promoters can be administered to humans and animals with less concern for biological safety than when introducing sequences originating from, e.g., non-GRAS microorganisms or other sources.

Thus, the invention provides advantageous *Lactococcus*-derived, i.e., comparably safe, nucleic acids and sequences that constitute further promoters, more preferably further strong promoters, and even more preferably promoters stronger than the thyA promoter, for use in numerous applications involving recombinant expression, e.g., of polypeptides, in host cells, preferably in bacteria and even more preferably in *Lactococcus*.

The present invention integrates the above relevant realisations in its diverse aspects.

Accordingly, in an aspect, the invention provides a recombinant nucleic acid comprising a promoter (P), being a native promoter from a *Lactococcus* species or a functional variant or functional fragment thereof, operably linked to one or more open reading frames heterologous to the promoter (P), characterised in that the promoter (P) is stronger in *Lactococcus* than the promoter of the thymidylate synthase gene (thyA) of *Lactococcus lactis*.

Related thereto, the invention thus also provides a recombinant nucleic acid comprising a promoter (P) operably linked to one or more open reading frames heterologous to the promoter (P), wherein the promoter (P) is chosen from the group comprising or consisting of the native promoters of genes of *Lactococcus* for 1) DNA-directed RNA polymerase, beta' subunit/160 kD subunit (rpoC), 2) DNA-directed RNA polymerase, beta subunit/140 kD subunit (rpb2), 3) DNA-binding ferritin-like protein (oxidative damage protectant) (dps), 4) pyruvate kinase (pyk), 5) glutamyl- and glutaminyl-tRNA synthetases (glnS), 6) enolase (eno), 7) glutamine synthetase (glnA) 8) HTH-type transcriptional regulator (glnR), 9) Xaa-His dipeptidase (argE or pepV)), 10) F0F1-type ATP synthase beta subunit (ATP synthase F1 beta subunit) (atpD), 11) 3-phosphoglycerate kinase (pgk), 12) glyceraldehyde-3-phosphate dehydrogenase/erythrose-4-phosphate dehydrogenase (gapA), 13) acetate kinase (ackA), 14) 3-oxoacyl-(acyl-carrier-protein) synthase (fabB), 15) 3-oxoacyl-(acyl-carrier-protein) reductase (fabG), 16) DNA-directed RNA polymerase, alpha subunit/40 kD subunit (rpoA), 17) Xaa-Pro aminopeptidase (pepP), 18) fructose/tagatose bisphosphate aldolase (tbp), 19) ribosomal protein S4 (rpsD), 20) superoxide dismutase (sodA), 21) ribosomal protein S12 (rpsL) and ribosomal protein S7 (rpsG), 22) ribosomal protein L18 (rplR) and ribosomal protein S5 (rpsE) and ribosomal protein L30/L7E (rpmD), 23) S-ribosylhomocysteine lyase (luxS), 24) ribosomal protein L19 (rplS), 25) ribosomal protein S11 (rpsK), 26) ribosomal protein L10 (rplJ), 27) ribosomal protein L7/L12 (rplL), 28) bacterial nucleoid DNA-binding protein/DNA binding protein HU (hup), 29) 50S ribosomal protein L28 (rpmB), 30) phosphotransferase system cellobiose-specific component IIB (lacE), 31) F0F1-type ATP synthase alpha subunit (atpA), 32) ABC-type sugar transport system (ATPase component) (malK), 33) acetoin dehydrogenase complex E1 component alpha subunit (acoA), 34) cell division protein (diflVA or ftsA), 35) UDP-galactopyranose mutase (glf), 36) glutamyl aminopeptidase (frvX), 37) predicted dehydrogenase related protein (mviM), 38) ribosomal protein S2, 39) translation initiation factor 3 (IF-3) (infC), 40) ribosomal protein L4 (rplD) and ribosomal protein L23 (rplW) and ribosomal protein L2 (rplB), 41) EMAP domain (ydjD), 42) transcription elongation factor (greA), 43) protease subunit of ATP-dependent Clp protease (clpP), 44) ribosomal protein L15 (rplO), 45) ribosomal protein L11 (rplK), 46) ribosomal protein S8 (rpsH), 47) ribosomal protein L21 (rplU), 48) ribosomal protein S13 (rpsM), 49) ribosomal protein S19 (rpsS) and ribosomal protein L22 (rplU) and ribosomal protein L16 (rplP) and ribosomal protein L14 (rplN), 50) ribosomal protein S10 (rpsJ), 51) co-chaperonin GroES (Hsp10) (cpn10), 52) ribosomal protein L24 (rplX) and 53) hypothetical protein LACR_0137 (duf965), and functional variants and functional fragments of the said native promoters.

The invention provides a recombinant nucleic acid, wherein the promoter (P) is chosen from the group consisting of the native promoters of genes of *Lactococcus*, preferably of *Lactococcus lactis*, for 1) DNA-directed RNA polymerase, beta' subunit/160 kD subunit (rpoC), 3) non-heme iron-binding ferritin (dpsA), 4) pyruvate kinase (pyk), 5) glutaminyl-tRNA synthetases (gltX), 6) phosphopyruvate hydratase (eno), 9) dipeptidase PepV (pepV), 12) glyceraldehyde-3-phosphate dehydrogenase (gapB), 13) acetate kinase (ackA), 18) fructose bisphosphate aldolase (fbaA), 20) superoxide dismutase (sodA), 21) ribosomal protein S12 (rpsL) and ribosomal protein S7 (rpsG), 22) ribosomal protein L18 (rplR) and ribosomal protein S5 (rpsE) and ribosomal protein L30/L7E (rpmD), 24) ribosomal protein L19 (rplS), 26) ribosomal protein L10 (rplJ), 28) HU-like DNA-binding protein (hllA), 29) 50S ribosomal protein L28 (rpmB), 30) phosphotransferase system IIB component (ptcB), 31) F0F1-type ATP synthase alpha subunit (atpA), 32) multiple sugar-binding transport ATP-binding protein (msmK), 33) pyruvate dehydrogenase E1 component alpha subunit (pdhA), 34) cell division protein (diflVA or ftsA), 35) UDP-galactopyranose mutase (glf1), 36) glutamyl aminopeptidase (pepA), 37) predicted dehydrogenase related protein (llmg_0272), 38) ribosomal protein S2 (rpsB), 39) translation initiation factor 3 (IF-3) (infC), 40) ribosomal protein L4 (rplD) and ribosomal protein L23 (rplW) and ribosomal protein L2 (rplB), 41) Phenylalanyl-tRNA synthetase beta chain (pheT), 42) transcription elongation factor GreA (greA), 43) ATP-dependent Clp protease proteolytic subunit (clpP), 44) ribosomal protein L15 (rplO), 45) ribosomal protein L11 (rplK), 46) ribosomal protein S8 (rpsH), 47) ribosomal protein L21 (rplU), 48) ribosomal protein S13 (rpsM), 49) ribosomal protein S19 (rpsS) and ribosomal protein L22 (rplU) and ribosomal protein L16 (rplP) and ribosomal protein L14 (rplN), 50) ribosomal protein S10 (rpsJ), 51) co-chaperonin GroES (Hsp10) (groES), 52) ribosomal protein L24 (rplX) and 53) putative holiday junction resolvase (llmg_0151), and functional variants and functional fragments of the said native promoters.

In an even more preferred embodiment, the invention provides a recombinant nucleic acid, wherein the promoter (P) is chosen from the group consisting of the native promoters of genes of *Lactococcus*, preferably of *Lactococcus lactis*, for 1) DNA-directed RNA polymerase, beta' subunit/160 kD subunit (rpoC), 3) non-heme iron-binding ferritin (dpsA), 4) pyruvate kinase (pyk), 5) glutaminyl-tRNA synthetases (gltX), 6) phosphopyruvate hydratase (eno), 9) dipeptidase PepV (pepV), 12) glyceraldehyde-3-phosphate dehydrogenase (gapB), 13) acetate kinase (ackA), 18) fructose bisphosphate aldolase (fbaA), 20) superoxide dismutase (sodA), 21) ribosomal protein S12 (rpsL) and ribosomal protein S7 (rpsG), 22) ribosomal protein L18 (rplR) and ribosomal protein S5 (rpsE) and ribosomal protein L30/L7E (rpmD), 24) ribosomal protein L19 (rplS), 26) ribosomal protein L10 (rplJ), 28) HU-like DNA-binding protein (hllA), 29) 50S ribosomal protein L28 (rpmB), 30) phosphotransferase system IIB component (ptcB), as defined in Table 1.

In a further preferred embodiment, the invention provides a recombinant nucleic acid comprising the promoter 28) bacterial nucleoid DNA-binding protein/HU-like DNA-binding protein (hlla or hup), operably linked to one or more open reading frames heterologous to the promoter. Even more preferably, said promoter is the PhllA promoter.

In a further preferred embodiment, the invention provides a recombinant nucleic acid comprising promoter 3) non-heme iron-binding ferritin (dpsA or LACR_2311), promoter 9) dipeptidase PepV (pepV or LACR_0908), or promoter 20) superoxide dismutase (sodA or LACR_0458), respectively, said promoter operably linked to one or more open reading frames heterologous to the promoter. Even more preferably, said promoter is the PdpsA, PpepV or PsodA promoter.

In a preferred selection, the invention provides a recombinant nucleic acid comprising a promoter (P) operably linked to one or more open reading frames heterologous to the promoter (P), wherein the promoter (P) is chosen from the group comprising or consisting of the native promoters of the genes of *Lactococcus* listed under 1) to 30) above, or Table 1, preferably the PhllA, the PdpsA, PpepV or PsodA promoter, and functional variants and functional fragments of the said native promoters.

In a further preferred embodiment, the above recited genes, and the respective native promoters and functional variants and functional fragments thereof, are derived from *Lactococcus lactis*.

In related exemplary aspects, also provided are vectors comprising the recombinant nucleic acids of the invention; chromosomally integrated expression cassettes, host cells transformed with the recombinant nucleic acids of the invention or with vectors comprising such; the use of the recombinant nucleic acids of the invention for achieving expression of expression products, preferably of one or more polypeptides, encoded by the said open reading frames, in a host cell; methods for recombinant expression and isolation of expression products, preferably polypeptides, of interest using said host cells; treatment methods involving in situ delivery of therapeutically relevant expression products, preferably polypeptides, e.g., antigens and/or non-vaccinogenic therapeutically active polypeptides, to humans or animals by such host cells; and related uses of the host cells for the manufacture of medicaments to facilitate the said delivery; pharmaceutical compositions comprising the said host cells; etc.

These and further aspects and preferred embodiments of the invention are described in the following sections and in the appended claims.

BRIEF DESCRIPTION OF FIGURES

FIG. 1 (A-J) illustrates preferred promoter sequences.

"Promoter" and "secretion signal" indicate the promoter and secretion signal that is in front of the TFF gene.

Figure 11:
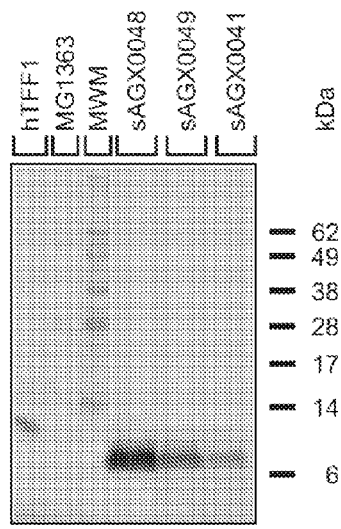

FIG. 11 Western blot analysis of supernatants of the various indicated strains. Lanes containing reference proteins are indicated with "hTFF1" (reference hTFF1) and "MWM" (molecular weight markers, molecular weights are indicated by "kDa"). All other lanes contain the equivalent of 0.5 ml of culture supernatant of the indicated strains, harvested as described above. The first antibody was mouse monoclonal anti-hTFF1: 1/1000 (Abnova: cat# H00007031-M02). The second antibody was goat anti-mouse-AP: 1/1000 (Southern Biotech: 4050-04) and detection was done with NBT/BCIP (Roche 11 697 471 0001). MWM are Invitrogen SeeBlue plus2 pre-stained standard (cat#LC5925).

Figure 12:
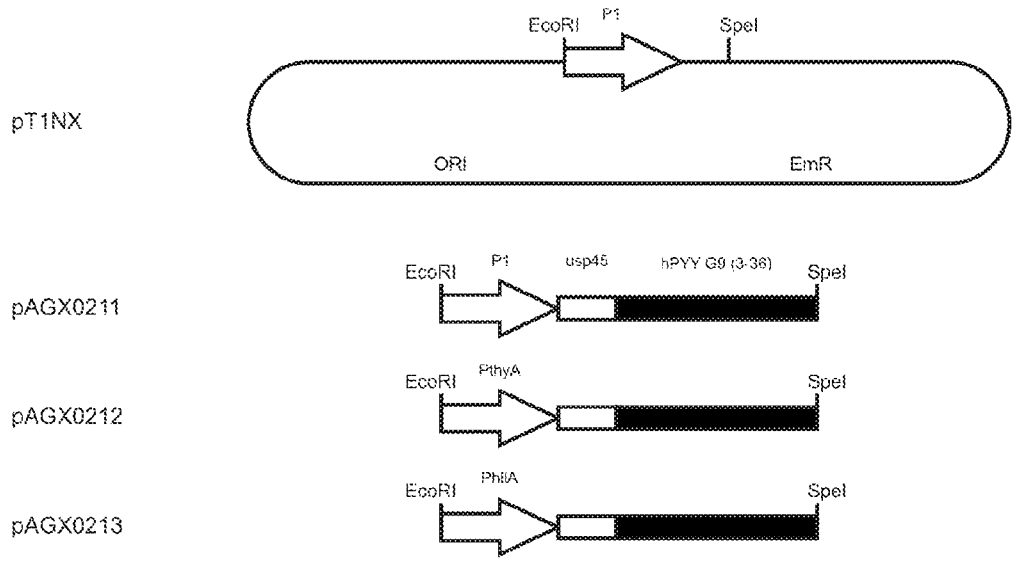
Figure 13:
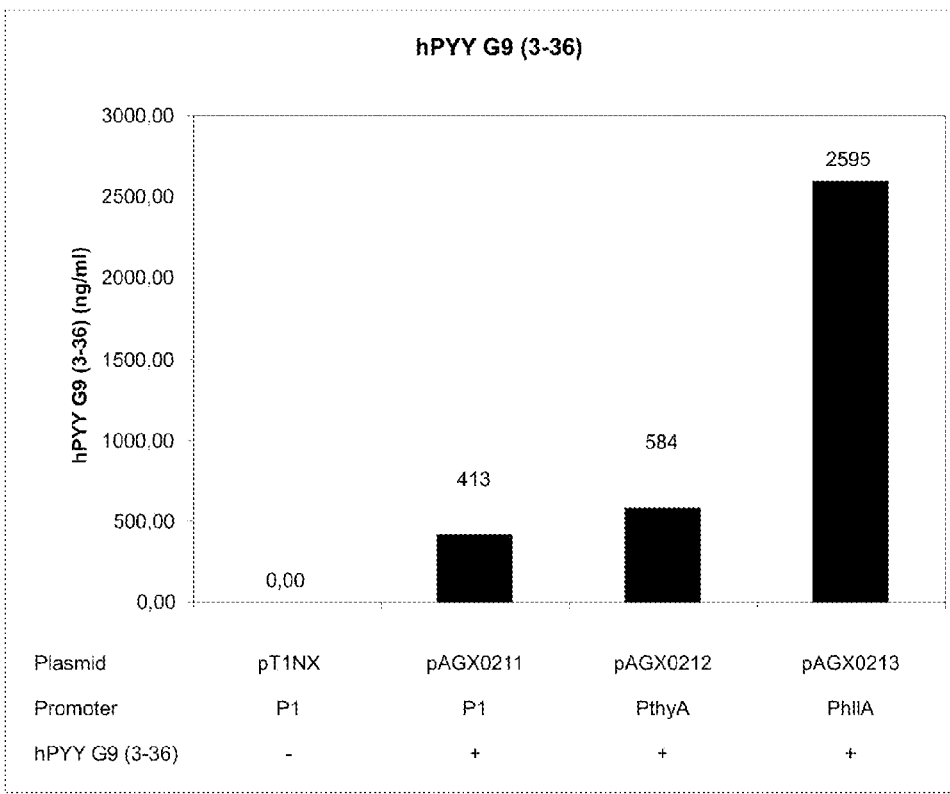

FIG. 12 Schematic overview of the structure of pT1NX and of the various hPYY G9 (3-36) expression plasmids used in this study. Expression plasmids pAGX0211, pAGX0212 and pAGX0213 were obtained by inserting the respective expression cassettes as EcoRI-SpeI fragments in the EcoRI-SpeI opened pT1NX. As such, the structure and position of all DNA sequences outside the expression cassettes, such as the origin of replication (ori) and erythromycin resistance marker (EmR), are identical for all plasmids. Genetic elements are not drawn to scale FIG. 13 Comparison of hPYY G9 (3-36) expression from P1 (Waterfield et al. 1995) (plasmid pAGX0211), PthyA (thymidylate synthase promoter, plasmid pAGX0212) and PhllA (promoter of bacterial nucleoid DNA-binding protein/DNA binding protein HU; SEQ ID NO: 28, plasmid pAGX0213) linked to the usp45 secretion signal and hPYY G9 (3-36). All plasmids were present in *L. lactis* MG1363. "Promoter" indicates the promoter that is upstream of the hPYY G9 (3-36) gene or present at the equivalent site in pT1 NX.

Figure 14:
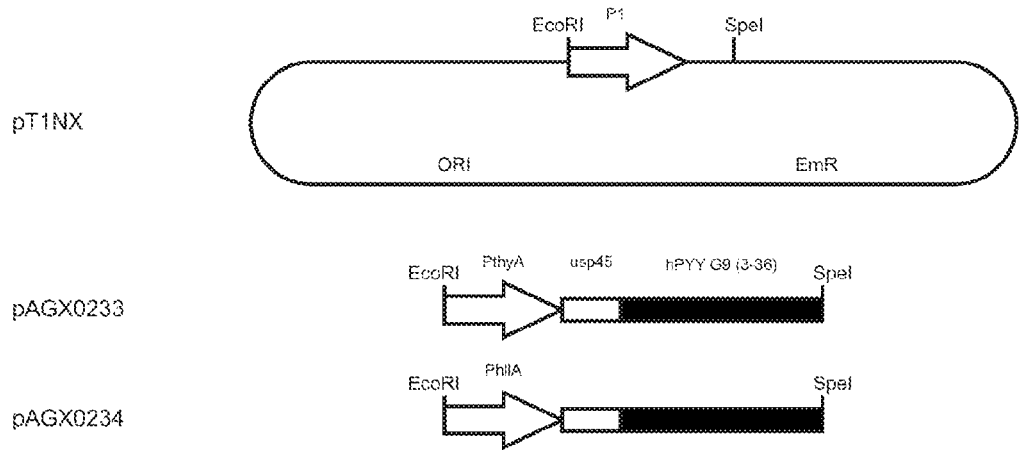

FIG. 14 Schematic overview of the structure of pT1NX and of the various hGLP-1 G8 (7-36) expression plasmids used in this study. Expression plasmids pAGX0233 and pAGX0234 were obtained by inserting the respective expression cassettes as EcoRI-SpeI fragments in the EcoRI-SpeI opened pT1NX. As such, the structure and position of all DNA sequences outside the expression cassettes, such as the origin of replication (ori) and erythromycin resistance marker (EmR), are identical for all plasmids. Genetic elements are not drawn to scale.

Figure 15:
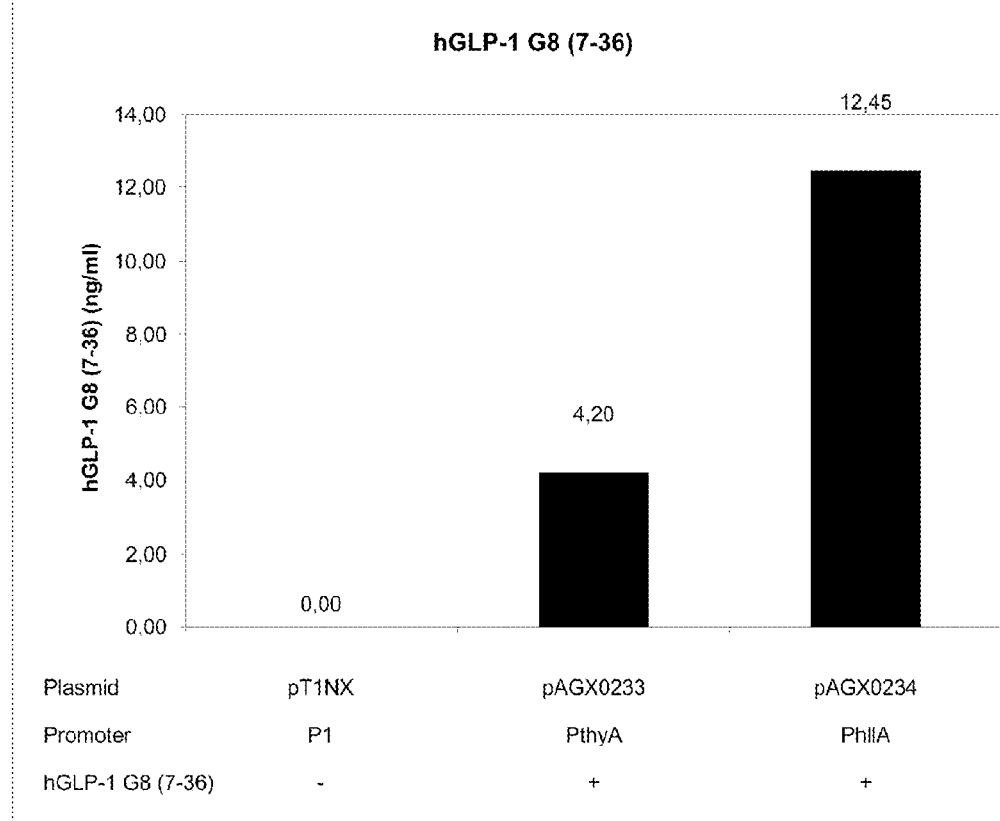

FIG. 15 Comparison of hGLP-1 G8 (7-36) expression from P1 (Waterfield et al. 1995) (plasmid pAGX0211), PthyA (thymidylate synthase promoter, plasmid pAGX0212) and PhllA (promoter of bacterial nucleoid DNA-binding protein/DNA binding protein HU; SEQ ID NO: 28, plasmid pAGX0213) linked to the usp45 secretion signal and hGLP-1 G8 (7-36). All plasmids were present in *L. lactis* MG1363. "Promoter" indicates the promoter that is upstream of the hGLP-1 G8 (7-36) gene or present at the equivalent site in pT1 NX.

Figure 16:
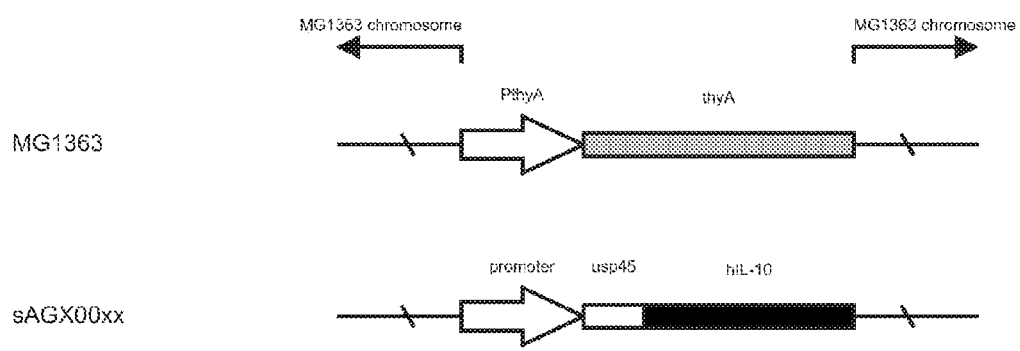
Figure 17:
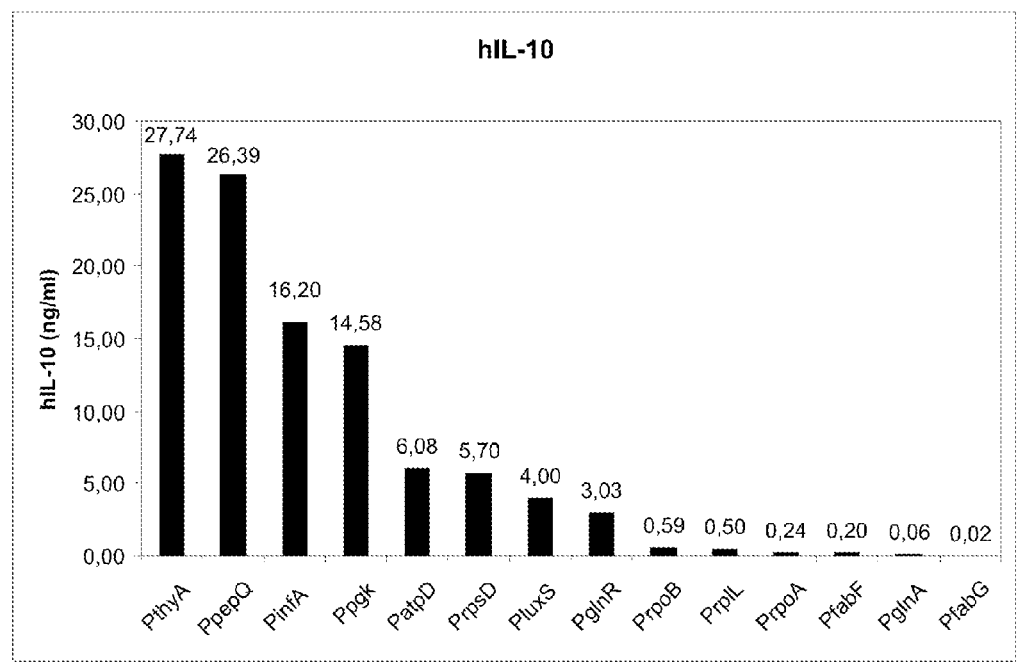

FIG. 16 Schematic comparison of *L. lactis* MG1363 and of the various hIL-10 expression strains used in this study. During construction, the hIL-10 expression cassettes are integrated in the *L. lactis* MG1363 chromosome by homologous recombination at identical sequences, both upstream as well as downstream of thyA and the hIL-10 expression cassettes respectively. Recombination points are schematically represented by \. This makes that all DNA sequences outside of the expression cassettes are identical for the above described strains. Here "promoter" is any one of the promoters, as present in strain "sAGX00xx" (Table 11). Genetic elements are not drawn to scale FIG. 17 Comparison of hIL-10 expression from PthyA (thymidylate synthase promoter, strain sAGX0005) with hIL-10 expression from any one of a series of strains (see FIG. 16 and Table 11) in which these lactococcal promoters were placed upstream of a usp45-hIL-10 fusion gene.

DETAILED DESCRIPTION OF THE INVENTION

As used herein, the singular forms "a", "an", and "the" include both singular and plural referents unless the context clearly dictates otherwise. By way of example, "a cell" refers to one or more than one cell.

The terms "comprising", "comprises" and "comprised of" as used herein are synonymous with "including", "includes" or "containing", "contains", and are inclusive or open-ended and do not exclude additional, non-recited members, elements or method steps.

The recitation of numerical ranges by endpoints includes all numbers and fractions subsumed within that range, as well as the recited endpoints.

The term "about" as used herein when referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less from the specified value, insofar such variations are appropriate to perform in the disclosed invention.

All documents cited in the present specification are hereby incorporated by reference in their entirety. In particular, the teachings of all documents herein specifically referred to are incorporated by reference.

Unless otherwise defined, all terms used in disclosing the invention, including technical and scientific terms, have the meaning as commonly understood by one of ordinary skill in the art to which this invention belongs. By means of further guidance, ensuing definitions are included to better appreciate the teaching of the present invention.

The term "nucleic acid" as used herein means a polymer of any length composed essentially of nucleotides, e.g., deoxyribonucleotides and/or ribonucleotides. Nucleic acids can comprise purine and/or pyrimidine bases and/or other natural (e.g., xanthine, inosine, hypoxanthine), chemically or biochemically modified (e.g., methylated), non-natural, or derivatised nucleotide bases. The backbone of nucleic acids can comprise sugars and phosphate groups, as can typically be found in RNA or DNA, and/or one or more modified or substituted sugars and/or one or more modified or substituted phosphate groups. The term "nucleic acid" further preferably encompasses DNA, RNA and DNA/RNA hybrid molecules, specifically including hnRNA, pre-mRNA, mRNA, cDNA, genomic DNA, amplification products, oligonucleotides, and synthetic (e.g. chemically synthesised) DNA, RNA or DNA/RNA hybrids. A "nucleic acid" can be double-stranded, partly double stranded, or single-stranded. Where single-stranded, the nucleic acid can be the sense strand or the antisense strand. In addition, nucleic acid can be circular or linear.

In a preferred embodiment, the nucleic acid comprising a promoter of the invention is DNA or RNA, more preferably DNA.

The term "recombinant nucleic acid" refers generally to a nucleic acid which is comprised of segments joined together using recombinant DNA technology. When a recombinant nucleic replicates in a host organism, the progeny nucleic acids are also encompassed within the term "recombinant nucleic acid".

Standard reference works setting forth the general principles of recombinant DNA technology include Molecular Cloning: A Laboratory Manual, 2nd ed., vol. 1-3, ed. Sambrook et al., Cold Spring Harbor Laboratory Press, Cold Spring Harbor, N.Y., 1989; Current Protocols in Molecular Biology, ed. Ausubel et al., Greene Publishing and Wiley-Interscience, New York, 1992 (with periodic updates) ("Ausubel et al. 1992"); Innis et al., PCR Protocols: A Guide to Methods and Applications, Academic Press: San Diego, 1990. General principles of microbiology are set forth, for example, in Davis, B. D. et al., Microbiology, 3rd edition, Harper & Row, publishers, Philadelphia, Pa. (1980).

By "promoter" is meant generally a region on a nucleic acid molecule, preferably DNA molecule, to which an RNA polymerase binds and initiates transcription. A promoter is preferably, but not necessarily, positioned upstream, i.e., 5', of the sequence the transcription of which it controls. In the present invention, specific promoters are indicated by the term "P", followed by the gene name from which they are derived For instance, "PthyA", which denotes the promoter of the thyA gene, and "PhllA" which denotes the promoter of the hllA gene.

The term "native promoter" refers to a promoter the nucleotide sequence of which is identical to that of a promoter present in nature, e.g., in a cell or organism in nature. The modifier "native promoter" thus relates to the sequence of the promoter and is not to be construed as requiring that the promoter be obtained or produced in any particular manner. By means of example and not limitation, the term would thus encompass promoters in their natural hosts, isolated there from, cloned and propagated using recombinant DNA technology, produced by an amplification method or generated by synthetic means, etc., insofar the sequence of such promoters would be the same as of their counterparts occurring in nature (see e.g. Table 1).

A skilled person understands that the native sequence of the promoter of a given gene may differ between different species of *Lactococcus* and/or between different subspecies within a single species of *Lactococcus* and/or between different strains within a single species or subspecies of *Lactococcus*, due to natural genetic divergence between the said species, subspecies and/or strains. Thus, such divergent but found-in-nature promoter sequences would be considered native.

A skilled person is in general capable of predicting and identifying natural bacterial promoters, such as promoters of *Lactococcus*. Nevertheless, to offer added guidance, a natural promoter may be often identified by analysing a genomic sequence or part thereof from a bacterium, preferably from a *Lactococcus* species; identifying an open reading frame therein, i.e., a succession of coding nucleotide triplets starting with a translation initiation codon (preferably, ATG) and closing with a translation termination codon (e.g., TAA, TAG or TGA) and not containing any internal in-frame translation termination codon; and analysing the sequence upstream of the said translation initiation codon to locate the upstream-most translation initiation codon, upstream to which there occurs an in-frame translation termination codon. Preferably, the transcription of the so-identified open reading frame can be verified experimentally, such as, e.g., by Northern blotting or RT-PCR; and the transcription initiation site (e.g., adjacent to the upstream-most and/or, perhaps, one or more of the more downstream translation initiation codons) can be evaluated using, e.g., 5'-rapid amplification of cDNA ends method (5'-RACE).

Typically, the sequences 5' adjacent to and proximal to the upstream-most translation initiation codon (and/or, if experimental evidence so indicates, one or more of the more downstream translation initiation codons) may comprise the native promoter responsible for transcribing the said ORF. By means of a preferred example, when the first nucleotide of the translation initiation codon is denoted +1 (e.g., the A nucleotide of the ATG codon is +1) and the nucleotide directly 5' thereof is denoted −1, then the term "native promoter" may refer to the sequence from about −500 to about +50, e.g., from about −500 to about +20, from about −500 to about +10, from about −500 to about +5, from about −500 to about +2, or from about −500 to about −1; preferably from about −400 to about +50, e.g., in preferred examples, from about −400 to about +20, e.g., from about −400 to about +10, from about −400 to about +5, from about −400 to about +2 or from about −400 to about −1; more preferably from about −300 to about +50, e.g., in preferred examples, from about −300 to about +20, e.g., from about −300 to about +10, from about −300 to about +5, from about −300 to about +2 or from about −300 to about −1; such as, e.g., in preferred examples, from about −200 to about +50 and in further preferred examples, from about −200 to about +20, e.g., from about −200 to about +10, from about −200 to about +5, from about −200 to about +2 or from about −200 to about −1; or such as, e.g., in other preferred example from about −100 to about +50 and in further preferred examples from about −100 to about +20, e.g., from about −100 to about +10, from about −100 to about +5, from about −100 to about +2 or from about −100 to about −1; insofar the said sequence displays the promoter activity.

The use of functional variants of native *Lactococcus* promoters in recombinant nucleic acids of the invention is also contemplated. The term "variant" refers to a sequence which is substantially identical (i.e., largely but not wholly identical) to a corresponding native sequence, e.g., to the sequence of a corresponding native *Lactococcus* promoter. "Substantially identical" refers to at least 60%, preferably at least 70% identical, more preferably at least 80% identical, e.g., at least 85% identical, even more preferably at least 90% identical, e.g., at least 91% identical, 92% identical, yet more preferably at least 93% identical, e.g., 94% identical, still more preferably at least 95% identical, e.g., at least 96% identical, even more preferably at least 97% identical, e.g., at least 98% identical, and most preferably at least 99% identical. Sequence alignments and determination of sequence identity can be done, e.g., using the Basic Local Alignment Search Tool (BLAST) originally described by Altschul et al. (1990), such as the "Blast 2 sequences" algorithm described by Tatusova and Madden (1999).

The use of functional fragments of native *Lactococcus* promoters in recombinant nucleic acids of the invention is also contemplated. As used herein, the term "fragment" refers to a sequence that has a 5' and/or 3' deletion of one or more nucleotides as compared to a native sequence, e.g., a native *Lactococcus* promoter or a variant thereof, but where the remaining nucleic acid sequence of the fragment is identical to the corresponding positions in the sequence of the native *Lactococcus* promoter or a variant thereof. The remaining sequence of a fragment can represents preferably at least 30%, e.g., at least 40%, more preferably at least 50%, e.g., at least 60%, even more preferably at least 70%, e.g., at least 80% or at least 85%, and still more preferably at least 90%, e.g., at least 95% or more of the nucleic acid sequence of the respective native *Lactococcus* promoter or variant thereof, such as identified by the methods of present invention, e.g. as provided by the specific SEQ ID NO:s of Table 1.

The term "functional" with reference to the variants and fragments of promoters as above refers to the fact that the particular variants and fragments will have at least partly retained the promoter activity, i.e., the capability to bind RNA polymerase and initiate transcription, of the corresponding native promoter. Preferably, such functional variants or functional fragments may retain at least 50% of the activity of the corresponding native promoter, e.g., at least 60%, more preferably at least 70%, e.g., at least 80%, yet more preferably at least 85%, e.g., at least 86%, at least 87%, at least 88% or 89%, still more preferably at least 90%, e.g., at least 91%, at least 92%, at least 93%, at least 94%, and most preferably at least 95%, e.g., at least 96%, at least 97%, and very preferably at least 98% or at least 99% of the activity of the corresponding native promoter. Also preferably, such functional variants or functional fragments may even have higher activity than the corresponding native promoter.

A skilled person can also appreciate that in embodiments the recombinant nucleic acids of the invention may even comprise more than one promoter (P) and/or functional variant and/or functional fragment of the invention. For instance, said promoters, functional variants or functional fragments—which may be same or different—can be operably linked to and control the expression of distinct transcription units within the said recombinant nucleic acids. Alternatively or in addition, expression of a single transcription unit may be controlled by more than one promoter(s), functional variant(s) and/or functional fragment(s), linked operably thereto, which can be same or different. For example, operable association of more than one of the above elements having promoter activity with a single transcription unit may further increase the level of transcription of the said unit. By means of example and not limitation, such promoters, functional variants and/or functional fragments may be arranged sequentially, e.g., sequentially upstream of the respective transcription unit.

Yet alternatively, the invention also envisages recombinant nucleic acids comprising chimeric promoters including two or more portions derived from different promoters, functional variants and/or functional fragments of the invention, and together constituting a new promoter.

A skilled person is aware of techniques to evaluate the activity of promoters. For example, a nucleic acid sequence whose activity as a promoter is sought to be determined can be inserted into a recombinant reporter construct such that it is operably linked with a reporter sequence, preferably a reporter coding sequence, such as, e.g., green fluorescent protein (GFP) or chloramphenicol acetyl transferase (CAT), etc. and the expression and/or accumulation of the reporter mRNA (e.g., by Northern blotting, quantitative RT-PCR, etc.)

and/or protein (e.g., by Western blotting, ELISA, measurement of fluorescence or enzymatic activity, etc.) is assayed when the said reporter construct is introduced into host cells or organisms of interest.

In an exemplary preferred embodiment, the expression can be measured for a protein heterologous to the organism in which the expression is measured, e.g., heterologous to bacteria, preferably heterologous to *Lactococcus*, even more preferably heterologous to *Lactococcus lactis*. For instance, in a preferred embodiment, expression in bacteria, preferably in *Lactococcus*, even more preferably in *Lactococcus lactis*, may be assessed for a gene encoding a polypeptide of eukaryotic origin, even more preferably for any of the genes encoding the therapeutically relevant polypeptides intended for expression using the nucleic acids of the invention (as described elsewhere in this specification), preferably GLP-2, GLP-1, PYY and TFF, and yet more preferably for any of immuno-modulatory polypeptides, cytokines, growth factors or interleukins, such as, very preferably for hIL-10. Values so measured for the assayed nucleic acid sequences indicate the activity or strength of potential promoters comprised within such sequences. A skilled person also understands that to ensure the comparative nature of such promoter activity assays, conditions other than the assayed nucleic acid sequences should be kept about the same or, ideally, the same between the different assays. Such conditions may comprise, by means of example, the quantity of the reporter construct introduced into cells, the transformation method used the said introduction, the number and site of integration of such reporter constructs in the genome of the assayed recipient cells, and/or the state (e.g., growth phase, e.g., preferably exponential growth phase) of the recipient host cells at the time of the measurement, etc. An exemplary way of measuring the strength of a promoter in *Lactococcus lactis* recipient cells using hIL-10 as the expressed gene is indicated in Example 2. A further exemplary way of measuring the strength of a promoter in *Lactococcus lactis* and *Lactobacillus casei* recipient cells using GLP2 as the expressed gene is indicated in Examples 3 and 4. Even more exemplary ways of measuring the strength of a promoter in *Lactococcus lactis* recipient cells, now using GLP1, hPYY, hIL-10 and TFF as the expressed genes, are indicated in Examples 5-9. Experiments using *Lactobacillus casei* as recipient cells result in similar outcomes (not depicted).

Accordingly, a promoter (1) which is said to be "stronger" than another promoter (2) would display a significantly higher activity as evaluated by suitable assays, e.g., those described in the preceding paragraph, e.g., the assay as exemplified in Examples 2 to 9. Significantly higher activity refers to a statistically significant finding of higher activity for promoter (1), e.g., preferably with $p<0.5$ or $p<0.05$.

The activity of promoter (1) may be higher than the activity of promoter (2) by any extent and, preferably, the activity of promoter (1) may be higher than the activity of promoter (2) by at least 1% of the value of activity of promoter (2), e.g., by at least 2%, at least 3% or at least 4%, more preferably by at least 5%, e.g., by at least 6%, at least 7%, at least 8% or at least 9%, even more preferably by at least 10%, e.g., by at least 15%, yet more preferably by at least 20%, e.g., by at least 30% or at least 40%, even more preferably by at least 50%, e.g., at least 60%, at least 70%, at least 80% or at least 90%, and in further very preferred examples by at least 100%, at least 150%, at least 200%, at least 250%, at least 300%, at least 400%, or at least 500% of the value of activity of promoter (2); or in further very preferred examples the activity of promoter (1) may be at least 10× higher than the activity of promoter (2), such as at least about 50×, at least about 100×, at least about 500× or at least about 1000× higher.

Accordingly, to realise functional variants or fragments of promoters, especially of promoters disclosed by the present invention, the skilled person would know to prepare such variants (e.g., by targeted or random mutagenesis) or fragments (e.g., by 5' and/or 3' truncation, e.g., by restriction digestion or PCR) and assay such variants or fragments for their promoter activity as above. Nevertheless, by means of further guidance and not limitation, it is noted that bacterial promoters often include consensus sequences adjacent to positions −10 and −35. Accordingly, functional fragments of bacterial, e.g., *Lactococcus* promoters, may preferably comprise at least sequences corresponding to positions in the native promoters from about −10 to about −35, more preferably from about −8 to about −40, even more preferably from about −5 to about −40 or from about −5 to about −45, and still more preferably from about −2 or −1 to about −50. Moreover, functional variants of bacterial, e.g., *Lactococcus* promoters, may preferably comprise consensus sequences adjacent to positions −10 and −35 as present in the native counterpart promoters or as known in the art.

An "operable linkage" is a linkage in which the regulatory DNA sequences and the DNA sequence sought to be expressed are connected in such a way as to permit expression.

For example, DNA sequences, such as, e.g., preferably a promoter and a heterologous open reading frame, are said to be operably linked if the nature of the linkage between the sequences does not (1) result in the introduction of a frameshift mutation, (2) interfere with the ability of the promoter to direct the transcription of the open reading frame, or (3) interfere with the ability of the open reading frame to be transcribed by the promoter region sequence.

In an exemplary preferred embodiment, the said promoter may be positioned upstream of, i.e., 5' of, the open reading frame(s) to which it is operably linked.

The precise nature of the regulatory regions needed for expression may vary from organism to organism, but shall in general include a promoter region which, in prokaryotes, contains both the promoter (which directs the initiation of RNA transcription) as well as the DNA sequences which, when transcribed into RNA, will signal the initiation of protein synthesis. Such regions will normally include those 5'-non-coding sequences involved with initiation of transcription and translation, such as the Pribnow-box (cf. TATA-box), Shine-Dalgarno sequence, and the like.

Advantageously, the respective translation initiation codon with which a given promoter of the invention is normally associated in nature may not be included in recombinant nucleic acids of the invention, such as to prevent translation initiation from such codons. For example, the 3' end of the promoter may be truncated at the −1 position or upstream thereof; alternatively, the translation initiation codon may be mutated (e.g., from ATG to a different codon); etc. Yet alternatively, the said native translation initiation codon may be present, and possibly also several (e.g., preferably ≤20, more preferably ≤10, yet more preferably ≤5, e.g., at most 1, 2, 3 or 4) subsequent codons of the open reading frame associated with the given promoter in nature, and a heterologous open reading frame of interest may be fused thereto in-frame to produce a fusion product.

The term "open reading frame" or ORF refers to a succession of coding nucleotide triplets starting with a translation initiation codon (preferably ATG) and closing with a translation termination codon (e.g., TAA, TAG or TGA) and not containing any internal in-frame translation termination codon, and potentially capable of encoding a polypeptide. Hence, the term may be synonymous with "coding sequence" as used in the art. In the recombinant nucleic acid of the invention, the translation initiation codons of the one or more ORFs may typically be associated with regulatory sequences controlling initiation of translation, e.g., with the Shine-Dalgarno sequence. It is also known that in bacteria, including *Lactococcus*, multi-cistronic units containing two or more sequential ORFs controlled by a common upstream promoter may be created by associating downstream translation initiation codons with the said sequences controlling such translation initiation.

The term "heterologous", when referring to the relationship between a given ORF and a promoter, means that the said promoter is not normally associated with, i.e., is not normally controlling the transcription of, the said ORF in nature. In other words, the association is created by recombinant DNA techniques in the recombinant nucleic acids of the invention.

The term "*Lactococcus*" generally refers to the genus *Lactococcus* and encompasses any taxon (e.g., species, subspecies, strain) classified as belonging to such in the art. By means of example, *Lactococcus* includes the species *Lactococcus garvieae*, *Lactococcus lactis*, *Lactococcus piscium*, *Lactococcus plantarum* and *Lactococcus raffinolactis*, and any subspecies and strains thereof.

In preferred embodiments of the invention the *Lactococcus* is *Lactococcus lactis*. *Lactococcus lactis* includes, without limitation, *Lactococcus lactis* ssp. *cremoris*, *Lactococcus lactis* ssp. *hordniae*, *Lactococcus lactis* ssp. *lactis*, *Lactococcus lactis* ssp. by *diacetylactis*.

In further preferred embodiments of the invention the *Lactococcus lactis* is *Lactococcus lactis* ssp. *cremoris* or *Lactococcus lactis* ssp. *lactis*, more preferably *Lactococcus lactis* ssp. *lactis*, and encompasses any strains thereof, such as, e.g., *Lactococcus lactis* ssp. *cremoris* SK11 or *Lactococcus lactis* ssp. *lactis* MG1363.

In preferred embodiments, the promoter (P) is derived from *Lactococcus* as defined above, more preferably from the preferred *Lactococcus* taxons as defined above, esp. in the two preceding paragraphs.

When a promoter (P) is said to be stronger than the *Lactococcus lactis* thyA promoter in *Lactococcus*, this means it is stronger in at least one and potentially in more than one or in all *Lactococcus* taxons (e.g., species, subspecies or strains). Preferably, a promoter (P) may be so-stronger in at least *Lactococcus lactis*. Also preferably, a promoter (P) may be so-stronger in at least *Lactococcus lactis* ssp. *cremoris* and *Lactococcus lactis* ssp. *lactis*, more preferably in at least *Lactococcus lactis* ssp. *lactis*.

The term "thymidylate synthase" refers to the enzyme EC 2.1.1.45 and "thymidylate synthase (thyA) gene of *Lactococcus lactis*" denotes a gene encoding the said enzyme in a *Lactococcus lactis*. The sequence of the thyA gene from several *Lactococcus lactis* taxons has been described, such as, e.g., from *Lactococcus lactis* ssp. *lactis* MG1363 (Ross et al., 1990; Steidler et al., 2003; Genbank accession: AF462070), *Lactococcus lactis* ssp. *lactis* IL1403 (Bolotin et al., 2001; Genbank GeneID: 1115198) and *Lactococcus lactis* ssp. *cremoris* SK11 (Genbank accession: NC_008527, locus LACR_1631, Genome GeneID: 4434110). A skilled person is capable of identifying and isolating thyA gene homologues from further taxons of *Lactococcus lactis*.

The promoter of thyA gene thus refers to a native promoter of any thyA gene as defined herein. By means of example, a given thyA promoter may refer to nucleic acid sequence from about −500 to about +50 of the corresponding thyA gene (+1 denoting the first nucleotide of the translation initiation codon of a given thyA gene); and by means of further preferred examples from about −500 to about +20, from about −500 to about +10, from about −500 to about +5, from about −500 to about +2, or from about −500 to about −1; from about −400 to about +50, from about −400 to about +20, from about −400 to about +10, from about −400 to about +5, from about −400 to about +2 or from about −400 to about −1; from about −300 to about +50, from about −300 to about +20, from about −300 to about +10, from about −300 to about +5, from about −300 to about +2 or from about −300 to about −1; from about −200 to about +50, from about −200 to about +20, from about −200 to about +10, from about −200 to about +5, from about −200 to about +2 or from about −200 to about −1; or from about −100 to about +50, from about −100 to about +20, from about −100 to about +10, from about −100 to about +5, from about −100 to about +2 or from about −100 to about −1; insofar the said sequence displays about the same and preferably the same strength as the thyA promoter in nature.

Preferably, the thyA promoter for use as reference in the present invention is the promoter of the thyA gene from *Lactococcus lactis* ssp. *lactis* MG1363, and a promoter of the invention is stronger thereto as defined above.

In an exemplary assay, described in Example 2 and based on Steidler et al. 2003 (ibid.), the thyA promoter of *L. lactis* ssp. *lactis* MG1363 directs expression of human IL-10 when integrated in a single copy to the thyA locus in the MG1363 strain of 6.5 ng/1×10$^9$ bacteria. Accordingly, a promoter of the invention that is stronger than thyA promoter may, in the said assay, achieve expression of hIL-10 higher than 6.5 ng/1×10$^9$ bacteria, preferably ≥7 ng/1×10$^9$ bacteria, e.g., ≥8 ng/1×10$^9$ or ≥9 ng/1×10$^9$ bacteria, even more preferably ≥10 ng/1×10$^9$ bacteria, e.g., ≥11 ng/1×10$^9$ bacteria, ≥12 ng/1×10$^9$ bacteria, ≥13 ng/1×10$^9$ bacteria or ≥14 ng/1×10$^9$ bacteria, yet more preferably ≥15 ng/1×10$^9$ bacteria, still more preferably ≥20 ng/1×10$^9$ bacteria, e.g., ≥25 ng/1×10$^9$ bacteria, ≥30 ng/1×10$^9$ bacteria, ≥35 ng/1×10$^9$ bacteria or ≥40 ng/1×10$^9$ bacteria, and most preferably ≥50 ng/1×10$^9$ bacteria or more, e.g. ≥100 ng/1×10$^9$ bacteria; and in further very preferred examples ≥200 ng/1×10$^9$ bacteria, such as ≥500 ng/1×10$^9$ bacteria, or ≥1000 ng/1×10$^9$ bacteria, or ≥2000 ng/1×10$^9$ bacteria, or ≥5000 ng/1×10$^9$ bacteria.

In further exemplary assays, e.g. as described in Examples 3 and 4, the MG1363 strain or *L. casei* comprises the pT1NX vector, wherein the thyA promoter of *L. lactis* ssp. *lactis* MG1363 directs expression of the human GLP-2 gene. Accordingly, a promoter of the invention, e.g. the PhllA promoter, is stronger than the thyA promoter when equivalents of 1 ml of cultures harvested at the end of log phase, loaded on SDS-PAGE and analyzed by western blot, the amount of GLP-2 expressed via the promoter of the invention is higher than via the thyA promoter. Further exemplary assays are described in Examples 5 to 9.

In a related embodiment, the invention thus also provides a recombinant nucleic acid comprising a promoter (P) operably linked to one or more open reading frames heterologous to the promoter (P), e.g. a GLP-2 gene, an hIL-10 gene, GLP-1 gene, hPYY gene or a TTF gene, wherein the promoter (P) is chosen from the group comprising or consisting of the native promoters of genes of *Lactococcus* listed under 1) to 53) in the Summary section, preferably the native promoters of genes of *Lactococcus* listed wherein the promoter (P) is chosen from the group consisting of the native promoters of genes of 1) DNA-directed RNA polymerase, beta' subunit/ 160 kD subunit (rpoC), 3) non-heme iron-binding ferritin (dpsA), 4) pyruvate kinase (pyk), 5) glutaminyl-tRNA synthetases (gltX), 6) phosphopyruvate hydratase (eno), 9) dipeptidase PepV (pepV), 12) glyceraldehyde-3-phosphate dehydrogenase (gapB), 13) acetate kinase (ackA), 18) fructose bisphosphate aldolase (fbaA), 20) superoxide dismutase (sodA), 21) ribosomal protein S12 (rpsL) and ribosomal protein S7 (rpsG), 22) ribosomal protein L18 (rplR) and ribosomal protein S5 (rpsE) and ribosomal protein L30/L7E (rpmD), 24) ribosomal protein L19 (rplS), 26) ribosomal protein L10 (rplJ), 28) HU-like DNA-binding protein (hllA), 29) 50S ribosomal protein L28 (rpmB), 30) phosphotransferase system IIB component (ptcB), as defined in Table 1 under 1) to 53), even more preferably the promoter listed under 1), 3)-6), 9), 12), 13), 18), 20)-22), 24), 26), and 28)-30) of Table 1, even more preferably the PhllA promoter listed under 28), the PdpsA promoter listed under 3), the PpepV promoter listed under 9), or the PsodA promoter listed under 20), and functional variants and functional fragments of the said native promoters. It is also preferred that the promoter (P) is chosen from the group comprising or consisting of nucleic acids set forth in SEQ ID NO: 1, 3 to 6, 9, 12, 13, 18, 20 to 22, 24, 26, 28 to 54, 160, 163 to 165, 167, 169, 171 to 180, and functional variants and functional fragments of the said native promoters.

The said designations are clear to a skilled person and teach specific genes from various *Lactococcus* taxons (e.g., species, subspecies and strains), such as the preferred *Lactococcus* taxons described above. Nevertheless, by virtue of further guidance Table 1 below mentions unique Gene ID numbers which identify the said genes as isolated form *Lactococcus lactis* ssp. *cremoris* SK11 (Genbank accession number for full length genome sequence of SK11: NC_008527) and ssp. *lactis* MG1363. The Gene ID numbers uniquely identify the said genes in the "Entrez Gene" database of NCBI (www.ncbi.nlm.nih.gov/entrez/query.fcgi?db=gene) as described in Maglott et al. 2005. On the basis hereof, a skilled person can identify and isolate homologues of the said genes from further taxons of *Lactococcus* other than SK11 and/or MG1363, e.g., the preferred species, subspecies *and* strains as taught herein. "Homologues" as used herein refers to sequences, esp. genes, from two or more different taxons that are similar (e.g., preferably, may be substantially identical as defined herein) as a result of originating from a common ancestor. Homologues of the above genes from SK11 and/or MG1363 preferably fulfil the same function in other *Lactococcus* taxons.

A skilled person can identify and isolate native promoters controlling the expression of genes listed in Table 1 from SK11 and/or MG1363 or homologues thereof from further *Lactococcus* taxons (including promoters which control the expression of genes that are found in multi-cistronic transcription units and thus may not contain a promoter directly upstream of their translation initiation codon; such as is the case in SK11 and/or MG1363, by means of illustration, for rpsL-rpsG with promoter upstream of rpsL directing the transcription of both; or for rplR-rpsE-rpmD with promoter upstream of rpsL directing the transcription of all; or for rplD-rplW-rplB with promoter upstream of rplD directing the transcription of all; or for rpsS-rplU-rplP-rplN with promoter upstream of rpsS directing the transcription of all; or for rpsM with a promoter upstream of an upstream gene infA encoding a translation initiation factor 1 (IF-1) directing the transcription of rpsM) following the teachings of this specification and using common knowledge in the art.

In a preferred embodiment, the invention provides a recombinant nucleic acid comprising a promoter (P) operably linked to one or more open reading frames heterologous to the promoter (P), wherein the promoter (P) is chosen from the group comprising or consisting of the native promoters of the genes of *Lactococcus* listed under 1) to 30) in the Summary section (i.e., the first 30 genes in Table 1), even more preferably the promoter listed under 1), 3)-6), 9), 12), 13), 18), 20)-22), 24), 26), and 28)-30) of Table 1, even more preferably the PhllA promoter listed under 28), DNA-binding ferritin-like protein (oxidative damage protectant) (dps) promoter listed under 3), the Xaa-His dipeptidase (argE or pepV) promoter listed under 9), or the superoxide dismutase (sodA) promoter listed under 20), and functional variants and functional fragments of the said native promoters.

In a preferred embodiment, the invention provides a recombinant nucleic acid comprising a promoter (P) operably linked to one or more open reading frames heterologous to the promoter (P), wherein the promoter (P) is chosen from the group comprising or consisting of nucleic acids set forth in SEQ ID NO: 1 to 54 and 157 to 180, and homologues thereof, even more preferably, SEQ ID NO: 1, 3 to 6, 9, 12, 13, 18, 20 to 22, 24, 26, 28 to 54, 160, 163 to 165, 167, 169, 171 to 180, and functional variants and functional fragments of the said native promoters, even more preferably, SEQ ID NO: 1, 3 to 6, 9. 12, 13, 18, 20 to 22, 24, 26, 28 to 30, 160, 163 to 165, 167, 169 and 171, and functional variants and functional fragments of the said native promoters, preferably SEQ ID NO:s 28, 3, 9, 158 and/or 20, and functional variants and functional fragments thereof.

The said sequences SEQ ID NO: 1 to 54 and 157 to 180, represent exemplary, but not limiting, native promoters associated with the expression of the genes listed under 1) to 53) above (as taught in more detail in Table 1) in *Lactococcus lactis* ssp. *lactis* MG1363 and/or *Lactococcus lactis* ssp. *cremoris* SK11. Accordingly, these promoters and homologues thereof (esp. from *Lactococcus* taxons other than MG1363 and/or SK11) and functional variants and functional derivatives thereof can be useful in recombinant nucleic acids of the invention for effecting expression of useful open reading frames in host cells, preferably in bacterial host cells, even more preferably in *Lactococcus*, yet more preferably in *Lactococcus lactis*, still more preferably in *Lactococcus lactis* ssp. *lactis*, such as in a preferred example strain MG1363.

In a further preferred embodiment, the promoter (P) is chosen from the group comprising or consisting of nucleic acids set forth in SEQ ID NO: 1 to 54, and 157 to 180, more preferably SEQ ID NO: 1, 3 to 6, 9. 12, 13, 18, 20 to 22, 24, 26, 28 to 54, 160, 163 to 165, 167, 169, 171 to 180, even more preferably, SEQ ID NO: 1, 3 to 6, 9, 12, 13, 18, 20 to 22, 24, 26, 28 to 30, 160, 163 to 165, 167, 169 and 171, most preferably SEQ ID NO: 28, 3, 9, 158 and/or 20, and homologues thereof, functional variants and/or functional fragments thereof.

In a yet further preferred embodiment, the promoter (P) is chosen from the group comprising or consisting of nucleic acids set forth in SEQ ID NO: 1 to 30, and 157 to 171, more preferably SEQ ID NO: 28, 3, 9, 158 and/or 20, and functional variants and functional fragments thereof.

In another preferred embodiment, the recombinant nucleic acids of the invention further comprise a transcription terminator sequence 3' to the said one or more open reading frames. For instance, if only one open reading frame is present, the terminator sequence may be advantageously located downstream, i.e., 3', thereof. If the recombinant nucleic acid contains two or more ORFs, e.g., successively ordered and forming together a multi-cistronic transcription unit, the transcription terminator may be advantageously positioned 3' to the most downstream ORF.

The term "transcription terminator" refers to a sequence element at the end of a transcriptional unit which signals termination of transcription. Preferably, a transcription terminator for use in the present invention will signal termination of transcription in host cells intended for use with the recombinant nucleic acids of the invention, such as, e.g., in bacterial host cells, even more preferably in *Lactococcus*, yet more preferably in *Lactococcus lactis*. Techniques for identification and isolation of suitable terminators, e.g., terminators from Lactococci, are known in the art (e.g., see van der Vossen et al., 1985), as are exemplary terminators, e.g., see van der Vossen et al., (1992), etc.

In a further preferred embodiment, the recombinant nucleic acids of the invention further comprise an operator configured to control transcription from the promoter (P). As used herein, the term "operator" refers to a nucleotide sequence, preferably DNA sequence, which controls the initiation and/or maintenance of transcription of a sequence from a promoter.

Typically, an operator may be generally placed between a promoter and a downstream sequence the transcription of which the promoters controls. Usually, an operator is capable of binding a repressor polypeptide, whereby it reduces the transcription from the said promoter. A useful repressor can alternate between a state in which it binds the operator and a state in which it does not and such alternation may be advantageously controlled by an external condition, e.g., an external substance or a particular metabolite. Accordingly, in host cells comprising a compatible repressor, the inclusion of an operator in the nucleic acid of the invention may allow to control the activity of the promoter and expression therefrom. Exemplary operators—repressor systems include, e.g., the lac system and see also, e.g., Nauta et al. (1996), or the histidine biosynthesis system (see, e.g., Delorme et al., 1999). Operator sequences may be generally derived from bacterial chromosomes.

In a further preferred embodiment, recombinant nucleic acids of the invention further comprise sequences configured to effect insertion of the said recombinant nucleic acids into the genome, e.g., a chromosome, of a host cell.

In a particularly preferred example, insertion of the nucleic acids of the invention into particular sites within a genome, e.g. chromosome, of a host cell may be facilitated by homologous recombination. For instance, the recombinant nucleic acids of the invention may comprise one or more regions of homology to the said site of integration within the genome e.g., a chromosome, of the host cell. The sequence at the said genome, e.g. chromosome, site may be natural, i.e., as occurring in nature, or may be an exogenous sequence introduced by previous genetic engineering.

For instance, the said region(s) of homology may be at least 50 bp, preferably at least 100 bp, e.g., at least 200 bp, more preferably at least 300 bp, e.g., at least 400 bp, even more preferably at least 500 bp, e.g., at least 600 bp or at least 700 bp, still more preferably at least 800 bp, e.g., at least 900 bp, or at least 1000 bp or more.

In a preferred example, two regions of homology may be included, one flanking each side of the expression unit(s) present in the nucleic acids of the invention. Such configuration may advantageously insert the relevant sequences, i.e., the ones effecting the expression of the open reading frames of interest from the promoters of the invention, in host cells. Ways of performing homologous recombination, especially in bacterial hosts, and selecting for recombinants, are generally known in the art. An exemplary and preferred method is, e.g., that of Steidler et al. (2003) for introducing exogenous sequences into the thyA locus of *Lactococcus*.

Hence, in a preferred embodiment, the invention also provides the recombinant nucleic acid when integrated into genome, e.g., a chromosome, preferably a bacterial chromosome, more preferably a *Lactococcus* chromosome. Such integration may be obtained in a host cell transformed with the said recombinant nucleic acid or a vector comprising such, as described elsewhere in this specification.

In a preferred embodiment, the one or more open reading frames linked to a promoter of the invention in the nucleic acids of the invention encode a polypeptide.

As can be appreciated, the essence of the invention primarily concerns novel promoters and their uses and the nature of the said expression products, preferably polypeptides, is not to be limited in any way.

Nevertheless, host cells comprising *Lactococcus* promoter-controlled open reading frames have been reported as means for in vitro production (see, e.g., U.S. Pat. No. 5,559, 007; Steidler et al., 1995; Wells et al., 1993B) and in vivo delivery (see, e.g., WO 97/14806; WO 01/02570; Steidler et al., 2003; Steidler et al., 2000) of relevant polypeptides of viral, prokaryotic or eukaryotic origin, including polypeptides useful in prevention or therapy of disease in man and animals.

Accordingly, in an embodiment, the said one or more open reading frames of the recombinant nucleic acids of the invention may encode an expression product, preferably a polypeptide, capable of eliciting a therapeutic response in a subject, preferably in a human or animal subject.

In a particularly useful, exemplary and not limiting, embodiment the said one or more open reading frames of the recombinant nucleic acids of the invention may encode an antigen and/or a non-vaccinogenic therapeutically active polypeptide.

As used herein, the term "antigen" generally refers to a substance that evokes an immune response, including humoral immunity and/or cellular immunity response, and that is capable of binding with a product, e.g., an antibody or a T cell, of the immune response. Hence, in a preferred example, an antigen requires a functioning immune system of a subject to which it is administered to elicit a physiological response from such a subject. The "antigen" of the present invention also encompasses "self-antigens" which do not provoke an immune response in a healthy individual but would do so in a person suffering from auto-immune disease, i.e. the failure of an organism to recognize its own constituent parts (down to the sub-molecular levels) as "self", which results in an immune response against its own cells and tissues. Any disease that results from such an aberrant immune response is termed an autoimmune disease. Accordingly, the "antigen" of the present invention also encompasses a (physiologically active) protein which would not provoke an immune response in a healthy individual but would do so in a person genetically deficient in said protein. In addition, the "antigen" of the present invention also encompasses an allergen which would not provoke an immune response in a healthy individual but would do so in a person suffering from an allergic disease.

An antigen according to the invention may be derived from any polypeptide to which an immune response in a human or animal subject would be therapeutically useful, e.g., from a pathogen, e.g., from a viral, prokaryotic (e.g., bacterial) or eukaryotic pathogen, from a non-physiological protein (e.g., a protein derived from cancer tissue), from allergen (e.g., for eliciting immune tolerance), etc. An antigen could also be a metabolite of a protein. As an example, the antigen could be a polysaccharide, a lipid or other. Strong promoters as described here could drive the expression of the necessary enzymes to synthesize or assemble said polysaccharide, lipid or other.

The term "a non-vaccinogenic therapeutically active polypeptide" refers generally to a polypeptide that, in a human or animal subject to which it is administered, does not elicit an immune response against itself and is able to achieve a therapeutic effect. Hence, the therapeutic effect of such a polypeptide would be expected to be directly linked to its own natural biological function whereby it can achieve particular effects in a body of a subject; rather than producing a therapeutic effect by acting as an immunogenic and/or immunoprotective antigen in the subject. Hence, the non-vaccinogenic therapeutically active polypeptide should be biologically active in its expressed form or, at least, must be converted into the biologically active form once released from the expressing host cell. Preferably, such biologically active form of the said polypeptide may display a secondary and preferably also tertiary conformation which is the same or closely analogous to its native configuration.

Preferably, the non-vaccinogenic therapeutically active polypeptide is also non-toxic and non-pathogenic.

In a preferred embodiment, the non-vaccinogenic therapeutically active polypeptide may be derived from human or animal, and may preferably correspond to the same taxon as the human or animal subject to which it is to be administered.

Non-limiting examples of suitable non-vaccinogenic therapeutically active polypeptides include ones which are capable of functioning locally or systemically, e.g., is a polypeptide capable of exerting endocrine activities affecting local or whole-body metabolism and/or the biologically active polypeptide(s) is/are one(s) which is/are capable of the regulation of the activities of cells belonging to the immuno-haemopoeitic system and/or the one or more biologically active polypeptides is/are one(s) which is/are capable of affecting the viability, growth and differentiation of a variety of normal or neoplastic cells in the body or affecting the immune regulation or induction of acute phase inflammatory responses to injury and infection and/or the one or more biologically active polypeptides is/are one(s) which is/are capable of enhancing or inducing resistance to infection of cells and tissues mediated by chemokines acting on their target cell receptors, or the proliferation of epithelial cells or the promotion of wound healing and/or the one or more biologically active polypeptides modulates the expression or production of substances by cells in the body.

Specific examples of such polypeptides include, without limitation, insulin, growth hormone, prolactin, calcitonin, luteinising hormone, parathyroid hormone, somatostatin, thyroid stimulating hormone, vasoactive intestinal polypeptide, cytokines such as IL-2, IL-3, IL-4, IL-5, IL-6, IL-7, IL-9, IL-10, IL-11, IL-12, IL-13, any of IL-14 to IL-32, GM-CSF, M-CSF, SCF, IFNs, EPO, G-CSF, LIF, OSM, CNTF, GH, PRL, the TNF family of cytokines, e.g., TNFa, TNFb, CD40, CD27 or FAS ligands, the IL-1 family of cytokines, the fibroblast growth factor family, the platelet derived growth factors, transforming growth factors and nerve growth factors, the epidermal growth factor family of cytokines, the insulin related cytokines, etc. Alternatively, the therapeutically active polypeptide can be a receptor or antagonist for the therapeutically active polypeptides as defined above. Alternatively, the therapeutically active polypeptide can be a neutralizing antibody, or the likes thereof. Further specific examples of such suitable polypeptides are listed, e.g., in WO 96/11277, page 14, lines 1-30, incorporated herein by reference; in WO 97/14806, page 12, line 1 through page 13, line 27, incorporated herein by reference; or U.S. Pat. No. 5,559,007, col. 8, line 31 through col. 9, line 9, incorporated by reference herein. Preferably, the suitable polypeptide is the IL-10 peptide, e.g. the human IL-10 (hIL-10), for instance as exemplified in Example 2, 5 or 9.

In a preferred embodiment, the suitable polypeptide is a Trefoil peptide, such as TTF1, TTF2 and/or TTF3. Three members of this family of trefoil peptides have been identified in humans and originally designated: pS2 (breast cancer oestrogen inducible gene, Lefebvre, 1993), SP (spasmolytic peptide) and ITF (intestinal trefoil factor). In the present nomenclature pS2 is renamed as TFF1, SP as TFF2 and ITF as TFF3 (see e.g. Wong et al., 1999). This new nomenclature is used throughout the present text. In humans, mice and rat TFF1 and TFF2 are predominantly found in the stomach while TFF3 is predominantly found in the duodenum and colon. TFF1 is thought to act through a cell surface receptor (Tan et al., 1997). Wong et al. (1999) give a recent overview of trefoil peptides. The contents of this article are incorporated by reference in the present disclosure. Trefoil peptides are secreted by epithelial mucus cells and are stable in an acid environment. These peptides contribute to the protection of the mucosa (formation of a gel over the epithelium) and are probably involved in the repair of damaged mucosa by stimulation of epithelial migration (Playford et al., 1996). The production of trefoil peptides increases locally in regions where damage occurs such as gastric ulcers and colitis (Wright et al., 1990). Babyatsky et al. (1996) have shown that the administration of recombinant trefoil peptides reduces the damage at those places. In contradiction with most other proteins that are important for the protection of the mucosa (such as epidermal growth factor), most studies have demonstrated that trefoil peptides cause little or no proliferation (Playford et al., 1996).

In another preferred embodiment, the suitable polypeptide is the PYY peptide, e.g. the human PYY (hPYY), and even more preferably hPYY Gly9 variant (3-36) as exemplified in Example 7.

In a further preferred embodiment, the suitable polypeptide is the glucagon-like peptide-1 (GLP-1 or GLP1), e.g. the human GLP-1 (hGLP-1), and even more preferably hGLP-1 Glycine 8 variant (7-36) as exemplified in Example 8. In a preferred embodiment, the suitable polypeptide is the glucagon-like peptide-2 (GLP-2 or GLP2). The human proglucagon gene (GenBank acc. nr. NM_002054) encodes a preproprotein that is cleaved into four distinct mature peptides, including glucagon-like peptide-2 (GLP-2). Externally administered GLP-2 produces a number of effects in individuals, e.g. humans, including intestinal growth, enhancement of intestinal function, reduction in bone breakdown and neuroprotection. GLP-2 may act in an endocrine fashion to link intestinal growth and metabolism with nutrient intake. GLP-2 and related analogs may be treatments for short bowel syndrome, Crohn's disease, osteoporosis and as adjuvant therapy during cancer chemotherapy. Preferably, the GLP-2 gene is adapted to the preferred codon usage in *Lactococcus*, e.g. *L. lactis*. Preferably, the gene encodes the amino acid sequence HADGSFSDEMNTILDNLAARDFINWLIQTKITD (SEQ ID 181).

In another preferred embodiment, the gene encodes a mature human GLP-2 analog with an alanine to glycine substitution at position 2, which was shown reduce susceptibility to degradation by dipeptidyl peptidase-IV (Booth et al. 2004), e.g. the gene encodes the amino acid sequence H GDGSFSDEMNTILDNLAARDFINWLIQTKITD (SEQ ID 182).

In an even more preferred embodiment, the GLP-2 gene is adapted to the preferred codon usage in *Lactococcus* and comprises an alanine to glycine substitution at position 2, e.g. the nucleotide sequence of h[Gly2]GLP-2:

CACGGTGATGGTTCATTTTCAGATGAAATGAACACTATCCTTGATAACCT

TGCTGCTCGTGATTTTATCAACTGGCTTATCCAAACTAAAATCACTGATT

AA (SEQ ID 183).

Accordingly, in an embodiment the recombinant nucleic acid of the invention encodes an antigen and/or a non-vaccinogenic therapeutically active polypeptide, wherein the said antigen is capable of eliciting an immune response, preferably protective immune response, in a human or animal subject, and/or the said non-vaccinogenic therapeutically active polypeptide is capable of producing a therapeutic effect in a human or animal subject.

WO 97/14806 further specifically discloses co-expression of antigens with immune response stimulatory molecules, such as, e.g., interleukins, e.g., IL-2 or IL-6, by bacteria. Accordingly, such co-expression using the promoters of the invention is also contemplated.

In a further preferred embodiment, the open reading frame according to the invention further comprises a sequence encoding a secretion signal in phase with a polypeptide encoded by the ORF. This advantageously allows for secretion of the expressed polypeptide from the host cell and thereby may facilitate, e.g., isolation or delivery.

Typically, a secretion signal sequence represents an about 16 to about 35 amino acid segment, usually containing hydrophobic amino acids that become embedded in the lipid bilayer membrane, and thereby allow for the secretion of an accompanying protein or peptide sequence from the host cell, and which usually is cleaved from that protein or peptide. Preferably, the secretion signal sequence may be so-active in a host cell intended for use with the nucleic acid comprising the said signal sequence, e.g., a bacterial host cell, preferably a lactic acid bacterium, more preferably *Lactococcus*, even more preferably *Lactococcus lactis*.

Secretion signal sequences active in suitable host cells are known in the art; exemplary *Lactococcus* signal sequences include those of usp45 (see, U.S. Pat. No. 5,559,007) and others, see, e.g., Perez-Martinez at al. (1992); Sibakov et al. (1991). Preferably, the signal sequence is located between the promoter sequence and the ORF, i.e. the signal sequence is located 3' from the promoter sequence and precedes the ORF of the polypeptide of interest. In a preferred embodiment, the signal sequence encodes the amino acid sequence MKKKIISAIL MSTVILSAAA PLSGVYA (usp45) (SEQ ID 184).

The present inventors surprisingly found that the combination of the PhllA promoter with a mutated usp45 signal sequence results in further controllable production and secretion of the polypeptide of interest. In particular, the mutant comprises an asparagine (N) at position 4 instead of a lysine (K). In a preferred embodiment, the signal sequence encodes the amino acid sequence MKK<u>N</u>IISAIL MSTVILSAAA PLSGVYADTN (SEQ ID 185).

In a further preferred embodiment the present invention relates to recombinant nucleic acid as defined herein, wherein said recombinant nucleic acid comprises:
(a) PdpsA, usp45 and hIL-10 (sAGX0012); PdpsA, usp45N4 and hIL-10;
  PpepV, usp45 and hIL-10 (sAGX0018); PpepV, usp45N4 and hIL-10;
  PsodA, usp45 and hIL-10 (sAGX0029); PsodA, usp45N4 and hIL-10;
  PhllA, usp45 and hIL-10 (sAGX0037); PhllA, usp45N4 and hIL-10;

(b) PdpsA, usp45N4 and hTFF1; PdpsA, usp45 and hTFF1;
  PpepV, usp45N4 and hTFF1; PpepV, usp45 and hTFF1;
  PsodA, usp45N4 and hTFF1; PsodA, usp45 and hTFF1;
  PhllA, usp45N4 and hTFF1 (sAGX0048); PhllA, usp45 and hTFF1 (sAGX0049);
(c) PdpsA, usp45N4 and hTFF3; PdpsA, usp45 and hTFF3 (sAGX0048);
  PpepV, usp45N4 and hTFF3; PpepV, usp45 and hTFF3;
  PsodA, usp45N4 and hTFF3; PsodA, usp45 and hTFF3;
  PhllA, usp45N4 and hTFF3 (sAGX0057); PhllA, usp45 and hTFF3;
(d) PdpsA, usp45N4 and hPYY; PdpsA, usp45 and hPYY (sAGX0048);
  PpepV, usp45N4 and hPYY; PpepV, usp45 and hPYY;
  PsodA, usp45N4 and hPYY; PsodA, usp45 and hPYY;
  PhllA, usp45N4 and hPYY (sAGX0057); PhllA, usp45 and hPYY; PhllA, usp45 and
  hPYY G9 (3-36) (sAGX0213);
(e) PdpsA, usp45N4 and GLP-1; PdpsA, usp45 and GLP-1;
  PpepV, usp45N4 and GLP-1; PpepV, usp45 and GLP-1;
  PsodA, usp45N4 and GLP-1; PsodA, usp45 and GLP-1;
  PhllA, usp45N4 and GLP-1; PhllA, usp45 and GLP-1;
(f) PdpsA, usp45N4 and GLP-2; PdpsA, usp45 and GLP-2;
  PpepV, usp45N4 and GLP-2; PpepV, usp45 and GLP-2;
  PsodA, usp45N4 and GLP-2; PsodA, usp45 and GLP-2;
  PhllA, usp45N4 and GLP-2; or PhllA, usp45 and GLP-2.

In a further aspect, the invention relates to a vector comprising the recombinant nucleic acid of the invention.

As used herein, "vector" refers to a nucleic acid molecule, typically DNA, to which nucleic acid fragments may be inserted and cloned, i.e., propagated. Hence, a vector will typically contain one or more unique restriction sites, and may be capable of autonomous replication in a defined host or vehicle organism such that the cloned sequence is reproducible. Vectors may include, without limitation, plasmids, phagemids, bacteriophages, bacteriophage-derived vectors, PAC, BAC, linear nucleic acids, e.g., linear DNA, etc., as appropriate (see, e.g., Sambrook et al., 1989; Ausubel 1992).

Factors of importance in selecting a particular vector, e.g., a plasmid, include inter alia: the ease with which recipient cells that contain the vector may be recognized and selected from those recipient cells which do not contain the vector; the number of copies of the vector which are desired in a particular host; and whether it is desirable to be able to "shuttle" the vector between host cells of different species. Preferred prokaryotic vectors include plasmids such as those capable of replication in *E. coli* (such as, for example, pBR322, ColE1, pSC101, pUC19, etc.). Such plasmids are describe in, e.g., Sambrook et al., 1989; Ausubel 1992. Particularly preferred vectors may be those able to replicate in *E. coli* (or other Gram negative bacteria) as well as in another host cell of interest, such as in a Gram positive bacterium, a lactic acid bacterium, preferably *Lactococcus*, more preferably *Lactococcus lactis* (see, e.g., Kok et al. (1984). Other preferred vectors may be those able to replicate and/or shuttle between one or more Gram positive bacteria but not in Gram negative bacteria. In a preferred embodiment, the vector is pT1NX as described by Steidler et al., (1998), which is specifically incorporated by reference herein.

In a further aspect, the invention provides a host cell transformed with the recombinant nucleic acid and/or with the vector of the invention. For example, such transformation may be useful for propagation and maintenance of the said nucleic acid or vectors.

Alternatively or in addition, and advantageously, a transformed host cell will be capable of transcribing the open reading frame(s) of the nucleic acid of the invention using the promoters of the invention and, preferably, expressing the expression products, preferably one or more polypeptides, encoded by the said open reading frames.

Hence, in a further aspect, the invention provides the use of the recombinant nucleic acid or vector of the invention for achieving expression of expression products, preferably one or more polypeptides, encoded by the said open reading frames, in a host cell. Preferably, the expression products, e.g., polypeptides, may be heterologous, i.e. exogenous, to the said host cell.

Preferably, a host cell will be a prokaryotic cell, for example a bacterial cell, more preferably a non-pathogenic and/or non-invasive bacterium, yet more preferably a Gram-positive bacterium, still more preferably a lactic acid bacterium (e.g., *Lactococcus* spp., *Streptococcus* spp., *Lactobacillus* spp., *Leuconostoc* spp., *Pediococcus* spp., *Brevibacterium* spp., *Propionibacterium* spp. or *Bifidobacterium* spp.), very preferably a *Lactococcus* bacterium and most preferably a *Lactococcus lactis* bacterium, e.g., as defined above; insofar the promoters of the invention are suitably active in the said host cells.

The recombinant nucleic acid or the vector of the invention may be present in the host cell extra-chromosomally, preferably autonomously replicating using an own origin of replication, or may be integrated into bacterial genomic DNA, e.g., bacterial chromosome, e.g., *Lactococcus* chromosome. In the latter case, a single or multiple copies of the said nucleic acid may be integrated, preferably a single copy; the integration may occur at a random site of the chromosome or, as described above, at a predetermined site thereof, preferably at a predetermined site, such as, in a preferred non-limiting example, in the thyA locus of *Lactococcus*, e.g., *Lactococcus lactis*, for instance as described by Steidler et al., (2003), which is specifically incorporated by reference herein.

Accordingly, in a further aspect the invention provides a host cell comprising a recombinant nucleic acid, as defined herein, wherein said promoter (P) is present in the chromosome of said host cell, and wherein said promoter (P) is operably linked to one or more open reading frames heterologous to said promoter (P), more preferably, said promoter (P) further comprises a signal sequence, preferably usp45 or usp45N4, more preferably said promoter (P) further comprises an operator configured to control transcription from the said promoter (P), and even more preferably, the promoter (P) is chosen from the group consisting of nucleic acids set forth in SEQ ID NO: 1, 3 to 6, 9, 12, 13, 18, 20 to 22, 24, 26, 28 to 54, 160, 163 to 165, 167, 169, 171 to 180, and homologues thereof, and functional variants and functional fragments thereof.

In a further aspect the invention provides a host cell as defined herein, wherein the said one or more open reading frames encode a polypeptide capable of eliciting a therapeutic response or immunogenic response in a subject, preferably in a human or animal subject, preferably the said one or more open reading frames encode an antigen and/or a non-vaccinogenic therapeutically active polypeptide, even more preferably the said antigen is capable of eliciting an immune response, preferably an immune tolerance response, in a human or animal subject, and/or the said non-vaccinogenic therapeutically active polypeptide is capable of producing a therapeutic effect in a human or animal subject. In a further preferred aspect the invention provides a host cell as defined herein, wherein the said non-vaccinogenic therapeutically active polypeptide is hIL-10, GLP-2, GLP-1, TFF or hPYY. In another further preferred aspect the invention provides a host cell as defined herein, wherein said antigen is capable of eliciting an immune response and used as a vaccine in a human or animal subject, and/or.

In a further preferred embodiment the present invention relates to a host cell as defined herein, wherein said host cell comprises:

(a) PdpsA, usp45 and hIL-10 (sAGX0012); PdpsA, usp45N4 and hIL-10;
  PpepV, usp45 and hIL-10 (sAGX0018); PpepV, usp45N4 and hIL-10;
  PsodA, usp45 and hIL-10 (sAGX0029); PsodA, usp45N4 and hIL-10;
  PhllA, usp45 and hIL-10 (sAGX0037); PhllA, usp45N4 and hIL-10;
(b) PdpsA, usp45N4 and hTFF1; PdpsA, usp45 and hTFF1;
  PpepV, usp45N4 and hTFF1; PpepV, usp45 and hTFF1;
  PsodA, usp45N4 and hTFF1; PsodA, usp45 and hTFF1;
  PhllA, usp45N4 and hTFF1 (sAGX0048); PhllA, usp45 and hTFF1 (sAGX0049);
(c) PdpsA, usp45N4 and hTFF3; PdpsA, usp45 and hTFF3 (sAGX0048);
  PpepV, usp45N4 and hTFF3; PpepV, usp45 and hTFF3;
  PsodA, usp45N4 and hTFF3; PsodA, usp45 and hTFF3;
  PhllA, usp45N4 and hTFF3 (sAGX0057); PhllA, usp45 and hTFF3;
(d) PdpsA, usp45N4 and hPYY; PdpsA, usp45 and hPYY (sAGX0048);
  PpepV, usp45N4 and hPYY; PpepV, usp45 and hPYY;
  PsodA, usp45N4 and hPYY; PsodA, usp45 and hPYY;
  PhllA, usp45N4 and hPYY (sAGX0057); PhllA, usp45 and hPYY; PhllA, usp45 and
  hPYY G9 (3-36) (sAGX0213);
(e) PdpsA, usp45N4 and GLP-1; PdpsA, usp45 and GLP-1;
  PpepV, usp45N4 and GLP-1; PpepV, usp45 and GLP-1;
  PsodA, usp45N4 and GLP-1; PsodA, usp45 and GLP-1;
  PhllA, usp45N4 and GLP-1; PhllA, usp45 and GLP-1;
(f) PdpsA, usp45N4 and GLP-2; PdpsA, usp45 and GLP-2;
  PpepV, usp45N4 and GLP-2; PpepV, usp45 and GLP-2;
  PsodA, usp45N4 and GLP-2; PsodA, usp45 and GLP-2;
  PhllA, usp45N4 and GLP-2; or PhllA, usp45 and GLP-2.

In a further preferred embodiment the present invention relates to In a further aspect the invention provides a method for recombinant expression of an expression product, preferably a polypeptide, of interest comprising:

a) culturing the host cell comprising a recombinant nucleic acid or vector of the invention, wherein the said one or more open reading frames encode the expression product, preferably polypeptide, of interest, and b) isolating the expression product, preferably polypeptide, of interest produced by the host cell in the said culturing.

A skilled person generally knows and can further optimise culturing conditions, e.g., temperature, presence and concentration of necessary nutrients, oxygenation, stirring, inoculation, etc. that allow for expression of the polypeptides in host cells, preferably host cells of the invention.

A skilled person also knows and can further optimise purification techniques for the isolation of the expression products, such as, preferably polypeptides, expressed by the said host cells. For example, suitable techniques of protein isolation may involve lysis of the host organism (e.g., when the polypeptide accumulates intracellularly) by, e.g., mechanical or enzymatic disruption of cell wall, and removal of cellular debris, or supernatant collection (e.g., when the polypeptides are secreted), removal of non-protein components, such as DNA and lipopolysaccharides, ammonium sulphate precipitation, size exclusion chromatography, e.g., to enrich for the desired protein, affinity chromatography, etc.

In a further aspect, the invention provides the use of the host cell transformed with the recombinant nucleic acid and/or the vector of the invention for the manufacture of a medicament for delivery of expression product(s), preferably polypeptide(s), encoded by the one or more open reading frames comprised within the said recombinant nucleic acid to a human or animal.

In a related aspect, the invention provides a method for delivery of a polypeptide encoded by the one or more open reading frames comprised within the recombinant nucleic acid of the invention to human or animal in need thereof, comprising administering to the said human or animal a therapeutically effective amount of host cells transformed with the said nucleic acid and/or vector of the invention. The animal may preferably be a mammal, such as, e.g., domestic animals, farm animals, zoo animals, sport animals, pet and experimental animals such as dogs, cats, guinea pigs, rabbits, rats, mice, horses, cattle, cows; primates such as apes, monkeys, orang-utans, and chimpanzees; canids such as dogs and wolves; felids such as cats, lions, and tigers; equids such as horses, donkeys, and zebras; food animals such as cows, pigs, and sheep; ungulates such as deer and giraffes; rodents such as mice, rats, hamsters and guinea pigs; and so on.

As used herein, the terms "treat" or "treatment" refer to both therapeutic treatment and prophylactic or preventative measures, wherein the object is to prevent or slow down (lessen) an undesired physiological change or disorder. A "human or animal in need of treatment" includes ones that would benefit from treatment of a given condition.

The term "therapeutically effective amount" refers to an amount of a therapeutic substance or composition effective to treat a disease or disorder in a subject, e.g., human or animal, i.e., to obtain a desired local or systemic effect and performance. By means of example, a therapeutically effective amount of bacteria may comprise at least 1 bacterium, or at least 10 bacteria, or at least $10^2$ bacteria, or at least $10^3$ bacteria, or at least $10^4$ bacteria, or at least $10^5$ bacteria, or at least $10^6$ bacteria, or at least $10^7$ bacteria, or at least $10^8$ bacteria, or at least $10^9$, or at least $10^{10}$, or at least $10^{11}$, or at least $10^{12}$, or at least $10^{13}$, or at least $10^{14}$, or at least $10^{15}$, or more host cells, e.g., bacteria, e.g., in a single or repeated dose.

The host cells of the present invention may be administered alone or in combination with one or more active compounds. The latter can be administered before, after or simultaneously with the administration of the said host cells.

A number of prior art disclosures on the delivery of antigens and/or therapeutically active polypeptides exist, and it shall be appreciated that such disclosures may be further advantageously modified with the strong promoters of the present invention. By means of example and not limitation, bacterial delivery of interleukins in particular IL-10 for treating colitis (e.g., see WO 00/23471), delivery of antigens as vaccines (e.g., WO 97/14806), delivery of GLP-2 and related analogs may be used to treat short bowel disease, Crohn's disease, osteoporosis and as adjuvant therapy during cancer chemotherapy, etc. Furthermore, bacterial delivery of trefoil peptides may be used to treat diseases of the alimentary canal (see, e.g., WO 01/02570). In particular, the use of trefoil proteins or peptides for treatment of disorders of and damage to the alimentary canal, including the mouth, oesophagus, stomach, and large and small intestine, as well as for the protection and treatment of tissues that lie outside the alimentary canal are described in WO 97/38712 and WO 92/14837. These proteins can be used either to treat lesions in these areas or to inhibit the formation of lesions. These lesions can be caused by: radiation therapy or chemotherapy for the treatment of cancer, any other drug including alcohol which damages the alimentary canal, accidental exposure to radiation or to a caustic substance, infection, a digestive disorder including but not limited to non-ulcer dyspepsia, gastritis, peptic or duodenal ulcer, gastric cancer, MALT lymphoma, Menetier's syndrome, gastro-oesophageal reflux disease, Crohn's disease, ulcerative colitis and acute colitis of chemical, bacterial or obscure origin. Trefoil peptides are particularly useful to treat acute colitis. Further therapeutic applications are envisioned using the promoters and host cells of the invention.

Further non-limiting examples of the types of diseases treatable in humans or animals by delivery of therapeutic polypeptides according to the invention include, but are not limited to, e.g., inflammatory bowel diseases including Crohn's disease and ulcerative colitis (treatable with, e.g., IL-Ira or IL-10 or trefoil peptides); autoimmune diseases, including but not limited to psoriasis, rheumatoid arthritis, lupus erythematosus (treatable with, e.g., IL-Ira or IL-10 or the relevant auto-antigen); allergic diseases including but not limited to asthma, food allergies, (treatable with the relevant allergen); celiac disease (treatable with gluten allergens); neurological disorders including, but not limited to Alzheimer's disease, Parkinson's disease and amyotrophic lateral sclerosis (treatable with, e.g., brain devated neurotropic factor and ciliary neurotropic factor); cancer (treatable with, e.g., IL-1, colony stimulating factors or interferon-W); osteoporosis (treatable with, e.g., transforming growth factor f3); diabetes (treatable with, e.g., insulin); cardiovascular disease (treatable with, e.g., tissue plasminogen activator); atherosclerosis (treatable with, e.g., cytokines and cytokine antagonists); hemophilia (treatable with, e.g., clotting factors); degenerative liver disease (treatable with, e.g., hepatocyte growth factor or interferon a); pulmonary diseases such as cystic fibrosis (treatable with, e.g., alpha antitrypsin); obesity; pathogen infections, e.g., viral or bacterial infections (treatable with any number of the above-mentioned compositions or antigens); etc.

The skilled reader shall appreciate that the herein specifically recited diseases are only exemplary and their recitation is in no way intended to confine the use of the reagents provided by the invention, e.g., the promoters, nucleic acids, vectors and host cells of the invention, to these particular diseases. Instead, a skilled reader understands that the reagents of the invention can be used to express in principle any expression products, preferably polypeptides, of interest, which may be of therapeutic relevance in not only the recited ones but also in various further diseases or conditions of humans and animals. Consequently, once a suitable expression product, preferably a polypeptide, e.g., an antigen and/or a non-vaccinogenic therapeutically active polypeptide, has been chosen or determined for a given ailment, a skilled person would be able to achieve its expression, isolation and/or delivery using the reagents of the invention.

The invention also contemplates treatment of diseases in other animals including dogs, horses, cats and birds. Diseases in dogs include but are not limited to canine distemper (paramyxovirus), canine hepatitis (adenovirus Cav-1), kennel cough or laryngotracheitis (adenovirus Cav-2), infectious canine enteritis (coronavirus) and haemorrhagic enteritis (parvovirus).

Diseases in cats include but are not limited to viral rhinotracheitis (herpesvirus), feline caliciviral disease (calicivirus), feline infectious peritonitis (parvovirus) and feline leukaemia (feline leukaemia virus). Other viral diseases in horses and birds are also contemplated as being treatable using the methods and compositions of the invention. To this purpose, the use of microorganisms expressing recombinant interferons will be particularly preferred.

In a further aspect, the invention thus also provides a pharmaceutical composition comprising the host cell transformed with the nucleic acid and/or the vector of the invention.

Preferably, such formulation comprise a therapeutically effective amount of the host cells of the invention and a pharmaceutically acceptable carrier, i.e., one or more pharmaceutically acceptable carrier substances and/or additives, e.g., buffers, carriers, excipients, stabilisers, etc.

The term "pharmaceutically acceptable" as used herein is consistent with the art and means compatible with the other ingredients of a pharmaceutical composition and not deleterious to the recipient thereof.

The recombinant host cells of the invention can be suspended in a pharmaceutical formulation for administration to the human or animal having the disease to be treated. Such pharmaceutical formulations include but are not limited to live host cells and a medium suitable for administration. The recombinant host cells may be lyophilized in the presence of common excipients such as lactose, other sugars, alkaline and/or alkali earth stearate, carbonate and/or sulphate (for example, magnesium stearate, sodium carbonate and sodium sulphate), kaolin, silica, flavorants and aromas.

Host cells so-lyophilized may be prepared in the form of capsules, tablets, granulates and powders, each of which may be administered by the oral route.

Alternatively, some recombinant bacteria may be prepared as aqueous suspensions in suitable media, or lyophilized bacteria may be suspended in a suitable medium just prior to use, such medium including the excipients referred to herein and other excipients such as glucose, glycine and sodium saccharinate.

For oral administration, gastroresistant oral dosage forms may be formulated, which dosage forms may also include compounds providing controlled release of the host cells and thereby provide controlled release of the desired protein encoded therein. For example, the oral dosage form (including tablets, pellets, granulates, powders) may be coated with a thin layer of excipient (usually polymers, cellulosic derivatives and/or lipophilic materials) that resists dissolution or disruption in the stomach, but not in the intestine, thereby allowing transit through the stomach in favour of disintegration, dissolution and absorption in the intestine.

The oral dosage form may be designed to allow slow release of the host cells and of the recombinant protein thereof, for instance as controlled release, sustained release, prolonged release, sustained action tablets or capsules. These dosage forms usually contain conventional and well known excipients, such as lipophilic, polymeric, cellulosic, insoluble, swellable excipients. Controlled release formulations may also be used for any other delivery sites including intestinal, colon, bioadhesion or sublingual delivery (i.e., dental mucosal delivery) and bronchial delivery. When the compositions of the invention are to be administered rectally or vaginally, pharmaceutical formulations may include suppositories and creams. In this instance, the host cells are suspended in a mixture of common excipients also including lipids. Each of the aforementioned formulations are well known in the art and are described, for example, in the following references: Hansel et al. (1990), Chien (1992), Prescott et al. (1989), and Cazzaniga et al. (1994).

Preferably, an enema formulation may be used for rectal administration. The term "enema" is used to cover liquid preparations intended for rectal use. The enema may be usually supplied in single-dose containers and contains one or more active substances dissolved or dispersed in water, glycerol or macrogols or other suitable solvents.

Thus, according the invention, in a preferred embodiment, recombinant host cells encoding a desired gene may be administered to the animal or human via mucosal, e.g., an oral, nasal, rectal, vaginal or bronchial route by any one of the state-of-the art formulations applicable to the specific route. Dosages of host cells for administration will vary depending upon any number of factors including the type of bacteria and the gene encoded thereby, the type and severity of the disease to be treated and the route of administration to be used.

Thus, precise dosages cannot be defined for each and every embodiment of the invention, but will be readily apparent to those skilled in the art once armed with the present invention. The dosage could be anyhow determined on a case by case way by measuring the serum level concentrations of the recombinant protein after administration of predetermined numbers of cells, using well known methods, such as those known as ELISA or Biacore (see examples). The analysis of the kinetic profile and half life of the delivered recombinant protein provides sufficient information to allow the determination of an effective dosage range for the transformed host cells.

In an embodiment, when the host cells express an antigen, the invention may thus also provide a vaccine.

The term "vaccine" identifies a pharmaceutically acceptable composition that, when administered in an effective amount to an animal or human subject, is capable of inducing antibodies to an immunogen comprised in the vaccine and/or elicits protective immunity in the subject.

The vaccine of the invention would comprise the host cells transformed with the nucleic acids or vectors of the invention and further optionally an excipient. Such vaccines may also comprise an adjuvant, i.e., a compound or composition that enhances the immune response to an antigen. Adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, and potentially useful pharmaceutically acceptable human adjuvants such as BCG (bacille Calmette-Guerin) and *Corynebacterium parvum*.

In further preferred embodiments the present invention relates to the use of a host cell as defined herein for the manufacture of a medicament for delivery of a polypeptide encoded by the said one or more open reading frames of the recombinant nucleic acid to a human or animal, preferably said polypeptide is an antigen and/or a non-vaccinogenic therapeutically active polypeptide, preferably hIL-10, GLP-2, GLP-1, TFF or hPYY as defined above. The present invention further relates to a pharmaceutical composition comprising the host cell as defined in herein. In addition, the present invention further relates to a host cell as defined in herein, for use as a medicament.

The invention is further illustrated with examples that are not to be considered limiting.

EXAMPLES

Materials Used in the Examples

GM17—M17 broth (Oxoid CM0817) prepared according to the manufacturer's instructions but without adding any sugars.
20% glucose (Merck 1.08337) sterilised by filtering (Stericup-GV 0.22 µm PVDF Millipore CGVU05RE).

GM17 broth: M17 supplemented with 0.5% glucose.
GM17T is GM17 supplemented with 200 μM thymidine (Sigma #T9250)
GM17E is GM17, supplemented with 5 μg/ml erythromycin (Sigma #E6376) by dilution from 25 mg/ml erythromycin in 96% ethanol stock solution.
BM9—10% casiton (Difco 225930) autoclave for 15 min at 121° C.
  0.5 M NaHCO$_3$ (Merck 1.06329) sterilised by filtering (Stericup-GV 0.22 μm PVDF Millipore CGVU05RE).
  0.5 M Na$_2$CO$_3$ (Merck 1.06392) sterilised by filtering (Stericup-GV 0.22 μm PVDF Millipore CGVU05RE).
  1 M MgSO$_4$ (Merck 1.05886) autoclave for 15 min at 121° C.
  100 mM CaCl$_2$ (Merck 1.02382) autoclave for 15 min at 121° C.
  10×M9 salts (Difco 248510) autoclave for 15 min at 121° C. Dilute 10× in sterile water to obtain M9 salts.
  10 ml BM9: add the different components in the same order as described below.
    1 ml 10×M9 salts
    500 μl 10% casiton
    250 μl 20% glucose
    7.75 ml water
    500 μl 0.5M NaHCO$_3$
    500 μl 0.5M Na$_2$CO$_3$
  Mix properly and add the following components:
    20 μl 1M MgSO$_4$
    10 μl 100 mM CaCl$_2$
BM9T is BM9 supplemented with 200 μM thymidine (Sigma #T9250)
BM9E is BM9, supplemented with 5 μg/ml erythromycin (Sigma #E6376) by dilution from 25 mg/ml erythromycin in 96% ethanol stock solution.
ELISA
IL10—BD OptEIA Human IL-10 ELISA kit II; Cat No: 550613; BD Biosciences; www.bdbiosciences.com
TFF-1—Sandwich ELISA
  coating antibody: TFF1 mouse monoclonal antibody (M02), clone 3H5 (Abnova Cat No: H00007031-M02)
  detecting antibody: polyclonal rabbit anti-hTFF1 (Alpha Diagnostics Cat No: TFF12-A; www.4adi.com)
  conjugate: anti rabbit-HRP (Southern Biotech Cat No: 4050-05; www.southernbiotech.com)
  substrate: TMB
TFF-3 Sandwich ELISA
  coating antibody: mouse monoclonal antibody 4408 against TFF-3 (R&D Systems Cat No: MAB4408; www.rndsystems.co)
  detecting antibody: in house biotinylated mouse monoclonal 15C6 against TFF-3 (Calbiochem Cat Noo: 585350; www.calbiochem.com)
  conjugate: Streptavidin-HRP (Cat No: 554066; BD Biosciences; www.bdbiosciences.com)
  substrate: TMB
PYY Commercial kit: Total Peptide YY (PYY) ELISA; Cat No: DSL-10-33600; Diagnostic System Laboratories, Inc.; www.dslabs.com
GLP-1 Commercial kit: Glucagon-like Peptide-1 (Active) ELISA kit; Cat. No: EGLP-35K; Linco Research; www.millipore.com Example 1

Isolation of Strong Promoters from *Lactococcus lactis*

Strongly expressed proteins were identified in *Lactococcus lactis* ssp. *lactis* MG1363 using the method of Antelmann et al. (2000).

Figure 2:
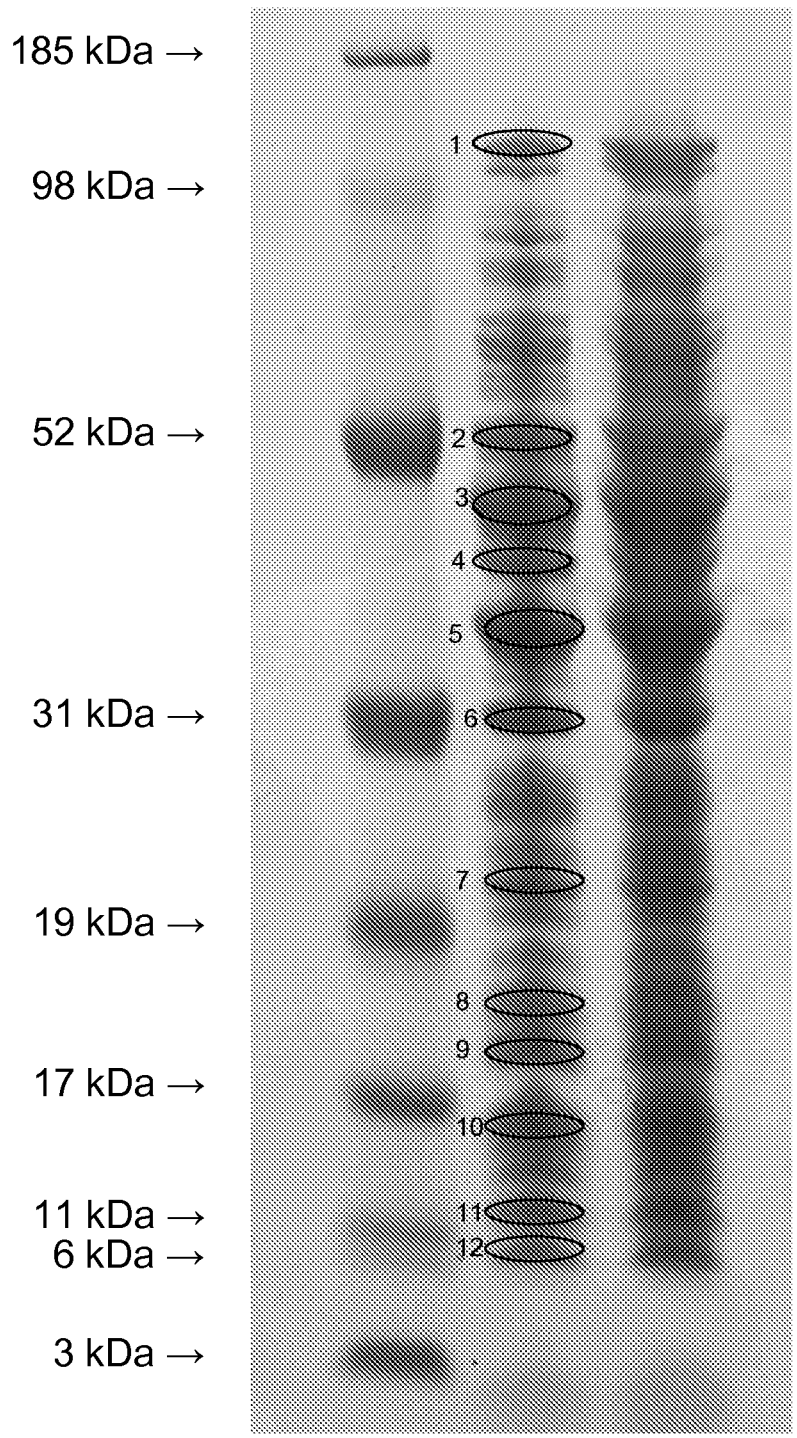
FIG. 2 illustrates electrophoretic separation of *Lactococcus lactis* MG1363 polypeptides.

Briefly, highly expressed proteins were identified by abundant protein spots in a 1 D gel (FIG. 2). The indicated protein bands were digested with trypsin and the peptide mixtures were analysed in LC-MS/MS mode in the ion trap mass spectrometer (Esquire HCT, Bruker). The spectra (only 250 MS/MS spectra per run were kept for data analysis) were analysed by MASCOT with the databank from *Lactococcus lactis* subsp. *cremoris* sk11 proteins (Genbank NC_008527). Peptides with a Mascot score above the identity threshold score are identified with a probability of 95%. The more peptides derived from the same protein, the more reliable the identification is.

This analysis produced a list of highly abundant proteins and the corresponding genes (Table 1 above, and FIG. 1). Based hereon, we identified and isolated sequences upstream of the indicated genes (SEQ ID NO: 1 to 54 and 157 to 180) with their own Shine Dalgarno (SD) sequences. For most promoters, this was done by PCR on *Lactococcus lactis* MG1363 chromosomal DNA. By example, primers used to amplify sequences of promoters corresponding to the genes listed under 1) to 30) above are shown in Table 2. Likewise, suitable primers can be selected on the basis of the available genomic information for promoters corresponding to genes listed under 31) to 53) above. Promoters for eno, tbp and lacE were also synthesized, using oligonucleotides (oligos in Table 3).

Example 2

Promoter Activity

Figure 3:
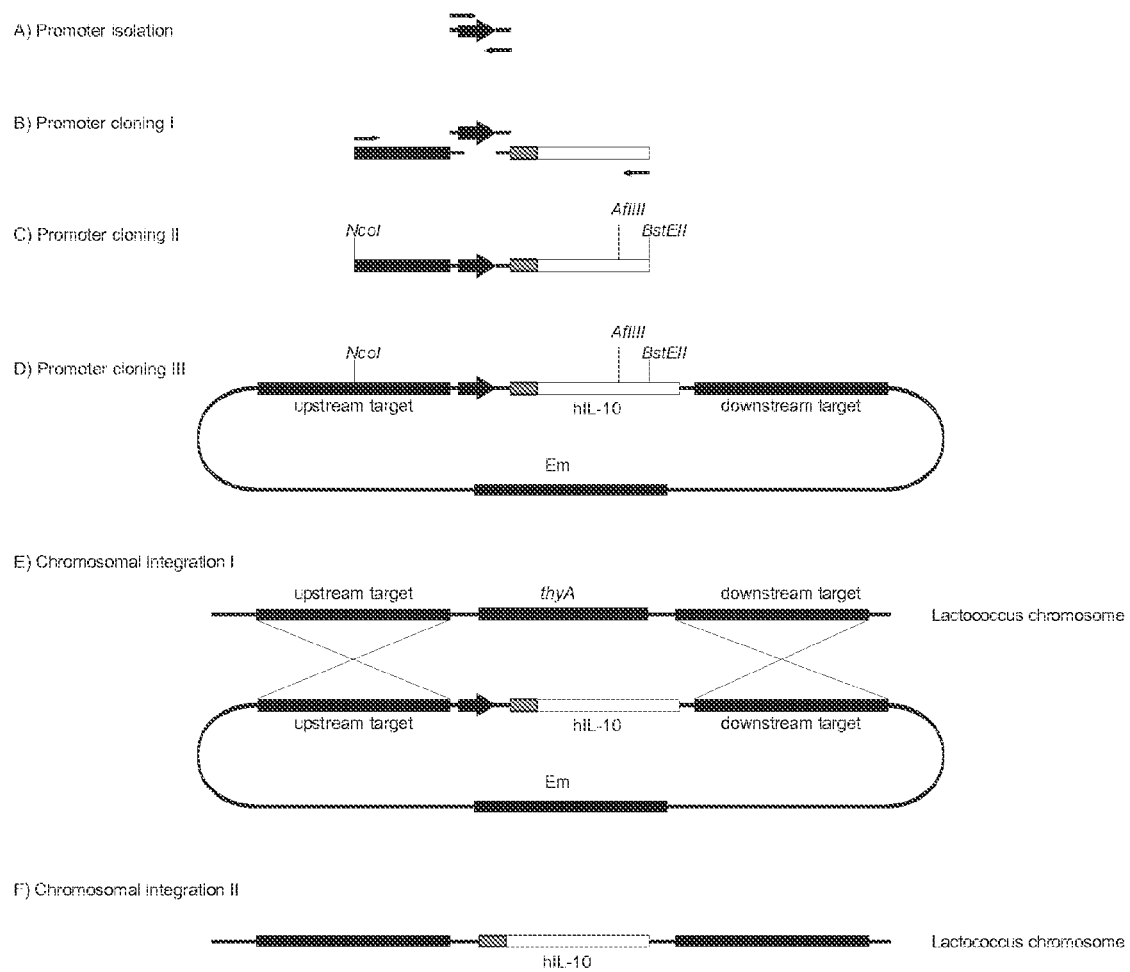
FIG. 3 illustrates a cloning strategy.

A strategy was devised that allowed the subcloning of the various promoters in front of the secretable hIL-10 gene (FIG. 3). The subcloning was performed in a way that the hIL-10 expression cassettes were flanked by target sequences. This structure enables double homologous recombination around the thyA gene and thus chromosomal integration, essentially as described in Steidler et al. 2003 supra and WO 02/090551.

Schematically, the strategy is outlined with reference to FIG. 3:
A) Using appropriate primers, promoters are isolated by PCR from *L. lactis* MG1363 chromosomal DNA; B) promoters are joined to relevant flanking regions (partial upstream target region, partial hIL-10) by annealing PCR; C and D) Joined products are subcloned in a conditionally non-replicative plasmid by using appropriately positioned restriction endonuclease sites (NcoI+AflIII or alternatively NcoI+BstEII). This completes both the upstream target region and hIL-10. E) Promoter constructs are introduced in *L. lactis* MG1363 by consecutive upstream and downstream recombination. Chromosomal integration is performed through a two step procedure. Following introduction of the non replicative plasmid in the parent strain *L. lactis* MG1363, a first homologous recombination at either the upstream or downstream target sequence can be selected for on erythromycin containing selective media. The second homologous recombination at the alternative target is screened for by the absence of thyA. F) Final chromosomal structure where thyA is replaced for by hIL-10.

Chromosomally integrated transgenes are assessed for expression levels of secretable hIL-10 (i.e., hIL-10 provided in-frame with a *Lactococcus* secretion signal sequence, e.g., usp45 or similar) in reference to other *Lactococcus* strains essentially as in Steidler et al. (2003); Self-containing *Lactococcus* strain WO 02/090551 and in brief described herein: the various *Lactococcus lactis* strains are streaked out to single colony and a preculture is prepared by inoculating 1 colony in GM17 (M17, Oxoid, Hampshire, UK, supplemented with 0.5% glucose) and incubation for 16 hrs at 30° C. These precultures are inoculated 1/25 in 5 ml GM and incubated for 4 hrs at 30° C. Cells are harvested by centrifugation and resuspended in 5 ml fresh BM9 (composition in Table 4). These cell suspensions are incubated for 3 hrs at 30° C. The bacterial cells are removed by centrifugation and supernatants are transferred to fresh tubes. The hIL-10 content of the supernatants is determined by ELISA and the hIL-10 proteins are visualized by analyzing the equivalent of 1 ml culture by western blot.

Even after repeated attempts and different cloning strategies it was not possible to sub-clone various promoter sequences. The successfully sub-cloned promoter sequences are summarized in Table 12.

Example 3

Promoter Strength

After identifying several promoters, we tested several promoter constructs in a further series of experiments. Moreover, in order to establish whether the promoter activity is independent from the reporter gene, we designed reporter constructs comprising the GLP-2 gene.

The human proglucagon gene (GenBank acc. nr. NM_002054) encodes a preproprotein that is cleaved into four distinct mature peptides, including glucagon-like peptide-2 (GLP-2). We designed a gene for h[Gly2]GLP-2 encoded in the preferential codon use of L. lactis. This gene encodes a mature human GLP-2 analog with an alanine to glycine substitution at position 2, which was shown reduce susceptibility to degradation by dipeptidyl peptidase-IV (Booth et al., 2004). The synthetic gene was assembled using state of the art methodology essentially as described by Stemmer et al. (1995), which is incorporated herein by reference.

The resulting fragment was fused to the usp45 secretion signal (van Asseldonk, et al., 1990). The fusion construct was placed downstream of a series of lactococcal promoters: P1 (Waterfield, et al., 1995), PthyA (thymidylate synthase promoter) and PhllA (promoter of bacterial nucleoid DNA-binding protein/DNA binding protein HU; SEQ ID NO: 28).

Figure 4:
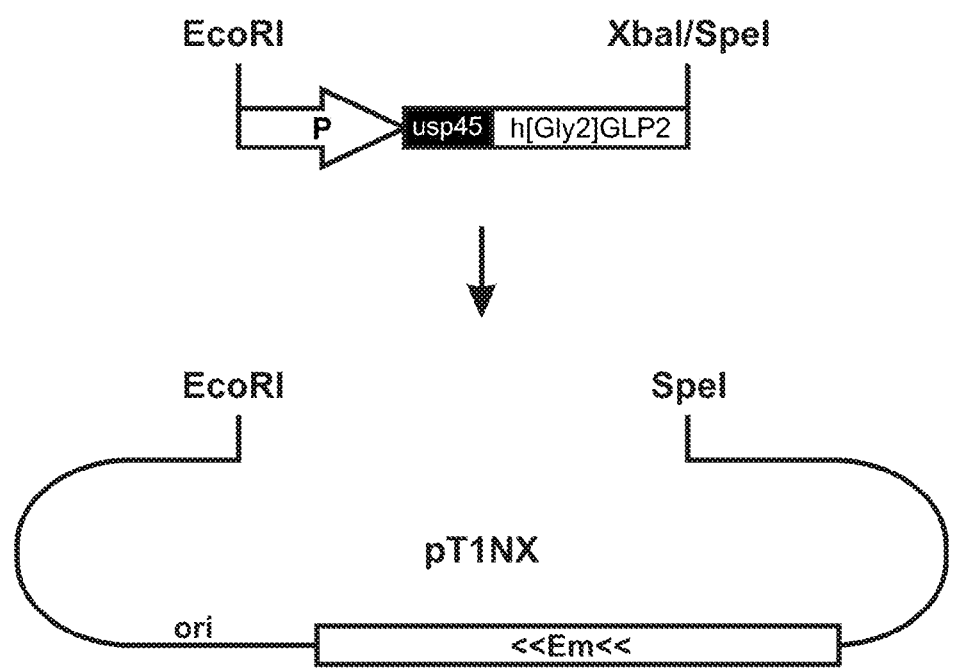
FIG. 4 Sub-cloning of promoter-Usp45-h[Gly2]GLP2 fusions. P stands for any of the following promoters: P1 (Waterfield, et al. 1995), PthyA (thymidylate synthase promoter) and PhllA (promoter of bacterial nucleoid DNA-binding protein/DNA binding protein HU); usp45 stands for the wild type usp45 secretion signal (van Asseldonk, et al. 1990) or mutant thereof, including Usp45 $N_4$ in which lysine at position 4 was substituted by asparagine; Em stands for erythromycin selection marker; on stands for origin of replication.

This strategy yielded fragments which could be subcloned as EcoRI-XbaI for P1 (pT1GLP2) or EcoRI-SpeI (all other constructs) fragments in the EcoRI-SpeI opened plasmid pT1NX (Steidler et al., 1998; FIG. 4).

An overview of the various plasmids is given in Table 5. All plasmids were sequence verified after which they were transformed to L. lactis MG1363 using the method by Gasson (1983).

GLP-2 expression and secretion was documented on protein extracts from the various strains obtained in parallel. In brief, saturated cultures were diluted 25-fold, grown in a suitably buffered growth medium and harvested at the end of log phase. Equivalents of 1 ml of culture were loaded on SDS-PAGE and analyzed by western blot. GLP-2 was detected by immunoblotting with a polyclonal rabbit anti-GLP-2 antibody (Abcam, Cambridge, UK). The secondary antibody was a goat anti-rabbit IgG (Southern Biotechnology Associates, Birmingham, Ala.) coupled to alkaline phosphatase. Enzymatic activity was revealed with NBT/BCIP substrate (Roche Diagnostics, Basel, Switzerland).

From our data it can be concluded that the PhllA promoter is extremely strong.

Example 4

Influence of the Signal Sequence

In order to control the expression levels, including production and secretion, we constructed a series of usp45 mutants, which were first tested in conjunction with the PhllA promoter of 28).

Figure 5:
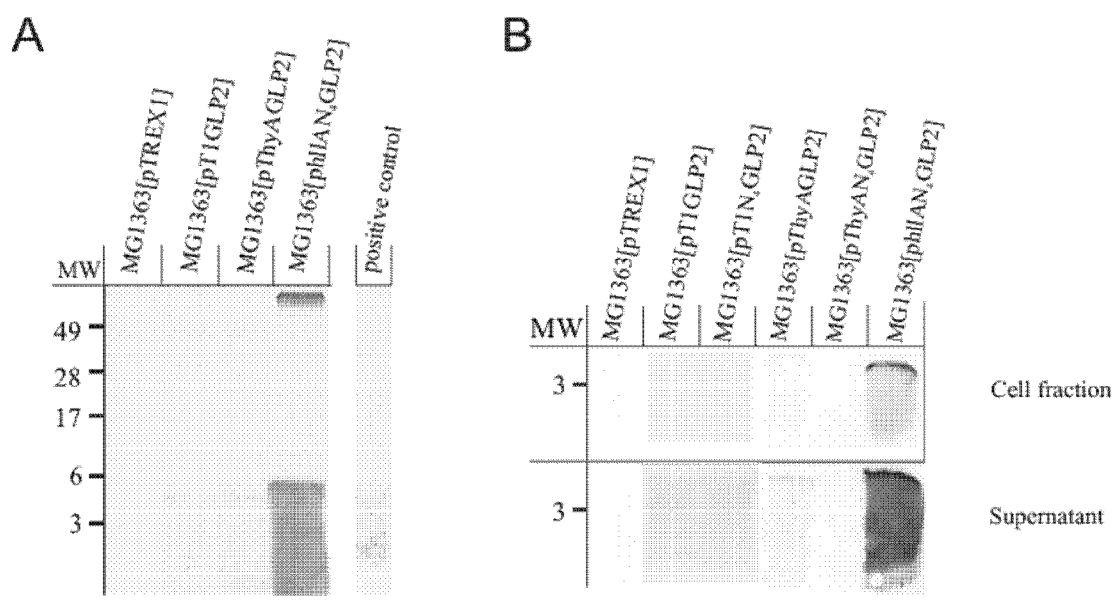
FIG. 5 Production and secretion of h[Gly2]GLP-2 by recombinant *L. lactis* strains revealed by anti-hGLP2 antibody. (A) Secretion of h[Gly2]GLP-2. 1 μg recombinant hGLP-2 was loaded as positive control. (B) Cellular production and secretion of h[Gly2]GLP-2. Each lane on the blot represents 1 ml of *L. lactis* cell fraction or culture supernatant obtained after three hours of growth. SeeBlue® Plus2 (Invitrogen) was used as molecular weight marker (MW).

Surprisingly, an usp45 mutant whereby lysine at position 4 was exchanged by asparagine (usp45 $N_4$), resulted in dramatically increased h[Gly2]GLP-2 production and secretion (PhllAN$_4$GLP2) relative to thyA-promoter and P1-promoter directed expression (FIG. 5A). Moreover, these transformants were exceedingly stable. The construct integrated into the genome of L. lactis gives also a substantially increased production and secretion. Expression of the reporter construct in Lactobacillus casei gives essentially the same results as in L. lactis.

Next, we introduced this mutation in usp45 downstream of the P1-promoter and the thyA-promoter, generating the plasmids pT1N$_4$GLP2 and pThyAN$_4$GLP2, respectively. Surprisingly, the mutation had little effect on h[Gly2]GLP-2 production regulated by the P1-promoter, but completely abolished h[Gly2]GLP-2 production under transcriptional control of thyA-promoter (FIG. 5B).

From these data it is obvious that the PhllA promoter in conjunction with the signal sequence uspN4 is exceedingly well suited for controlling expression of genes.

Example 5

Promoter Strength Tested by Human Interleukin-10 (hIL-10) Expression

We tested several promoter constructs in a series of experiments. Moreover, in order to establish whether the promoter activity is independent from the reporter gene, we designed reporter constructs in which expression cassettes were generated that contained the promoters under investigation, in front of the usp45 secretion signal (van Asseldonk et al., 1990) fused to a synthetic hIL-10 gene (see also Example 2). In this case, the fusion construct was placed downstream of a series of lactococcal promoters: PthyA (thymidylate synthase promoter, strains sAGX0005 and Thy12), PdpsA promoter (DNA-binding ferritin-like protein, SEQ ID NO: 3, sAGX0012), PpepV (Xaa-His dipeptidase promoter SEQ ID NO: 158, Strain sAGX0018), PsodA (superoxide dismutase promoter, SEQ ID NO: 20 sAGX0029) and PhllA (promoter of bacterial nucleoid DNA-binding protein/DNA binding protein HU; SEQ ID NO: 28, strain sAGX0037).

Figure 6:
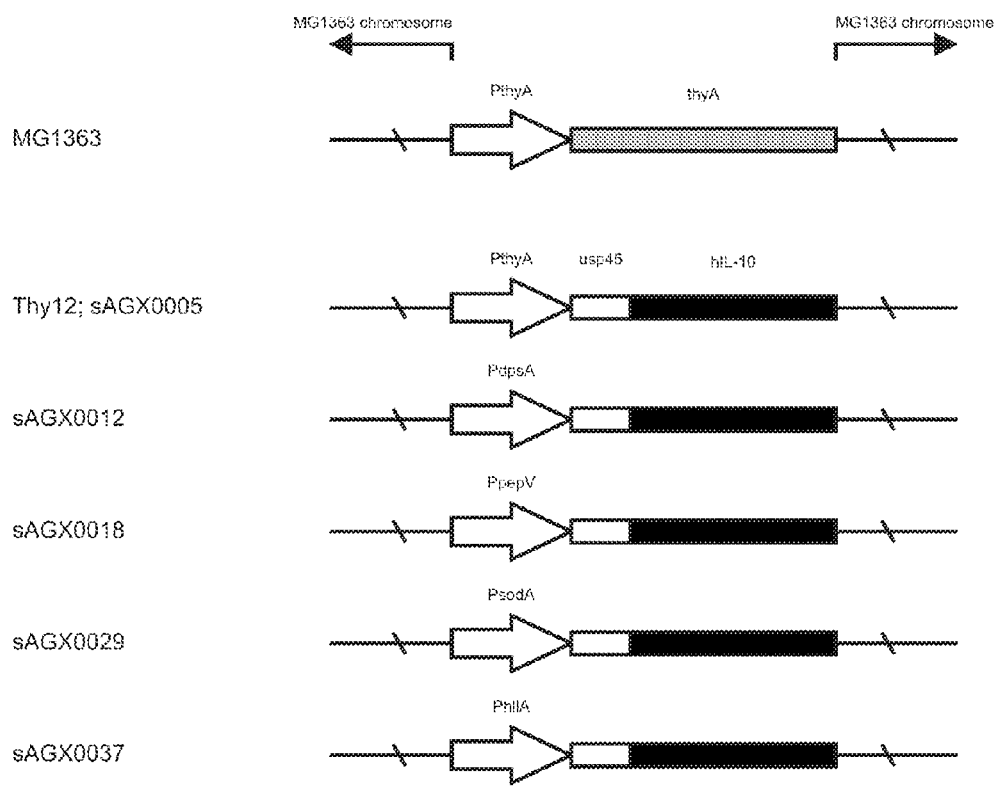
FIG. 6 Schematic comparison of *L. lactis* MG1363 and of the various hIL-10 expression strains used in this study. During construction, the hIL-10 expression cassettes are integrated in the *L. lactis* MG1363 chromosome by homologous recombination at identical sequences, both upstream as well as downstream of thyA and the hIL-10 expression cassettes respectively. Recombination points are schematically represented by \. This makes that all DNA sequences outside of the expression cassettes are identical for the above described strains. Genetic elements are not drawn to scale FIG. 7 Comparison of hIL-10 expression from PthyA (thymidylate synthase promoter, strains sAGX0005 and Thy12) with hIL-10 expression from (A) PdpsA promoter (DNA-binding ferritin-like protein, SEQ ID NO: 3, sAGX0012), (B) PpepV (Xaa-His dipeptidase promoter SEQ ID NO: 9 or 158, Strain sAGX0018), (C) PsodA (superoxide dismutase promoter, SEQ ID NO: 20 sAGX0029) and (D) PhllA (promoter of bacterial nucleoid DNA-binding protein/DNA binding protein HU; SEQ ID NO: 28, strain sAGX0037). "Promoter" indicates the promoter that is in front of the hIL-10 gene.

All expression cassettes were integrated in the thyA locus of L. lactis MG1363 chromosome by double homologous recombination, whereby the thyA gene was removed (a strategy similar to the one applied for the construction of Thy12 (Steidler et al., 2003) but without making use of the helper plasmid pVE6007, as shown in FIG. 3. This makes that all DNA sequences outside of the hIL-10 expression cassettes are identical. An overview of the structure and position of the hIL-10 expression cassettes in the various strains is given in FIG. 6. The hIL-10 expression cassettes (promoter, usp45 secretion signal, hIL-10) of the strains described here were sequence verified.

Figure 7:
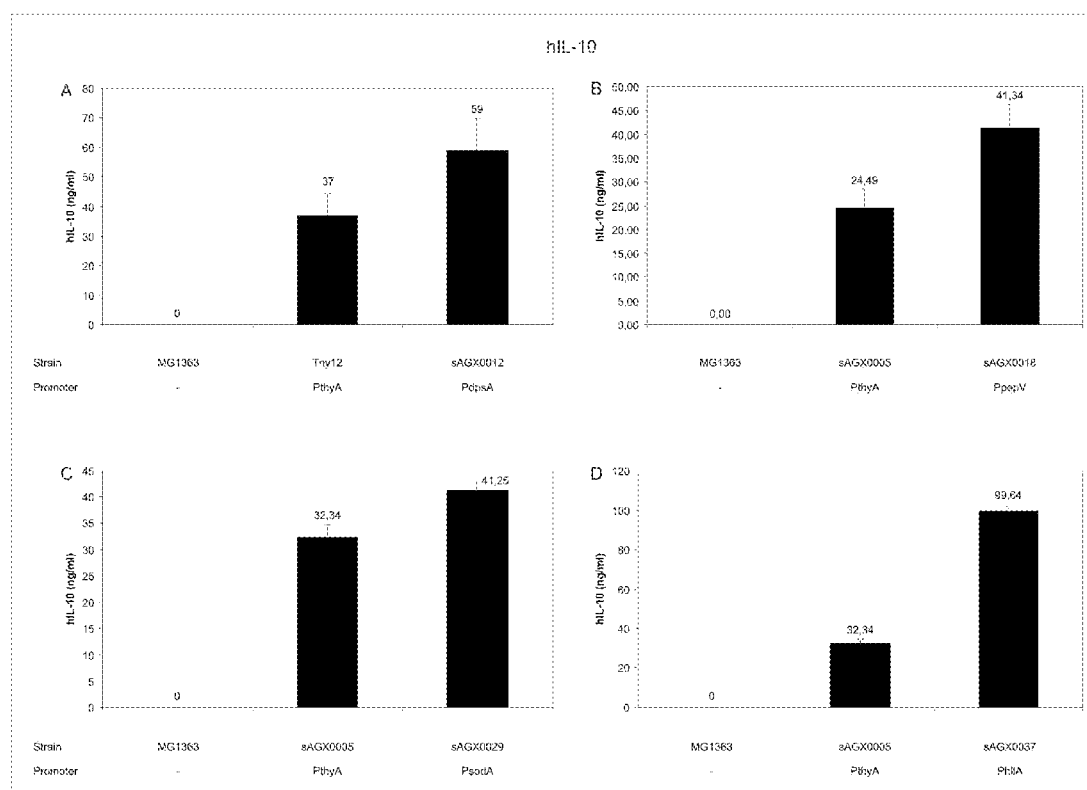

The various tested strains were streaked to single colony on solid agar GM17T plates. Single colonies were inoculated in GM17T and grown overnight to saturation. Appropriate dilutions of these cultures were pre-grown for 4 hours in GM17T. Bacteria were harvested by centrifugation and further incubated for 3 hours in buffered culture medium (BM9T). Bacteria were removed by centrifugation and from this cleared supernatant, samples were collected for analysis. Samples were analyzed by ELISA specific for hIL-10. Expression levels are given in FIG. 7. All data are given as the averages of three individual measurements. Relative promoter strength is given in Table 6.

Figure 8:
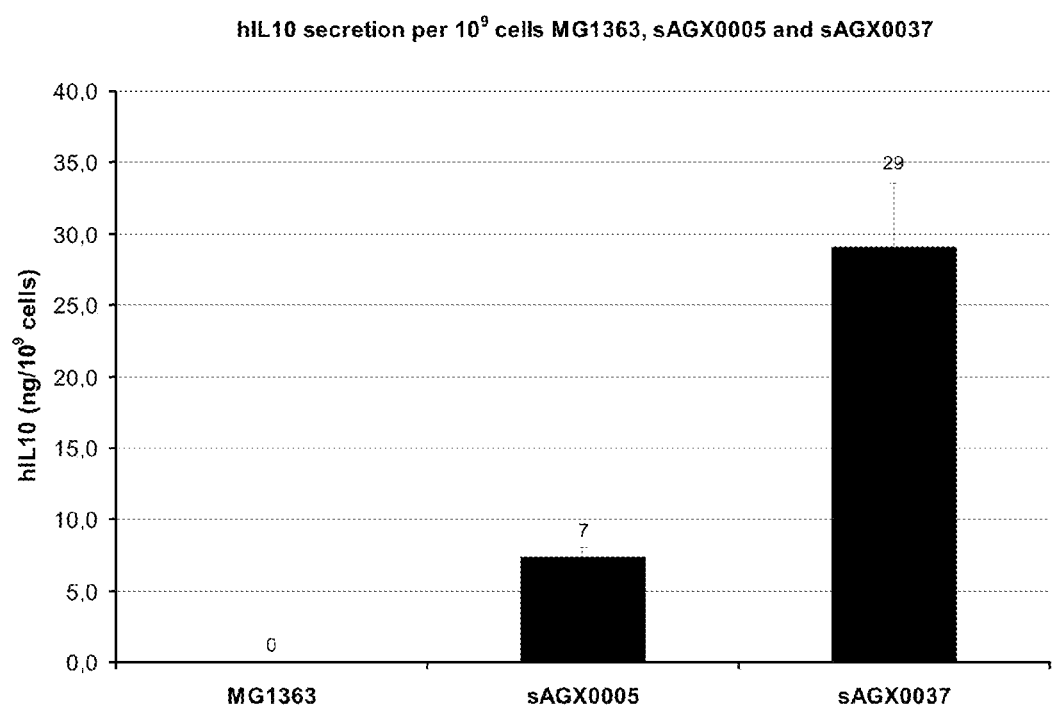
FIG. 8 Comparison of hIL-10 expression per $10^9$ MG1363, sAGX0005 and sAGX0037 cells FIG. 9 Schematic comparison of *L. lactis* MG1363 and of the various hTFF expression strains used in this study. During construction, the TFF expression cassettes are integrated in the *L. lactis* MG1363 chromosome by homologous recombination at identical sequences, both upstream as well as downstream of thyA and the TFF expression cassettes respectively. Recombination points are schematically represented by \. This makes that all DNA sequences outside of the expression cassettes are identical for the above described strains. Mutant usp45 is indicated by ★. Genetic elements are not drawn to scale.

To exclude the impact of different growth characteristics between strains, we determined colony forming units (CFU) at the end of an expression experiment as described above and calculated hIL-10 production per $10^9$ CFU for the various strains. This experiment shows that no substantially different growth rates are observed and that, as judged from hIL-10 expression, PhllA is approximately 4× stronger than PthyA (FIG. 8 and Table 7).

From our data it can be concluded that PdpsA, PpepV, PsodA and PhllA are extremely strong and very competent for directing expression of heterologous genes.

Example 6

Promoter Strength Tested by Human Trefoil Factor (TFF) Expression

Figure 9:
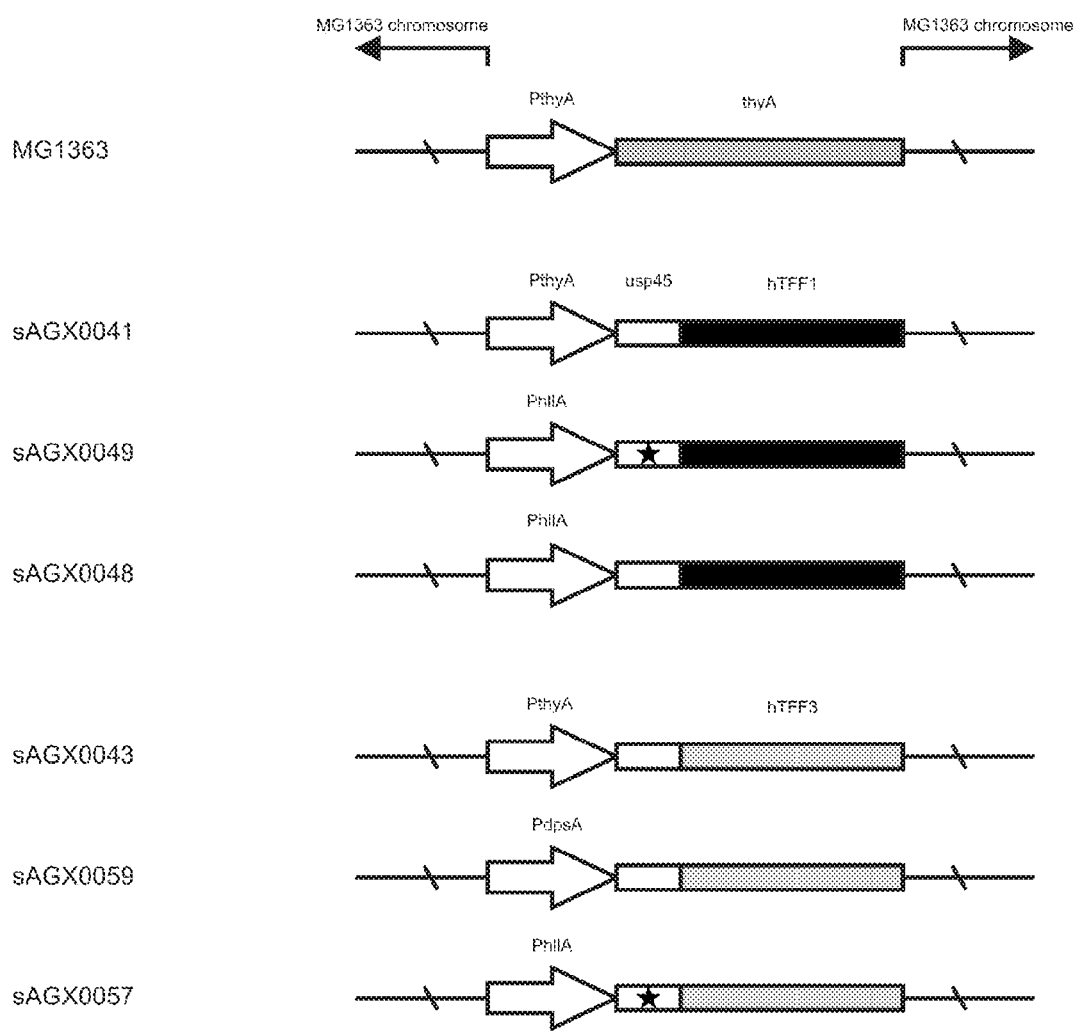

After identifying potentially strong promoters, we tested several promoter constructs in a further series of experiments. Moreover, in order to establish whether the promoter activity is independent from the reporter gene, we designed reporter constructs in which expression cassettes were generated that contained the promoters under investigation, in front of the wild type (wt) usp45 secretion signal (van Asseldonk et al., 1990) or mutant thereof (mut; including Usp45 $N_4$ in which lysine at position 4 was substituted by asparagine) fused to a synthetic hTFF1 or hTFF3 gene. The fusion constructs were placed downstream of a series of lactococcal promoters: PthyA (thymidylate synthase promoter, strains sAGX0041 and sAGX0043), PdpsA promoter (DNA-binding ferritin-like protein, SEQ ID NO: 3, strain sAGX0059), and PhllA (promoter of bacterial nucleoid DNA-binding protein/DNA binding protein HU; SEQ ID NO: 28, strains sAGX0048, sAGX0049 and sAGX0057). All expression cassettes were integrated in the thyA locus of *L. lactis* MG1363 chromosome by double homologous recombination, whereby the thyA gene was removed (a strategy similar to the one applied for the construction of Thy12 (Steidler et al., 2003) but without making use of the helper plasmid pVE6007, as shown in FIG. 3. This makes that all DNA sequences outside of the TFF expression cassettes are identical. An overview of the structure and position of the TFF expression cassettes in the various strains is given in FIG. 9 and Table 8. The TFF expression cassettes (promoter, secretion signal, TFF) of the strains described here were sequence verified.

The various tested strains were streaked to single colony on solid agar GM17T plates. Single colonies were inoculated in GM17T and grown overnight to saturation. Appropriate dilutions of these cultures were pre-grown for 4 hours in GM17T. Bacteria were harvested by centrifugation and further incubated for 3 hours in buffered culture medium (BM9T). Bacteria were removed by centrifugation and from this cleared supernatant, samples were collected for analysis. Samples were analyzed by ELISA specific for hTFF. Expression levels are given in FIG. 10. Samples from hTFF1 expresser strains were also analyzed by western blot specific for hTFF1 (FIG. 11). All data are given as the averages of three individual measurements. Relative promoter strength is given in Table 8.

Figure 10:
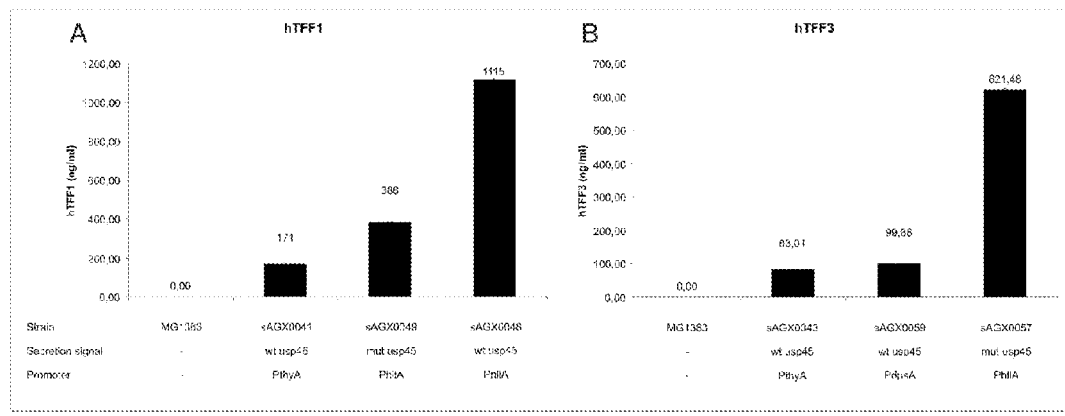
FIG. 10 Comparison of
(A) hTFF1 expression from PthyA (thymidylate synthase promoter) linked to the wild type (wt) usp45 secretion signal and hTFF1 (strain sAGX0041), PhllA (promoter of bacterial nucleoid DNA-binding protein/DNA binding protein HU; SEQ ID NO: 28) linked to the mutant (mut) usp45 secretion signal and hTFF1 (strain sAGX0049) or PhllA linked to the wt usp45 secretion signal and hTFF1 (strain sAGX0048).
(B) hTFF3 expression from PthyA (thymidylate synthase promoter) linked to the wt usp45 secretion signal and hTFF3 (strain sAGX0043), PdpsA promoter (DNA-binding ferritin-like protein, SEQ ID NO: 3) linked to the wt usp45 secretion signal and hTFF3 (sAGX0059) and PhllA linked to the mut usp45 secretion signal and hTFF3 (strain sAGX0057).

Consistent with Example 4, the data in FIG. 10 show that the Usp45 $N_4$ mutant is not responsible for an enhanced expression of hTFF3 by sAGX0057, but provides a further level of controlling expression.

The PdpsA, PpepV and PsodA placed in front of hTFF1 and hTFF3 expression constructs show also enhanced expression relative to PthyA.

From our data it can be concluded that PdpsA, PpepV, PsodA and PhllA are extremely strong and very competent for directing expression of heterologous genes.

Example 7

Promoter Strength Tested by Expression of Amino Acids 3-36 of Human Peptide YY Gly9 Variant (hPYY G9 (3-36))

After identifying potentially strong promoters, we tested several promoter constructs in a further series of experiments. Moreover, in order to establish whether the promoter activity is independent from the reporter gene, we designed reporter constructs in which expression cassettes were generated that contained the promoters under investigation, in front of the usp45 secretion signal (van Asseldonk et al., 1990) fused to a synthetic hPYY G9 (3-36) gene. The fusion construct was placed downstream of a series of lactococcal promoters: P1 (Waterfield et al., 1995) (plasmid pAGX0211); PthyA (thymidylate synthase promoter, plasmid pAGX0212), and PhllA (promoter of bacterial nucleoid DNA-binding protein/DNA binding protein HU; SEQ ID NO: 28, plasmid pAGX0213). All expression cassettes were inserted as EcoRI-SpeI fragments in the plasmid pT1NX (Schotte et al., 2000). This makes that all DNA sequences outside of the expression cassettes, including origin of replication and erythromycin resistance, are identical for the above plasmids. An overview of the structure of the various expression plasmids is given in FIG. 12 and Table 9. The hPYY expression cassettes (promoter, usp45 secretion signal, PYY) of the strains described here were sequence verified.

The empty expression vector pT1 NX as well as all hPYY G9 (3-36) expression plasmids were transformed to *L. lactis* MG1363. The resulting strains were streaked to single colony on solid agar GM17E plates. Single colonies were inoculated in GM17E and grown overnight to saturation. Appropriate dilutions of these cultures were pre-grown for 4 hours in GM17E. Bacteria were harvested by centrifugation and further incubated for 3 hours in buffered culture medium (BM9E). Bacteria were removed by centrifugation and from this cleared supernatant, samples were collected for analysis. Samples were analyzed by ELISA specific for hPYY. Expression levels are given in FIG. 13. Relative promoter strength is given in Table 9.

The PdpsA, PpepV and PsodA placed in front of the usp45 secretion signal (van Asseldonk et al., 1990) fused to a synthetic hPYY G9 (3-36) gene, show also enhanced expression relative to PthyA directed expression.

From our data it can be concluded that PdpsA, PpepV, PsodA and PhllA are extremely strong and very competent for directing expression of heterologous genes.

Example 8

Promoter Strength Tested by Expression of Amino Acids 7-36 of Human Glucagon-Like Peptide-1 Gly8 Variant (hGLP-1 G8 (7-36))

After identifying potentially strong promoters, we tested several promoter constructs in a further series of experiments. Moreover, in order to establish whether the promoter activity is independent from the reporter gene, we designed reporter constructs in which expression cassettes were generated that contained the promoters under investigation, in front of the usp45 secretion signal (van Asseldonk et al. 1990) fused to a synthetic hGLP-1 G8 (7-36) gene. The GLP-1 Gly8 variant shows reduced susceptibility towards proteolytic cleavage by dipeptidyl peptidase VI (Deacon et al., 1998) The fusion construct was placed downstream of two lactococcal promoters: PthyA (thymidylate synthase promoter, plasmid pAGX0233), and PhllA (promoter of bacterial nucleoid DNA-binding protein/DNA binding protein HU; SEQ ID NO: 28, plasmid pAGX0234). All expression cassettes were inserted as EcoRI-SpeI fragments in the plasmid pT1NX (Schotte et al., 2000). This makes that all DNA sequences outside of the expression cassettes, including origin of replication and erythromycin resistance, are identical for the above plasmids. An overview of the structure of the various expression plasmids is given in FIG. 14 and Table 10. The GLP-1 Gly8 expression cassettes (promoter, usp45 secretion signal, GLP-1 Gly8) of the strains described here were sequence verified. The empty expression vector pT1NX as well as all hGLP-1 G8 (7-36) expression plasmids were transformed to L. lactis MG1363. The resulting strains were streaked to single colony on solid agar GM17E plates. Single colonies were inoculated in GM17E and grown overnight to saturation. Appropriate dilutions of these cultures were pre-grown for 4 hours in GM17E. Bacteria were harvested by centrifugation and further incubated for 3 hours in buffered culture medium (BM9E). Bacteria were removed by centrifugation and from this cleared supernatant, samples were collected for analysis. Samples were analyzed by ELISA specific for hGLP-1. Expression levels are given in FIG. 15. Relative promoter strength is given in Table 10.

Example 9

Promoter Strength Tested by Human Interleukin-10 (hIL-10) Expression

We tested several promoter constructs in a further series of experiments. Moreover, in order to establish whether the promoter activity is independent from the reporter gene, we designed reporter constructs in which expression cassettes were generated that contained the promoters under investigation, in front of the usp45 secretion signal (van Asseldonk et al. 1990) fused to a synthetic hIL-10 gene. The fusion construct was placed downstream of a series of lactococcal promoters (FIG. 16 and Table 11).

All expression cassettes were integrated in the thyA locus of L. lactis MG1363 chromosome by double homologous recombination, whereby the thyA gene was removed (a strategy similar to the one applied for the construction of Thy12 (Steidler et al., 2003) but without making use of the helper plasmid pVE6007). This makes that all DNA sequences outside of the hIL-10 expression cassettes are identical. A generalized overview of the structure and position of the hIL-10 expression cassettes present in the various strains (commonly designated "sAGX00xx") is depicted in FIG. 16. The hIL-10 expression cassettes (promoter, usp45 secretion signal, hIL-10) of the strains described here were sequence verified.

The various tested strains were streaked to single colony on solid agar GM17T plates. Single colonies were inoculated in GM17T and grown overnight to saturation. Appropriate dilutions of these cultures were pre-grown for 4 hours in GM17T. Bacteria were harvested by centrifugation and further incubated for 3 hours in buffered culture medium (BM9T). Bacteria were removed by centrifugation and from this cleared supernatant, samples were collected for analysis. Samples were analyzed by ELISA specific for hIL-10. Expression levels are given in FIG. 17. All data are given as the averages of three individual measurements. Relative promoter strength is given in Table 11.

In contrast to projected proteomic and transcriptome analysis, the strength and competence of a particular promoter directing expression of heterologous genes remained unexpected.

TABLE 1

| Gene Number | Gene ID MG1363 | Gene ID SK11 | Corresponding protein as annotated in MG1363 | Gene name MG1363 | Gene name SK11 | Exemplary promoter sequence (SEQ ID NO) |
|---|---|---|---|---|---|---|
| 1) | 4798573 | 4432638 | DNA-directed RNA polymerase, beta' subunit/160 kD subunit | rpoC | LACR_1980 | 1 |
| 2) | 4798827 | 4432639 | DNA-directed RNA polymerase, beta subunit/140 kD subunit | rpoB | rpoB | 2, 157 |
| 3) | 4793207 | 4434445 | non-heme iron-binding ferritin | dpsA | LACR_2311 | 3 |
| 4) | 4797791 | 4433214 | pyruvate kinase | pyk | LACR_1456 | 4 |
| 5) | 4798062 | 4433965 | glutamyl-tRNA synthetases | gltX | gltX | 5 |
| 6) | 4797432 | 4433058 | phosphopyruvate hydratase | eno | eno | 6 |
| 7) | 4797464 | 4433379 | glutamine synthetase | glnA | LACR_2512 | 7 |
| 8) | 4797312 | 4433380 | glutamine synthetase repressor | glnR | LACR_2513 | 8 |
| 9) | 4798910 | 4432071 | dipeptidase PepV | pepV | LACR_0908 | 9, 158 |
| 10) | 4797781 | 4433907 | F0F1-type ATP synthase beta subunit (ATP synthase F1 beta subunit) | atpD | LACR_1933 | 10 |
| 11) | 4797899 | 4433798 | 3-phosphoglycerate kinase | pgk | pgk | 11 |
| 12) | 4797877 | 4432135 | glyceraldehyde-3-phosphate dehydrogenase | gapB | LACR_2555 | 12, 159 |
| 13) | 4798785 | 4432332 | acetate kinase | ackA1 | LACR_2295 | 13, 160 |
| 14) | 4796577 | 4432366 | 3-oxoacyl-(acyl-carrier-protein) synthase II | fabF | LACR_0825 | 14 |
| 15) | 4797984 | 4432365 | 3-ketoacyl-(acyl-carrier-protein) reductase | fabG fabG1 | fabG | 15, 161 |
| 16) | 4797865 | 4434231 | DNA-directed RNA polymerase, alpha subunit/40 kD subunit | rpoA | LACR_2375 | 16 |
| 17) | 4798484 | 4432446 | Proline dipeptidase | pepQ | LACR_1813 | 17, 162 |
| 18) | 4798307 | 4434211 | fructose-bisphosphate aldolase | fbaA | LACR_2168 | 18, 163 |
| 19) | 4798643 | 4433237 | 30S ribosomal protein S4 | rpsD | rpsD | 19 |
| 20) | 4796682 | 4433052 | superoxide dismutase | sodA | LACR_0458 | 20 |

TABLE 1-continued

| Gene Number | Gene ID MG1363 | Gene ID SK11 | Corresponding protein as annotated in MG1363 | Gene name MG1363 | Gene name SK11 | Exemplary promoter sequence (SEQ ID NO) |
|---|---|---|---|---|---|---|
| 21) | 4799037 (rpsL) | 4433371 (rpsL) | 30S ribosomal protein S12 (rpsL) and 30S ribosomal protein S7 (rpsG/LACR_2596)) | rpsL | rpsL | 21, 164 |
|  | 4797556 (rpsG) | 4433370 (LACR_2596) |  | rpsG | LACR_2596 |  |
| 22) | 4799022 (rplR) | 4433741 (LACR_2385) | 50S ribosomal protein L18 (rplR/LACR_2385) and 30S protein S5 (rpsE/LACR_2384) and 50S ribosomal protein L30/L7E (rpmD) | rplR | LACR_2385 | 22, 165 |
|  | 4798090 (rpsE) | 4433740 (LACR_2384) |  | rpsE | LACR_2384 |  |
|  | 4797873 (rpmD) | 4433739 (rpmD) |  | rpmD | rpmD |  |
| 23) | 4798265 | 4434424 | S-ribosylhomocysteinase | luxS | LACR_0270 | 23 |
| 24) | 4798969 | 4432986 | 50S ribosomal protein L19 | rplS | rplS | 24 |
| 25) | 4798819 | 4434232 | 30S ribosomal protein S11 | rpsK | LACR_2376 | 25, 168 154) |
| 26) | 4797191 | 4433166 | 50S ribosomal protein L10 | rplJ | rplJ | 26, 169 |
| 27) | 4797926 | 4433165 | 50S ribosomal protein L7/L12 | rplL | LACR_1386 | 27, 170 |
| 28) | 4797353 | 4433712 | HU-like DNA-binding protein | hllA | LACR_0525 (hup) | 28 |
| 29) | 4797103 | 4433888 | 50S ribosomal protein L28 | rpmB | LACR_0198 | 29 |
| 30) | 4797109 | 4433007 | phosphotransferase system IIB component | ptcB | LACR_0465 | 30, 170 |
| 31) | 4798114 | 4432141 | F0F1-type ATP synthase alpha subunit | atpA | LACR_1935 | 31, 172 |
| 32) | 4797024 | 4433016 | multiple sugar-binding transport ATP-binding protein | msmK | LACR_0474 | 32, 173 |
| 33) | 4798130 | 4434638 | acetoin dehydrogenase complex E1 component alpha subunit (acoA) | pdhA | LACR_0051 | 33, 174 |
| 34) | 4797264 | 4432815 | cell division protein | ftsA | LACR_2057 | 34, 175 |
| 35) | 4798554 | 4434372 | UDP-galactopyranose mutase | glf1 | LACR_0219 | 35 |
| 36) | 4796852 | 4433097 | glutamyl aminopeptidase | pepA | LACR_0433 | 36 |
| 37) | 4798279 | 4433301 | predicted dehydrogenase related protein | llmg_0272 | LACR_0268 | 37, 176 |
| 38) | 4797347 | 4432587 | 30S ribosomal protein S2 | rpsB | rpsB | 38, 177 |
| 39) | 4798807 | 4433762 | translation initiation factor 3 (IF-3) | infC | LACR_0436 | 39, 178 |
| 40) | 4798524 (rplD) | 4433828 (rplD) | 50S ribosomal protein L4 (rplD) and 50S ribosomal protein L23 (rplW) and 50S ribosomal protein L2 (rplB) | rplD | rplD | 40, 179 |
|  | 4798431 (rplW) | 4433827 (rplW) |  | rplW | rplW |  |
|  | 4798645 (rplB) | 4433826 (rplB) |  | rplB | rplB |  |
| 41) | 4797346 | 4433100 | Phenylalanyl-tRNA synthetase beta chain | pheT | LACR_0436 | 41 |
| 42) | 4799077 | 4433204 | transcription elongation factor GreA | greA | LACR_0660 | 42 43 |
| 43) | 4796752 | 4432931 | protease subunit of ATP-dependent Clp protease | clpP | clpP | 44 |
| 44) | 4797213 | 4433738 | 50S ribosomal protein L15 | rplO | LACR_2382 | 45 |
| 45) | 4798439 | 4433280 | 50S ribosomal protein L11 | rplK | rplK | 46 |
| 46) | 4797933 | 4433743 | 30S ribosomal protein S8 | rpsH | LACR_2387 | 47 |
| 47) | 4797761 | 4432457 | 50S ribosomal protein L21 | rplU | rpLU | 48 |
| 48) | 4798259 | 4433733 | 30S ribosomal protein S13 | rpsM | rpsM | 49 |
| 49) | 4797839 (rpsS) | 4433825 (rpsS) | 30S ribosomal protein S19 (rpsS) and 50Sribosomal protein L22 (rplV) and 50S ribosomal protein L16 (rplP) and 50S ribosomal ribosomal protein L22 (rplV) | rpsS | rpsS | 50 |
|  | 4798792 (rplV) | 4433824 (rplV) |  | rplV | rplV |  |
|  | 4798472 (rplP) | 4433822 (rplP) |  | rplP | rplP |  |
|  | 4799034 (rplN) | 4433748 (LACR_2392) | ribosomal protein L14 (rplN) | rplN | LACR_2392 |  |
| 50) | 4798419 | 4433829 | 30S ribosomal protein S10 | rpsJ | LACR_2402 | 51 |
| 51) | 4798582 | 4433103 | co-chaperonin GroES | groES | groES | 52, 180 |
| 52) | 4797891 | 4433747 | 50S ribosomal protein L24 | rplX | rplX | 53 |
| 53) | 4797916 | 4432598 | putative Hollyday junction resolvase (MG1363) | llmg_0151 | LACR_0137 | 54 |

TABLE 2

| Promoter sequence (SEQ ID No Table 1) | Amplified with primers Forward (SEQ ID NO) Reverse (SEQ ID NO) |
|---|---|
| 1 | GTTCAGAAACTGCCTGATGGATTTTGTAATTAATATTTT GAGATTTATTTACTGAC (55) |
|  | CATTAAAATAGCTGAGATAATCTTTTTTTTCAATTCTTT CTCCACTTCTAATAAATTTAAC (56) |
| 2 | GTTCAGAAACTGCCTGATGGGCTAGATAAGCCTTGAAAA TTTC (57) |
|  | CATTAAAATAGCTGAGATAATCTTTTTTTTCAAGTGTTT TCTCCTCTATTTTTTAG (58) |
| 3 | GGTTCAGAAACTGCCTGATGGACTAATCTATACGAAAAT TGATTTTGAATG (59) |
|  | CATTAAAATAGCTGAGATAATCTTTTTTTTCATAACTAA CCTCCATTTTTTAAATATTA (60) |

TABLE 2-continued

| Promoter sequence (SEQ ID No Table 1) | Amplified with primers Forward (SEQ ID NO) Reverse (SEQ ID NO) |
|---|---|
| 4 | GTTCAGAAACTGCCTGATGGCTAAGTTACTGCAAATCTG TTTC (61)<br>CATTAAAATAGCTGAGATAATCTTTTTTTTCATTTTGTG TTTTTCTCCTATAATG (62) |
| 5 | GTTCAGAAACTGCCTGATGGGATAAATTTCACTGACGCA AGC (63)<br>CATTAAAATAGCTGAGATAATCTTTTTTTTCATTTTAAT CCAATTCTCCTCATTG (64) |
| 6 | GTTCAGAAACTGCCTGATGGAAATTAAGGATAGATTTTT TCTATCCTTTTTC (65)<br>CATTAAAATAGCTGAGATAATCTTTTTTTTCATTTTAGT CTCCTTATTATTTTAAGTGCG (66) |
| 7 | GTTCAGAAACTGCCTGATGGATTTGGTTGACATAATTTG TCAAG (67)<br>CATTAAAATAGCTGAGATAATCTTTTTTTTCATGCTTTA CTCTCCTAGTTAAATTTTC (68) |
| 8 | GTTCAGAAACTGCCTGATGGCAAATAAAAAGAACTGATG TGAGAAAATC (69)<br>CATTAAAATAGCTGAGATAATCTTTTTTTTCATAGAGCG TCTTAATTCACG (70) |
| 9 | GTTCAGAAACTGCCTGATGGGATATTATCTTTATCCTCC TTATATATAATC (71)<br>CATTAAAATAGCTGAGATAATCTTTTTTTTCATAATCTT CTCCTTGAAGTAG (72) |
| 10 | GTTCAGAAACTGCCTGATGGTTACTGTCAAACATTATTC TCAATGTTAC (73)<br>CATTAAAATAGCTGAGATAATCTTTTTTTTCATTTTTAA GCTAATCAGTAAAAATTTAC (74) |
| 11 | GTTCAGAAACTGCCTGATGGGTTGCTTAGCAAAGCT C (75)<br>CATTAAAATAGCTGAGATAATCTTTTTTTTCATTTGGAA AAATTCTCCTTATAAG (76) |
| 12 | GTTCAGAAACTGCCTGATGGGAATAAAAATTACTGTCAG CCTGC (77)<br>CATTAAAATAGCTGAGATAATCTTTTTTTTCATTAGTAG TTTCCTCCTTATAGGG (78) |
| 13 | GTTCAGAAACTGCCTGATGGAAATAAAAAATTATTGGCT AGTCTGTCAG (79)<br>CATTAAAATAGCTGAGATAATCTTTTTTTTCATGTTTAA TAAACCTTCCTTGAATTTG (80) |
| 14 | GTTCAGAAACTGCCTGATGGATTGCTCATTTATAAATTT TGAAATTAAGAAGG (81)<br>CATTAAAATAGCTGAGATAATCTTTTTTTTCATATTTTT ATCCTTCTTAATTTCAAAATTTATAAATG (82) |
| 15 | GTTCAGAAACTGCCTGATGGGGAGAAAGGAATTGAGTTC G (83)<br>CATTAAAATAGCTGAGATAATCTTTTTTTTCATTATTTA TAAGATGTGAGCCC (84) |
| 16 | GTTCAGAAACTGCCTGATGGTTAGTCACTCTTGTCACTA ATCAC (85)<br>CATTAAAATAGCTGAGATAATCTTTTTTTTCATGTATGT TCTCCTCTAAAGCG (86) |
| 17 | GTTCAGAAACTGCCTGATGGCTATCCTCTTTCTTTTCTT TTTATTCATAG (87)<br>CATTAAAATAGCTGAGATAATCTTTTTTTTCAAATGGT TCCTCCAATATTAATG (88) |
| 18 | GTTCAGAAACTGCCTGATGGGATAAGATTAATAGTTTTA GCTATTAATC (89)<br>CATTAAAATAGCTGAGATAATCTTTTTTTTCATTTCAAA ATTCCTCCGAATA (90) |
| 19 | GTTCAGAAACTGCCTGATGGGCTTTTCTTGACAAAATAA GGATTTTTG (91)<br>CATTAAAATAGCTGAGATAATCTTTTTTTTCATAATTTA TGTCCTCCAAATATTTTATTTG (92) |
| 20 | GTTCAGAAACTGCCTGATGGAAATCAAATCATTTGGCAA TGATTTC (93)<br>CATTAAAATAGCTGAGATAATCTTTTTTTTCATAGTAAT TCTCCTTTTAAGATGTG (94) |
| 21 | GTTCAGAAACTGCCTGATGGCTCAAAATATAAGCTTAAT CGC (95)<br>CATTAAAATAGCTGAGATAATCTTTTTTTTCATTTTACT GTCTGCTTTTTATATTTTCC (96) |
| 22 | GTTCAGAAACTGCCTGATGGGCGTCGGCTTGCG (97)<br>CATTAAAATAGCTGAGATAATCTTTTTTTTCACAATTCT ACCTCTATATTATTTAAATTTC (98) |
| 23 | GTTCAGAAACTGCCTGATGGCTACAAACGCTTTACTGAA AACG (99)<br>CATTAAAATAGCTGAGATAATCTTTTTTTTCATAAAATA TATGATACAAAACTCAGC (100) |
| 24 | GTTCAGAAACTGCCTGATGGCAGCATTAAGATAAAGAGT TATGAGC (101)<br>CATTAAAATAGCTGAGATAATCTTTTTTTTCATTTTTTT CTCCTCTTGCCC (102) |
| 25 | GTTCAGAAACTGCCTGATGGTAAATCATAAAACCTCTGT CAGAGG (103)<br>CATTAAAATAGCTGAGATAATCTTTTTTTTCAAGCAAAA GTACCTCCTTAAAAATTTC (104) |
| 26 | GTTCAGAAACTGCCTGATGGAATAGAAGATATTTTTCAG TAGATATAG (105)<br>CATTAAAATAGCTGAGATAATCTTTTTTTTCATTTTTTT ACCTCCATTTTATTTTGG (106) |
| 27 | GTTCAGAAACTGCCTGATGGTTATAAGCAACATCACTTA TATCGG (107)<br>CATTAAAATAGCTGAGATAATCTTTTTTTTCATTTTAAT ATTCTCCTATTAATTTTTAG (108) |
| 28 | GTTCAGAAACTGCCTGATGGAAAACGCCTTAAAATGGCA TTTTG (109)<br>CATTAAAATAGCTGAGATAATCTTTTTTTTCATTTTAGA AATGTCCTCCATTTG (110) |
| 29 | GTTCAGAAACTGCCTGATGGCAAAGCTTGATTTTTTTA TTTGAAAAATG (111)<br>CATTAAAATAGCTGAGATAATCTTTTTTTTCATTATATT TACCTCCCATTAGAATTTTTATG (112) |
| 30 | GTTCAGAAACTGCCTGATGGTAAATTTGTTCCAAATGAA GAAACAAATA (113)<br>CATTAAAATAGCTGAGATAATCTTTTTTTTCATAATTAT TTCTCCTTATTCTTAACG (114) |
| 153 | TGGATATTTTTTATAAATCTGG (155)<br>CATGAAATTTTCCTATCTTTTTTAATTC (156) |

TABLE 3

| Promoter sequence (SEQ ID NO in Table 1) | Synthesis with oligos Oligo (SEQ ID NO) | |
|---|---|---|
| 6 | AAATTAAGGATAGATTTTTT | (115) |
| | ATAATAATGAAAAAGGATAGAAAAAATCTATCCTTAATTT | (116) |
| | CTATCCTTTTTCATTATTATTCAAATGATAAAATTTCAAA | (117) |
| | AAAAGGTTTTGCGCTTACATTTTGAAATTTTATCATTTGA | (118) |
| | ATGTAAGCGCAAAACCTTTTGAAGTTTAGGTTTGCGAAGA | (119) |
| | AAAGATTTTTCAAGTGAAAATCTTCGCAAACCTAAACTTC | (120) |
| | TTTTCACTTGAAAAATCTTTCAAAAAATAGTAAAATCAAA | (121) |
| | GTCTGCACTCTTAATACATCTTTGATTTTACTATTTTTTG | (122) |
| | GATGTATTAAGAGTGCAGACGCACTTAAAAATAATAAGGAGACTAAAATG | (123) |
| | CATTTTAGTCTCCTTATTATTTTTAAGTGC | (124) |
| 18 | AGAGGGTTCAGAAACTGCCTGATGGGATAAGATTAATAGT | (125) |
| | TTTAGCTATTAATCTTTTTTTATTTTTATTTAAGAATGGC | (126) |
| | TTAATAAAGCGGTTACTTTGGATTTTTGTGAGCTTGGACT | (127) |
| | AGAAAAAACTTCACAAAATGCTATACTAGGTAGGTAAAA | (128) |
| | AAATATTCGGAGGAATTTTGAAATGAAAAAAAAGATTATC | (129) |
| | TCAGCTATTTTAATGTCTAC | (130) |
| | GTAGACATTAAAATAGCTGAGATAATCTTTTTTTTCATTT | (131) |
| | CAAAATTCCTCCGAATATTTTTTACCTACCTAGTATAGC | (132) |
| | ATTTTGTGAAGTTTTTTCTAGTCCAAGCTCACAAAAATC | (133) |
| | CAAAGTAACCGCTTTATTAAGCCATTCTTAAATAAAAATA | (134) |
| | AAAAAGATTAATAGCTAAAACTATTAATCTTATCCCATC | (135) |
| | AGGCAGTTTCTGAACCCTCT | (136) |
| 30 | GGGTTCAGAAACTGCCTGATGGTAAATTTGTTCCAAATGA | (137) |
| | AGAAACAAATATTTCAAAATCCTACTATTTGATAGTAGGA | (138) |
| | TTTTTAATATATTAGTCCAAAAGCTCAAAAAGGCTGATTT | (139) |
| | AAAGCAGATGAGTAGACTTTTCAATTATTTTGTAAAGCAC | (140) |
| | TTTCAAAAAATAGATAACGCTTGCATTATGAAAATGAAA | (141) |
| | ACGTTATAATTATTTTTATAAAGAACGTTAAATTATAAAA | (142) |
| | CGTTAAGAATAAGGAGAAATAATTATGAAAAAAAAGATTA | (143) |
| | TCTCAGCTATTTTAATGTCT | (144) |
| | AGACATTAAAATAGCTGAGATAATCTTTTTTTTCATAATT | (145) |
| | ATTTCTCCTTATTCTTAACGTTTTATAATTTAACGTTCTT | (146) |
| | TATAAAAATAATTATAACGTTTTCATTTTCATAATGCAAG | (147) |
| | CGTTATCTATTTTTTTGAAAGTGCTTTACAAAATAATTGA | (148) |
| | AAAGTCTACTCATCTGCTTTAAATCAGCCTTTTTGAGCTT | (149) |
| | TTGGACTAATATATTAAAAATCCTACTATCAAATAGTAGG | (150) |
| | ATTTTGAAATATTTGTTTCTTCATTTGGAACAAATTTACC | (151) |
| | ATCAGGCAGTTTCTGAACCC | (152) |

TABLE 4

| BM9 composition: | |
|---|---|
| BM9 | # ml 1000 |
| 10x M9 salts | 100 |
| 10% casiton (Difco, BD Biosciences San Jose, CA USA) | 50 |
| 20% Glucose | 25 |
| water | 772 |
| 1M NaHCO$_3$ | 25 |
| 1M Na$_2$CO$_3$ | 25 |
| 1M MgSO$_4$ | 2 |
| 100 mM CaCl$_2$ | 1 |

10x M9 salts is per liter: 60 g of Na$_2$HPO$_4$, 30 g of KH$_2$PO$_4$, 10 g of NH$_4$Cl, 5 g of NaCl.

TABLE 5

Overview of the various plasmids and their constituents.

| Plasmids | Promoter | Secretion Leader | Gene | Reference |
|---|---|---|---|---|
| pTREX1 | P1 | — | — | Wells et al., 1996 |
| pT1NX | P1 | usp45 | — | Steidler et al., 1998b |
| pT1GLP2 | P1 | usp45 | h[Gly2]GLP-2 | This work |

TABLE 5-continued

Overview of the various plasmids and their constituents.

| Plasmids | Promoter | Secretion Leader | Gene | Reference |
|---|---|---|---|---|
| pThyAGLP2 | PthyA | usp45 | h[Gly2]GLP-2 | This work |
| pT1N$_4$GLP2 | P1 | usp45 N$_4$ | h[Gly2]GLP-2 | This work |
| pThyAN$_4$GLP2 | PthyA | usp45 N$_4$ | h[Gly2]GLP-2 | This work |
| phllAN$_4$GLP2 | PhllA | usp45 N$_4$ | h[Gly2]GLP-2 | This work |

TABLE 6

| Promoter | Relative promoter strength | Strain | Reference |
|---|---|---|---|
| thyA | 1 | Thy12 | [2] |
| | | sAGX0005 | this work |
| PdpsA | 1.6 | sAGX0012 | this work |
| PpepV | 1.7 | sAGX0018 | this work |
| PsodA | 1.3 | sAGX0029 | this work |
| PhllA | 3 | sAGX0037 | this work |

Relative strength of the various promoters tested as assessed by measuring hIL-10 expression from the indicated strains.
[2]: Steidler et al., 2003.

TABLE 7

| Strain | Avg conc hIL10 (ng/10⁹ cells) | relative promoter strength | bacterial density (×10⁹ CFU/ml) |
|---|---|---|---|
| MG1363 | 0 | 0 | 4.1 |
| sAGX0005 | 7.3 | 1 | 4.8 |
| sAGX0037 | 29.1 | 4 | 4.2 |

Relative promoter strength as a function of colony forming units (CFU).

TABLE 8

| Promoter | usp45 | gene | Relative expression | Strain | Reference |
|---|---|---|---|---|---|
| PthyA | wt | hTFF1 | 1 | sAGX0041 | this work |
| PhllA | mut | hTFF1 | 2.3 | sAGX0049 | this work |
| PhllA | wt | hTFF1 | 6.5 | sAGX0048 | this work |
| PthyA | wt | hTFF3 | 1 | sAGX0043 | this work |
| PdpsA | wt | hTFF3 | 1.2 | sAGX0059 | this work |
| PhllA | mut | hTFF3 | 7.5 | sAGX0057 | this work |

Overview of the various TFF expresser strains used in this study and relative expression levels of secreted TFF from the indicated strains.

TABLE 9

| Plasmid | Promoter | Gene | Relative expression | Reference |
|---|---|---|---|---|
| pT1NX | P1 | — | 0 | [3] |
| pAGX0211 | P1 | hPYY G9 (3-36) | 1 | this work |
| pAGX0212 | PthyA | hPYY G9 (3-36) | 1.4 | this work |
| pAGX0213 | PhllA | hPYY G9 (3-36) | 6.3 | this work |

Overview of the various hPYY G9 (3-36) expresser strains used in this study and relative expression levels of secreted hPYY G9 (3-36) from the indicated plasmids. All plasmids were present in L. lactis MG1363.
[3]: Schotte et al., 2000

TABLE 10

| Plasmid | Promoter | Gene | Relative expression | Reference |
|---|---|---|---|---|
| pT1NX | P1 | — | 0 | [2] |
| pAGX0233 | PthyA | GLP-1 G8 (7-36) | 1 | this work |
| pAGX0234 | PhllA | GLP-1 G8 (7-36) | 3 | this work |

Overview of the various hGLP-1 G8 (7-36) expresser strains used in this study and relative expression levels of secreted hGLP-1 G8 (7-36) from the indicated plasmids. All plasmids were present in L. lactis MG1363.
[3]: Schotte et al., 2000

TABLE 11

| Promoter | Strain | hIL-10 (ng/ml) | Relative promoter strength | SEQ ID | Reference |
|---|---|---|---|---|---|
| PthyA | sAGX0005 Thy12 | 27.74 | 1,000 | 153 | this work [2] |
| PpepQ | sAGX0026 | 26.39 | 0.951 | 17 | this work |
| PinfA | sAGX0033 | 16.20 | 0.584 | 25 | this work |
| Ppgk | sAGX0020 | 14.58 | 0.526 | 11 | this work |
| PatpD | sAGX0019 | 6.08 | 0.219 | 10 | this work |
| PrpsD | sAGX0028 | 5.70 | 0.205 | 19 | this work |
| PluxS | sAGX0031 | 4.00 | 0.144 | 23 | this work |
| PglnR | sAGX0017 | 3.03 | 0.109 | 8 | this work |
| PrpoB | sAGX0011 | 0.59 | 0.021 | 2 | this work |
| PrplL | sAGX0035 | 0.50 | 0.018 | 27 | this work |
| PrpoA | sAGX0025 | 0.24 | 0.009 | 16 | this work |
| PfabF | sAGX0023 | 0.20 | 0.007 | 14 | this work |
| PglnA | sAGX0016 | 0.06 | 0.002 | 7 | this work |
| PfabG | sAGX0024 | 0.02 | 0.001 | 15 | this work |

Relative strength of the various promoters as assessed by measuring hIL-10 expression from the indicated strains.

TABLE 12

Successfully sub-cloned promoter sequences

| Strain | SEQ ID | Promoter |
|---|---|---|
| sAGX0005 | 153 | PthyA |
| sAGX0011 | 2 | PrpoB |
| sAGX0012 | 3 | PdpsA |
| sAGX0016 | 7 | PglnA |
| sAGX0017 | 8 | PglnR |
| sAGX0018 | 9 | PpepV |
| sAGX0019 | 10 | PatpD |
| sAGX0020 | 11 | Ppgk |
| sAGX0023 | 14 | PfabF |
| sAGX0024 | 15 | PfabG |
| sAGX0025 | 16 | PrpoA |
| sAGX0026 | 17 | PpepQ |
| sAGX0028 | 19 | PrpsD |
| sAGX0029 | 20 | PsodA |
| sAGX0031 | 23 | PluxS |
| sAGX0033 | 25 | PinfA |
| sAGX0035 | 27 | PrplL |
| sAGX0037 | 28 | PhllA |

REFERENCES

Altschul et al. (1990) J Mol Biol 215: 403-10;
Antelmann et al. (2000) J Bacteriol 182: 4478-90;
Babyatsky M. W., de Beaumont M., Thim L., Podolsky D. K. (1996). Oral trefoil peptides protect against ethanol- and indomethacin-induced gastric injury in rats. Gastroenterology 110, 489-497;
Bolotin et al. (2001) "The complete genome sequence of the lactic acid bacterium *Lactococcus lactis* ssp. *lactis* IL1403" Genome Res 11: 731-753;
Booth et al. (2004) Cell Prolif 37(6): 385-400;
Cazzaniga et al. (1994) "Oral delayed release system for colonic specific delivery" Int. J. Pharm. i08:7';
Chien (1992) "Novel drug delivery system" 2nd edition, M. Dekker;
Deacon C F, Knudsen L B, Madsen K, Wiberg F C, Jacobsen O, Holst J J. (1998) "Dipeptidyl peptidase IV resistant analogues of glucagon-like peptide-1 which have extended metabolic stability and improved biological activity" Diabetologia Mar; 41(3):271-8;
Delorme et al. (1999) J Bacteriol 181(7): 2026-37;
Gasson (1983) J Bacteriol 154: 1-9;
Hansel et al. (1990) "Pharmaceutical dosage forms and drug delivery systems" 5th edition, William and Wilkins;
Kok et al. (1984) Appl Environ Microbiol 48(4): 726-31;
Nauta et al. (1996) Mol Microbiol 19(6): 1331-41;
Maglott et al. (2005), Entrez Gene: gene-centered information at NCBI. Nucleic Acids Res. 33 (Database Issue): D54-D58;
Perez-Martinez et al. (1992) Mol Gen Genet. 234: 401-11;
Playford R J, Marchbank T, Goodlad R A, Chinery R A, Poulsom R, Hanby A M (1996). Transgenic mice that overexpress the human trefoil peptide pS2 have an increased resistance to intestinal damage. Proc Natl Aced Sci USA. 93, 2137-2142;
Prescott et al. (1989) Novel drug delivery, J. Wiley & Sons;
Ross et al. (1990) "Cloning and characterisation of the thymidylate synthase gene from *Lactococcus lactis* ssp. *lactis*." Appl Environ Microbiol 56: 2156-2163;
Schotte L, Steidler L, Vandekerckhove J, Remaut E. (2000) "Secretion of biologically active murine interleukin-10 by *Lactococcus lactis*". Enzyme and Microbial Technology 27:761-765;
Sibakov et al. (1991) Appl Environ Microbiol 57(2): 341-8;

Steidler et al. (1995) "Secretion of biologically active murine interleukin-2 by *Lactococcus lactis* subsp. *lactis*." Appl Environ Microbiol 61(4): 1627-9;

Steidler et al. (1998) "Mucosal delivery of murine interleukin-2 (IL-2) and IL-6 by recombinant strains of *Lactococcus lactis* coexpressing antigen and cytokine." Infect Immun 66(7): 3183-9;

Steidler et al. (2000) Science 289:1352-5

Steidler L, Neirynck S, Huyghebaert N, Snoeck V, Vermeire A, Goddeeris B, Cox E, Remon J P, Remaut E. (2003) "Biological containment of genetically modified *Lactococcus lactis* for intestinal delivery of human interleukin 10" Nat Biotechnol 21:785-789;

Stemmer, et al. (1995) Gene 164(1): 49-53;

Tan X.-D, Hsuch W., Chang H., Wei, K. R. and Gonzalez-Crussi F. (1997) Characterization of a putative receptor for intestinal trefoil factor in rat small intestine: Identification by in situ binding and ligand blotting. Biochem. Biophys. Res. Comunications 237, 673-677.

Tatusova and Madden (1999) FEMS Microbiol Lett 174: 247-250;

van Asseldonk M, Rutten G, Oteman M, Siezen R J, de Vos W M, Simons G (1990) "Cloning of usp45, a gene encoding a secreted protein from *Lactococcus lactis* subsp. *lactis* MG1363" Gene 95(1):155-160;

van der Vossen et al. (1985). Appl Environ Microbiol 50: 540-2;

van der Vossen et al. (1992) Appl Environ Microbiol 58: 3142-9;

Waterfield N R, Le Page R W, Wilson P W, Wells J M. (1995) "The isolation of lactococcal promoters and their use in investigating bacterial luciferase synthesis in *Lactococcus lactis*" Gene 165(1):9-15;

Wells et al. (1993A) Appl Environ Microbiol 59: 3954-9;

Wells et al. (1993B) Mol Microbiol 8(6): 1155-62;

Wong, W. M. (1999). Trefoil peptides. Gut 44: 890-895.

Wright N. A., Poulsom R., Stamp G. W., Hall P. A., Jeffery R. E., Longcroft J., Rio M. C., Tomasetto C and Chambon P. (1990). Epidermal growth factor (EGF/URO) induces expression of regulatory peptides in damaged human gastrointestinal tissues. J. Pathol. 162, 279-284.

What is claimed is:

1. A recombinant nucleic acid comprising a native promoter of a gene for HU-like DNA-binding protein (PhllA) from a *Lactococcus* species as set forth in SEQ ID NO: 28, or a homologue or functional variant thereof wherein the homologue or functional variant is at least 95% identical to the promoter as set forth in SEQ ID NO: 28, operably linked to an open reading frame heterologous to the promoter, said open reading frame comprising a sequence encoding a polypeptide and further comprising a sequence encoding a usp45 or usp45N4 signal sequence 5' upstream of said sequence encoding the polypeptide.

2. The recombinant nucleic acid according to claim 1, further comprising a transcription terminator sequence 3' to said open reading frame.

3. The recombinant nucleic acid according to claim 1, further comprising an operator configured to control transcription from said promoter.

4. The recombinant nucleic acid according to claim 1, further comprising sequences configured to effect insertion of said recombinant nucleic acid into the chromosome of a lactic acid bacterium.

5. The recombinant nucleic acid according to claim 1, wherein the open reading frames encodes a polypeptide capable of eliciting a therapeutic or immunogenic response in a subject.

6. The recombinant nucleic acid according to claim 5, wherein the open reading frames encodes an antigen and/or a non-vaccinogenic therapeutically active polypeptide.

7. The recombinant nucleic acid according to claim 6, wherein said antigen is capable of eliciting an immune response in a human or animal subject, and/or said non-vaccinogenic therapeutically active polypeptide is capable of producing a therapeutic effect in a human or animal subject.

8. The recombinant nucleic acid according to claim 6, wherein said antigen is capable of eliciting an immune response and used as a vaccine in a human or animal subject.

9. The recombinant nucleic acid according to claim 6, wherein said non-vaccinogenic therapeutically active polypeptide is human interleukin-10 (hIL-10), glucagon like peptide-2 (GLP-2), glucagon like peptide-1 (GLP-1), trefoil factor (TFF) or human peptide YY (hPYY).

10. The recombinant nucleic acid according to claim 9, wherein said recombinant nucleic acid comprises:
    (a) PhllA, usp45 and hIL-10; PhllA, usp45N4 and hIL-10;
    (b) PhllA, usp45N4 and hTFF1; PhllA, usp45 and hTFF1;
    (c) PhllA, usp45N4 and hTFF3; PhllA, usp45 and hTFF3;
    (d) PhllA, usp45N4 and hPYY; PhllA, usp45 and hPYY; PhllA, usp45 and hPYY G9 (3-36);
    (e) PhllA, usp45N4 and GLP-1; PhllA, usp45 and GLP-1;
    (f) PhllA, usp45N4 and GLP-2; or PhllA, usp45 and GLP-2.

11. A vector comprising the recombinant nucleic acid as defined in claim 1.

12. The vector according to claim 11, wherein said vector is obtained from pT1NX.

13. A lactic acid bacterium transformed with the recombinant nucleic acid as defined in claim 1.

14. A lactic acid bacterium comprising the recombinant nucleic acid as defined in claim 1, wherein the PhllA promoter is present in the chromosome of said bacterium, and wherein said promoter is operably linked to the open reading frame heterologous to said promoter.

15. The lactic acid bacterium according to claim 14, wherein said PhllA promoter further comprises an operator configured to control transcription from said promoter.

16. The lactic acid bacterium according to claim 14, wherein the reading frame encodes a polypeptide capable of eliciting a therapeutic response or immunogenic response in a subject.

17. The lactic acid bacterium according to claim 14, wherein the reading frame encodes an antigen and/or a non-vaccinogenic therapeutically active polypeptide.

18. The lactic acid bacterium according to claim 17, wherein said antigen is capable of eliciting an immune response in a human or animal subject, and/or said non-vaccinogenic therapeutically active polypeptide is capable of producing a therapeutic effect in a human or animal subject.

19. The lactic acid bacterium according to claim 17, wherein said non-vaccinogenic therapeutically active polypeptide is human interleukin-10 (hIL-10), glucagon like peptide-2 (GLP-2), glucagon like peptide-1 (GLP-1), trefoil factor (TFF) or human peptide YY (hPYY).

20. The lactic acid bacterium according to claim 17, wherein said antigen is capable of eliciting an immune response and used as a vaccine in a human or animal subject.

21. The lactic acid bacterium according to claim 17, wherein said bacterium comprises:
    (a) PhllA, usp45 and hIL-10; PhllA, usp45N4 and hIL-10;
    (b) PhllA, usp45N4 and hTFF1; PhllA, usp45 and hTFF1;
    (c) PhllA, usp45N4 and hTFF3; PhllA, usp45 and hTFF3;
    (d) PhllA, usp45N4 and hPYY; PhllA, usp45 and hPYY; PhllA, usp45 and hPYYG9 (3-36);
    (e) PhllA, usp45N4 and GLP-1; PhllA, usp45 and GLP-1;
    (f) PhllA, usp45N4 and GLP-2; or PhllA, usp45 and GLP-2.

22. A method for recombinant expression of a polypeptide of interest comprising:
    a) culturing the lactic acid bacterium as defined in claim 13, wherein the open reading frame encodes the polypeptide of interest, and
    b) isolating the polypeptide of interest produced by the bacterium in said culturing.

23. A pharmaceutical composition comprising the lactic acid bacterium as defined in claim 13.

24. A lactic acid bacterium transformed with the vector of claim 11.

25. The recombinant nucleic acid according to claim 4, wherein said sequences are configured to effect insertion of said recombinant nucleic acid into the chromosome of the lactic acid bacterium by homologous recombination.

26. The recombinant nucleic acid according to claim 5, wherein said subject is a human or animal subject.

27. The recombinant nucleic acid according to claim 7, wherein said immune response is an immune tolerance response.

28. The lactic acid bacterium according to claim 13, which is a *Lactococcus* bacterium or a *Lactobacillus* bacterium.

29. The lactic acid bacterium according to claim 28, which is a *Lactococcus lactis* bacterium or a *Lactobacillus casei* bacterium.

30. The lactic acid bacterium according to claim 16, wherein said subject is a human or animal subject.

31. The lactic acid bacterium according to claim 18, wherein said immune response is an immune tolerance response.

* * * * *

```
                        SEQUENCE LISTING

<160> NUMBER OF SEQ ID NOS: 185

<210> SEQ ID NO 1
<211> LENGTH: 110
<212> TYPE: DNA
<213> ORGANISM: Lactococcus lactis

<400> SEQUENCE: 1
gattttgtaa ttaatatttg gagagggatt tactgacaaa aattctgtca gtaaatctct     60
aatctcaaaa tcgtctagcg ttaaatttat tagaagtgga gaaagaattg                110

<210> SEQ ID NO 2
<211> LENGTH: 318
<212> TYPE: DNA
<213> ORGANISM: Lactococcus lactis

<400> SEQUENCE: 2
gttcagaaac tgcctgatgg gctagataag ccttgaaaat ttctacaata aatagtataa     60
tagaaataat ggtttgtcag caaaatctgt gggatatatt gtccccatag gctttgtaag    120
caacgaaaca ctactgtttt cgttgctttt ttggcgtctt ttatattgaa taaatcagaa    180
aagttattaa aaagacaaac tactgaattt tcggtttttt taattaaaaa ttcatcaaaa    240
acacagactt ttttaatcaa atctaaaaaa tagaggagaa aacacttgaa aaaaaagatt    300
atctcagcta ttttaatg                                                  318

<210> SEQ ID NO 3
<211> LENGTH: 139
<212> TYPE: DNA
<213> ORGANISM: Lactococcus lactis

<400> SEQUENCE: 3
actaatctat acgaaaattg attttgaatg taactaaaaa tggaattaaa aagaaaattg     60
gtttataata tatttataga aaagttaata ttaaatctct ttatgacatt taatatttaa    120
aaaatggagg ttagttatg                                                 139

<210> SEQ ID NO 4
<211> LENGTH: 94
```

```
<212> TYPE: DNA
<213> ORGANISM: Lactococcus lactis

<400> SEQUENCE: 4
ctaagttact gcaaatctgt ttctagttaa gtgttaaacg cataattagg gcagagatat      60
ataattaatc attataggag aaaaacacaa aatg                                 94

<210> SEQ ID NO 5
<211> LENGTH: 195
<212> TYPE: DNA
<213> ORGANISM: Lactococcus lactis

<400> SEQUENCE: 5
gttcagaaac tgcctgatgg gataaatttc actgacgcaa gcttctttaa tttgtggtaa      60
aatagatgtg attgttagag tagtaattac tatttaaaac caataaagat tcatttctga    120
taaaaaagaa gtgaagaaat caatgaggag aattggatta aaatgaaaaa aaagattatc    180
tcagctattt taatg                                                    195

<210> SEQ ID NO 6
<211> LENGTH: 190
<212> TYPE: DNA
<213> ORGANISM: Lactococcus lactis

<400> SEQUENCE: 6
aaattaagga tagatttttt ctatcctttt tcattattat tcaaatgata aaatttcaaa      60
atgtaagcgc aaaaccttttt gaagtttagg tttgcgaaga ttttcacttg aaaaatcttt    120
caaaaaatag taaaatcaaa gatgtattaa gagtgcagac gcacttaaaa ataataagga    180
gactaaaatg                                                          190

<210> SEQ ID NO 7
<211> LENGTH: 64
<212> TYPE: DNA
<213> ORGANISM: Lactococcus lactis

<400> SEQUENCE: 7
atttggttga cataatttgt caagcaagtt tacagcgaaa atttaactag gagagtaaag      60
catg                                                                 64

<210> SEQ ID NO 8
<211> LENGTH: 123
<212> TYPE: DNA
<213> ORGANISM: Lactococcus lactis

<400> SEQUENCE: 8
caaataaaaa gaactgatgt gagaaaatct cacattgaag cttgactttg cgaaagacaa      60
ggtctataat gatacgtatg gaggcgagat ttggtgaaag aacgtgaatt aagacgctct    120
atg                                                                 123

<210> SEQ ID NO 9
<211> LENGTH: 357
<212> TYPE: DNA
<213> ORGANISM: Lactococcus lactis

<400> SEQUENCE: 9
gttcagaaac tgcctgatgg gatattatct ttatcctcct tatatataat cttttttaaat     60 agtattttca gaataacata ataacctgta acaaggtagg taattaagat gccaataaaa    120
gctcgttatt agtgcagttt ttgaaacaat ataaaatgac tacctaataa ctgtgatact    180
```

```
tatttgagta aaatattttg aagggaaatt tactgatgaa agtggttaag aaaagttact      240
ttaattcata tttattagta cttattgcac catgttgagt aactatgata caatagataa      300
atatactact tcaaggagaa gattatgaaa aaaaagatta tctcagctat tttaatg         357

<210> SEQ ID NO 10
<211> LENGTH: 56
<212> TYPE: DNA
<213> ORGANISM: Lactococcus lactis

<400> SEQUENCE: 10
aaatgaatag aaattctgtt gttagacaga aaataaaaac aggaggaaaa acattg           56

<210> SEQ ID NO 11
<211> LENGTH: 204
<212> TYPE: DNA
<213> ORGANISM: Lactococcus lactis

<400> SEQUENCE: 11
gttgcttagc aaagctcaaa aaatctgtca gtaaaaataa aatcaagaat cttgtaaaag       60
taacccttta caagctaaaa gtaaaattct caaagccaaa atatccgaat ttgtgatata      120
attaacctat cgatttgaat tgaatcagca tggtgctttt tcaatctcaa caaaattatc      180
ttataaggag aattttttcca aatg                                             204

<210> SEQ ID NO 12
<211> LENGTH: 329
<212> TYPE: DNA
<213> ORGANISM: Lactococcus lactis

<400> SEQUENCE: 12
gttcagaaac tgcctgatgg gaataaaaat tactgtcagc ctgctcagta attttttttag      60 tcatattttt aggtggaaag tcaaagatta ttgccaaaag tattagcttt tttaatgtta      120
accgctttca ggagaagggg agttcatttg cttttgtaga gcgctttcta aggtagttta      180
tgtttgcaaa ttttaaaaaa agtgttaaaa taaaagagta agttaaattg ttaacttagt      240
caatttaaaa ggtttgcctt ttataaaatc taatccctat aaggaggaaa ctactaatga      300
aaaaaaagat tatctcagct atttttaatg                                        329

<210> SEQ ID NO 13
<211> LENGTH: 190
<212> TYPE: DNA
<213> ORGANISM: Lactococcus lactis

<400> SEQUENCE: 13
aaataaaaaa ttattggcta gtctgtcagt aattttttat tgtataaaat cattaaaaat       60
gcaaacgctt tttatttgta attgaaataa aaaataacc aagtgaatca tggctgaaaa      120
acacaaaaga aattgtaatt gtgttataat ttaaccgtat ttcaaattca aggaaggttt      180
attaaacatg                                                              190

<210> SEQ ID NO 14
<211> LENGTH: 44
<212> TYPE: DNA
<213> ORGANISM: Lactococcus lactis

<400> SEQUENCE: 14
attgctcatt tataaatttt gaattaaga aggataaaaa tatg                          44
```

```
<210> SEQ ID NO 15
<211> LENGTH: 136
<212> TYPE: DNA
<213> ORGANISM: Lactococcus lactis

<400> SEQUENCE: 15
ggagaaagga attgagttcg tccttctaaa cagtcagcaa taatctgaca tcagagatat      60
cagattattg ctgtccttga agtctaagca ctaaagtgct aagaccctaa ggcgggctca     120
catcttataa ataatg                                                     136

<210> SEQ ID NO 16
<211> LENGTH: 51
<212> TYPE: DNA
<213> ORGANISM: Lactococcus lactis

<400> SEQUENCE: 16
ttagtcactc ttgtcactaa tcacttttcg ctttagagga gaacatacat g               51

<210> SEQ ID NO 17
<211> LENGTH: 210
<212> TYPE: DNA
<213> ORGANISM: Lactococcus lactis

<400> SEQUENCE: 17
ctatcctctt tcttttcttt ttattcatag tatttatgaa aaccattttc atttacaaat      60
tatatcatga actgtaaacc ttttcaacct tcaagtgtgt ttttttacgt gattttcaa      120 taaaaatagc gtagaatggg tatataatgt tttttatttt caggagaatt tagaaaactt     180
attttcatta atattggagg aaccattttg                                      210

<210> SEQ ID NO 18
<211> LENGTH: 210
<212> TYPE: DNA
<213> ORGANISM: Lactococcus lactis

<400> SEQUENCE: 18
gttcagaaac tgcctgatgg gataagatta atagttttag ctattaatct tttttattt      60 ttatttaaga atggcttaat aaagcggtta ctttggattt ttgtgagctt ggactagaaa    120
aaaacttcac aaaatgctat actaggtagg taaaaaaata ttcggaggaa ttttgaaatg    180
aaaaaaaaga ttatctcagc tattttaatg                                      210

<210> SEQ ID NO 19
<211> LENGTH: 213
<212> TYPE: DNA
<213> ORGANISM: Lactococcus lactis

<400> SEQUENCE: 19
gcttttcttg acaaaataag gattttggt ataatagaaa agttgaatat agcagtcagc      60
tagaaagctc gtcaacattt tgctgttatg tcaaggaaga taagtcatta tgttccttgt    120
gtcaagtaac tgaagctata agcgaaggca aaatgaacga attcgaggct gtcaatattc    180
ttcaaataaa atatttggag gacataaatt atg                                  213

<210> SEQ ID NO 20
<211> LENGTH: 151
<212> TYPE: DNA
<213> ORGANISM: Lactococcus lactis

<400> SEQUENCE: 20
aaatcaaatc atttggcaat gatttcaaaa acgactataa tgagaataga attaaaaaat      60
```

-continued

```
aatctaactg aattccattc tcaatctggt caaaataccc aagtattaag acttcaaaat    120
ggattcacat cttaaaagga gaattactat g                                   151

<210> SEQ ID NO 21
<211> LENGTH: 448
<212> TYPE: DNA
<213> ORGANISM: Lactococcus lactis

<400> SEQUENCE: 21
gttcagaaac tgcctgatgg ctcaaaatat aagcttaatc gcttttaaa aaaggattga     60 aagtaaaaaa tagattgaca atcactgtaa aaatgatat tatattaaac ggtacttttt   120
actttggact ctcaggagaa cttgtataag ttgctaaact tcttgtcaga acttggctta   180
agcgaccata tactgactaa aaaattgata aaagaaattg agttcgattt cccatattct   240
aggaaaatag acaaatgttt ccaaggaact tcgttcctct ccaacgtttt ctaattttct   300
acgaatataa acggtcaatc tcacatctta aatcatccaa taaaaagaaa ggaatgcttt   360
tgtatttctc atcgcttcgc agaaatgtgg aaaaatataa aaagcagaca gtaaaatgaa   420
aaaaaagatt atctcagcta ttttaatg                                     448

<210> SEQ ID NO 22
<211> LENGTH: 266
<212> TYPE: DNA
<213> ORGANISM: Lactococcus lactis

<400> SEQUENCE: 22
gcgtcgggct tgcgtcgcta gcttttgctt tatgtacgtc agtacgattc agcacggact    60
tcgtcctaaa agctgcctag caatccttta gcaaaaaatg ttatccgtaa ttggtggttt   120
gatttaggtc aaattgccag tattttgtca atgctaactt tgttagacag acaaaaactc   180
cccgcttgct gattatttta ttaatcagta agaaaatcga tggcaaaaac tatcgaaatt   240
taaaataata tagaggtaga attgtg                                       266

<210> SEQ ID NO 23
<211> LENGTH: 168
<212> TYPE: DNA
<213> ORGANISM: Lactococcus lactis

<400> SEQUENCE: 23
ctacaaacgc tttactgaaa acgctataaa gtcattttac cactttataa taaaataaa    60 aaaatatttc gctaaaaaaa tgatagaata gaattagaat ttaaaataaa ggaggagata   120
cgacaaggct gacttttatc ggctgagttt tgtatcatat attttatg                168

<210> SEQ ID NO 24
<211> LENGTH: 212
<212> TYPE: DNA
<213> ORGANISM: Lactococcus lactis

<400> SEQUENCE: 24
gttcagaaac tgcctgatgg cagcattaag ataaagagtt atgagctaaa aataagcact    60
tgtcaaactt ctgataatct gttatactta tttagtatgt ttttgcatac taataaaact   120
gttcatccgc tgagcttaat ttgctaaaag ctgcttatga tgggcaagag gagaaaaaaa   180
tgaaaaaaaa gattatctca gctatttaa tg                                 212

<210> SEQ ID NO 25
<211> LENGTH: 264
```

```
<212> TYPE: DNA
<213> ORGANISM: Lactococcus lactis

<400> SEQUENCE: 25
taaatcataa aacctctgtc agaggttttt tattttaaat atgaaaaatg aaagataaaa    60
tttactgaca gaaaagtcaa caagcttaaa aataaaaaga acacccgaa agcattgcca    120 taggtactct tatcagataa tctgaaaata aaaatgttgc atttgttgtt gaaaatgct    180 aaaatacata agtccgactt tttagatata tttaaatttg tatttatatc tttcgggaaa    240
tttttaagga ggtacttttg cttg    264

<210> SEQ ID NO 26
<211> LENGTH: 306
<212> TYPE: DNA
<213> ORGANISM: Lactococcus lactis

<400> SEQUENCE: 26
gttcagaaac tgcctgatgg aatagaagat atttttcagt agatatagat taataaaaga    60
taaatagatt tcaaagtaag tttatccttg catttctaaa aaactttga tatacttatt    120 tacggttcta aaagaactga ccgaagacag taggggacga aagtcataaa cttcctaccg    180
aggacaaata tcaaaatgat aattgaactc tctatgtctt tgtgtgtag agattttttg    240 tttctacaac caaaataaaa tggaggtaaa aaatgaaaa aaaagattat ctcagctatt    300
ttaatg    306

<210> SEQ ID NO 27
<211> LENGTH: 122
<212> TYPE: DNA
<213> ORGANISM: Lactococcus lactis

<400> SEQUENCE: 27
aagaagaatc agctgcttaa ttataagcaa catcacttat atcggcggat ttacgcaaca    60
aactaaaaaa ttaataggag aatattaaaa tggcattgaa cattgaaaac atcgttgctg    120
aa    122

<210> SEQ ID NO 28
<211> LENGTH: 107
<212> TYPE: DNA
<213> ORGANISM: Lactococcus lactis

<400> SEQUENCE: 28
aaaacgcctt aaaatggcat tttgacttgc aaactgggct aagatttgct aaaatgaaaa    60
atgcctatgt ttaaggtaaa aaacaaatgg aggacatttc taaaatg    107

<210> SEQ ID NO 29
<211> LENGTH: 93
<212> TYPE: DNA
<213> ORGANISM: Lactococcus lactis

<400> SEQUENCE: 29
caaaagcttg atttttttat ttgaaaaatg ttataatcaa caagtatgtt gttttttaagc    60 acataaaaat tctaatggga ggtaaatata atg    93

<210> SEQ ID NO 30
<211> LENGTH: 295
<212> TYPE: DNA
<213> ORGANISM: Lactococcus lactis

<400> SEQUENCE: 30
```

```
gttcagaaac tgcctgatgg taaatttgtt ccaaatgaag aaacaaatat ttcaaaatcc    60
tactatttga tagtaggatt tttaatatat tagtccaaaa gctcaaaaag gctgatttaa   120
agcagatgag tagacttttc aattattttg taaagcactt tcaaaaaaat agataacgct   180
tgcattatga aaatgaaaac gttataatta tttttataaa gaacgttaaa ttataaaacg   240
ttaagaataa ggagaaataa ttatgaaaaa aaagattatc tcagctattt taatg         295

<210> SEQ ID NO 31
<211> LENGTH: 190
<212> TYPE: DNA
<213> ORGANISM: Lactococcus lactis

<400> SEQUENCE: 31
tcaggataga aaaattttct tcctttgtta aaaacttagt ggagaatttt tcaaactcaa    60
aatgttaaac ttttgaaaac atgcaaaggt aattttaaaa cttgcttatt catgctcaaa   120
aagtataact gcagtttaaa gctaaatagc cttgaactag taaaaatttc tagaagggag   180
catattttg                                                           190

<210> SEQ ID NO 32
<211> LENGTH: 225
<212> TYPE: DNA
<213> ORGANISM: Lactococcus lactis

<400> SEQUENCE: 32
taaatgataa aagttgctga cagagttgtc agtgactttt tttgatgctg tcagcaaaaa    60
gaaaagataa ttttaaattt atgaataaga gtgtggttta attgctagcc tgtcagtaat   120
ttgtgcaaac tgcccaaaag atttaggcac ttatcttatt gttttttagaa acgtttaca   180 gtagaatata aacaaagaac aaaagttact agaggagaaa taatg                   225

<210> SEQ ID NO 33
<211> LENGTH: 91
<212> TYPE: DNA
<213> ORGANISM: Lactococcus lactis

<400> SEQUENCE: 33
cttatttcac aagcataacc ttaggaaatt tctccaaaaa atgataaatt tctaattata    60
gacacataaa aaagaaaggg aatctattat g                                   91

<210> SEQ ID NO 34
<211> LENGTH: 165
<212> TYPE: DNA
<213> ORGANISM: Lactococcus lactis

<400> SEQUENCE: 34
tttaataaaa aactgaaaaa atcacagcta aactcttgtt ttactgtgat tttatgttaa    60
aataattaat gagtgtaatt gtatataaaa ttatctgtac acttaactaa tttattaaaa   120
aaaaatatga atcgtgatgt gtgagggaaa ggagtcgctt ttatg                    165

<210> SEQ ID NO 35
<211> LENGTH: 79
<212> TYPE: DNA
<213> ORGANISM: Lactococcus lactis

<400> SEQUENCE: 35
actaatttaa ttaccagtaa aaatcacttg ttattaagtt aaaggttgag tttcaaaaga    60
tgaaagttag gaaaaattg                                                 79
```

<210> SEQ ID NO 36
<211> LENGTH: 105
<212> TYPE: DNA
<213> ORGANISM: Lactococcus lactis

<400> SEQUENCE: 36

```
atggaaattt taacatattt cttggtataa ttatagtgta aatcatcaaa agaattactg      60
acagatttgt cagtaaattt ttcagtatcc cggaggagaa aaatg                    105
```

<210> SEQ ID NO 37
<211> LENGTH: 201
<212> TYPE: DNA
<213> ORGANISM: Lactococcus lactis

<400> SEQUENCE: 37

```
aattcgctca cttaccgcac gaagcaattt taaactatca acgttttag attacaacac       60 ttaatcattt cctttttgtaa ggaatttaat aggttaattt ttactgacag ttctgtcagt    120
aaattttcgt acgtcaaatc tacttagaaa ggaactgaat tcagtgagta atttacttgc    180
tgaatcgtat ttaatcttat g                                              201
```

<210> SEQ ID NO 38
<211> LENGTH: 398
<212> TYPE: DNA
<213> ORGANISM: Lactococcus lactis

<400> SEQUENCE: 38

```
atttctctcc tcacaaacta ttttatttac tataattatt ttatcacaaa aaaagcgttt      60
tcagcaaaaa tattaatttt attcttagaa aaaaatgcaa aaatctccct taagggatt     120 atattggcaa aaatattagt taaatttgtc agataacatt gagatataaa aaacagaata    180
aaaagaaagt ggagtaggat agctttcact tactcatatt gataaaagaa ataaatgaat    240
agatgcttgc aaaagtagct taaacaatgt ataatgagag agttgctatg caaccatctc    300
gcatttcgtc tcgacaaagt cgtagtgtac gcaagtattg cggctgcgga tgacagatga    360
aagaggaaaa actattttaa aaggagacat taatatgt                            398
```

<210> SEQ ID NO 39
<211> LENGTH: 325
<212> TYPE: DNA
<213> ORGANISM: Lactococcus lactis

<400> SEQUENCE: 39

```
gttgtgtatc tgccatttta ttctcctttc gtatttttat tttattataa tcattttatc      60
atttaattat cattttacta aatgatatga tgcattttga agataataaa atgctagtaa    120
taagagctgg cctaatattc taaaattgta atatatatat atctaaataa taaaattaat    180
cttaaaagtc atctaaaaca atcagtcaaa agttgataaa gaattagggc ttgacaagtt    240
ctaaaataat tgatagaata atagagttga aaagcagaag caccgcttc tcgccttaga    300 ggttatagcc ctgggcaaac aaatg                                          325
```

<210> SEQ ID NO 40
<211> LENGTH: 671
<212> TYPE: DNA
<213> ORGANISM: Lactococcus lactis

<400> SEQUENCE: 40

```
ttaagaaagg taattctcat gtcaaaagga atcttaggga aaaagtggg aatgactcaa       60
```

-continued

| | |
|---|---|
| atcttcacag acaacggtga attaattcct gttactgtga tcgaagcgac tccaaacaca | 120 |
| gttcttcaag ttaaatctgt cgaaacagac ggttacgaag caactcaagt tggtttcgat | 180 |
| acacttcgtg aagttttgac caacaaacct gccaaaggtc atgctgctaa agctaatacg | 240 |
| actcctaagc gcttcgttcg tgaattcaaa ggactcgaag gcgctgaagt aggagcagaa | 300 |
| atcactgttg atacatttgc agccggagat gttgttgatg ttaccggaac ttctaaaggt | 360 |
| aaaggtttcc aaggcccaat caaaacgtca tggtcaatca cgtggtccta tggcccacgg | 420 |
| ttcacgttac caccgtcgtc ctggttcaat gggtcctgtt gcagctaaca agttccaaa | 480 |
| aggtaaaaaa cttgctggac gtatgggtaa caaacgcgtt actgtacaaa accttgttat | 540 |
| tgcacaagtg cttcctgaaa agaacgttat ccttgtaaaa ggtaatgtcc caggtgctaa | 600 |
| gaaatcattg attgttgtta aatcagcaat caaagctaaa taagaaggaa aggagataga | 660 |
| aatctataat g | 671 |

<210> SEQ ID NO 41
<211> LENGTH: 108
<212> TYPE: DNA
<213> ORGANISM: Lactococcus lactis

<400> SEQUENCE: 41

| | |
|---|---|
| gactgatttc ttgaggtaaa atggagtcaa atactgacca ttgataaatc cagaaatata | 60 |
| ttctataata atcactgtta agaaattaaa agggaaaatt taaaaatg | 108 |

<210> SEQ ID NO 42
<211> LENGTH: 63
<212> TYPE: DNA
<213> ORGANISM: Lactococcus lactis

<400> SEQUENCE: 42

| | |
|---|---|
| agtatgattg attttgattt aactaaaaag aaaagtttat aataaaagga agaaataaa | 60 |
| atg | 63 |

<210> SEQ ID NO 43
<211> LENGTH: 138
<212> TYPE: DNA
<213> ORGANISM: Lactococcus lactis

<400> SEQUENCE: 43

| | |
|---|---|
| aacacataaa agtgaggcat cagcctcact tttatgaata ttttcttttt atttgtaaaa | 60 |
| gtttaaaaga acggttacaa ttataaaaag aaaaatttaa ttattgagcg agagctaatc | 120 |
| ataaggagaa caaatttg | 138 |

<210> SEQ ID NO 44
<211> LENGTH: 199
<212> TYPE: DNA
<213> ORGANISM: Lactococcus lactis

<400> SEQUENCE: 44

| | |
|---|---|
| gccataatta taacaaattt gaaagcgtta agaaagttta aactcttttt ttaataattt | 60 |
| tagtaaaagt tgctaaaaaa aaacaatttt ctttgacctt ttttgaccaa tgagttataa | 120 |
| tatagaaaaa taaacaattg aacttaattt attcctaaat tgagtccata tcttatttat | 180 |
| aaaggagatt cattctatg | 199 |

<210> SEQ ID NO 45
<211> LENGTH: 285

```
<212> TYPE: DNA
<213> ORGANISM: Lactococcus lactis

<400> SEQUENCE: 45
ataaaataac aatcctatct ttactgatag gatttttttc cttaaaaaat ccgtcagtaa    60
tttaaaaact tgtaaatttt atctcaccaa ttcaaagat aactttagaa ttgtaaaatg    120
caggacaaac gaggaaatgg cttgtaattc caatcgaaaa atagtaaaat aataggagtc    180
tgttaataga caaataaata tattgaagta tcggcgagtt taattttcac gttccttaca    240
tgaaaattag gcgacagcaa ggtacaaaat aaggagaaaa aaatg                   285

<210> SEQ ID NO 46
<211> LENGTH: 120
<212> TYPE: DNA
<213> ORGANISM: Lactococcus lactis

<400> SEQUENCE: 46
gagtgctctt ttttggatat aatactcggg tatgtgaatt ttcacatata aggcgtggaa    60
gctgtaaaat acagcatcat accacatcac gaaaacaaaa tataaggaga atttatcgtg   120

<210> SEQ ID NO 47
<211> LENGTH: 138
<212> TYPE: DNA
<213> ORGANISM: Lactococcus lactis

<400> SEQUENCE: 47
ttgtaaagaa aaatgttgac agagtgcgga acttctgcta tactaattaa gttcggtctt    60
tttatgaaaa agacctcatt aatttgaaag tgggatttga acaagcccaa actacaaata   120
aggagaaatt acactatg                                                 138

<210> SEQ ID NO 48
<211> LENGTH: 157
<212> TYPE: DNA
<213> ORGANISM: Lactococcus lactis

<400> SEQUENCE: 48
aaaagaagta gtataataat atagttgtct ttgtgaaatc tcataaagtg caaccgcacg    60
aagtttcgta ataagtggcg taagcccacg aacaaaggcg agtctaacag tcgcttgact   120
taaaagcgat gaaatctaac aaggaggaat cacaatg                            157

<210> SEQ ID NO 49
<211> LENGTH: 290
<212> TYPE: DNA
<213> ORGANISM: Lactococcus lactis

<400> SEQUENCE: 49
ctgtcagagg ttttttattt taaatatgaa aaatgaaaga taaaatttac tgacagaaaa    60
gtcaacaagc ttaaaaataa aaagaaacac ccgaaagcat tgccataggt actcttatca   120
gataatctga aaataaaaat ggactcaggc tagaaaaata aaggctttta tgaaagaaag   180
acttgcattt gttgttgaaa aatgctaaaa tacataagtc cgacttttta gatatattta   240
aatttgtatt tatatctttc gggaaatttt taaggaggta cttttgcttg                290

<210> SEQ ID NO 50
<211> LENGTH: 141
<212> TYPE: DNA
<213> ORGANISM: Lactococcus lactis

<400> SEQUENCE: 50
```

```
gagccttctc ggcgtcttgt taaatttgat aaaacttatt atcaaattta atgagatgtc      60
gaaagtgcat ctataaattc cgccaactcc gccttagtag cggcagtggt acaaatattt     120
aaaggagaaa ctcgcaaaat g                                               141

<210> SEQ ID NO 51
<211> LENGTH: 569
<212> TYPE: DNA
<213> ORGANISM: Lactococcus lactis

<400> SEQUENCE: 51
atgacgaaat tgataacatc gtttaagaaa gctccgtaag taaatttagt cttaccaaca      60
gttactgata agtgggcaag agcgctgctt tggacgaaca ttccaatcaa agggttaatc     120
aaattatcaa ccaaagattt aactaaagca gtaaaagctg ccccgatgat aaccccaacg     180
gccaagtcta agacattgcc acgcaaaata agttttttaa attcctttaa cataaatcct     240
cctatataaa tagtttataa aacctttaat caaattatat caaaaagttt aaagatgaca     300
aagtgtgggt tcttgtcttt ttcagtaaat tcattgattt tatttaaaat tttaaaagat     360
atataaaaag aactggaaag aataaaaaaa gtctaaaaag tccttgacaa ggcacatctc     420
ctttgataga atagacaagt gctgttaaaa acagtatgta gcgacgaaac gagaggttgc     480
gacacacccg aaggtattgc catacctaac gtgtcggttt tcccgtggag ctagcctatt     540
gaatacaata gacgagagga gaaaaaatg                                       569

<210> SEQ ID NO 52
<211> LENGTH: 110
<212> TYPE: DNA
<213> ORGANISM: Lactococcus lactis

<400> SEQUENCE: 52
aaatctaaat gttttctctt gactaaatct gaccattgag ataaaataag aatatgttag      60
cacacaacta ttaagagtgc taaaaataaa aaatggagta aagtataatg                110

<210> SEQ ID NO 53
<211> LENGTH: 119
<212> TYPE: DNA
<213> ORGANISM: Lactococcus lactis

<400> SEQUENCE: 53
atggttttgt cggaaaaatt ttttgacaga gtcatatttt actgttatta ttaacagaat      60
agtcccctga tagtaaaata tgagggtgcc catcgggcgt aagaaaggaa ataaacatg     119

<210> SEQ ID NO 54
<211> LENGTH: 274
<212> TYPE: DNA
<213> ORGANISM: Lactococcus lactis

<400> SEQUENCE: 54
tatttggtga ttttcaaat tagaattcat attttattta aaagtctttt ctaaagactt      60
ttgtttactt tactagagaa aacggttgaa ttcaggcaaa aaataacgta taattaacat     120
gtatctaaga aatttttaat gagatatttc tgtcagtatt agaaaatgta aagttctcta     180
aagatgagaa agttaagtaa ctgacagaag tgaaattatt agttttttagt ttgatctggc     240 tttttacaga taaatttaaa ggaggtgtct tatg                                 274

<210> SEQ ID NO 55
<211> LENGTH: 56
```

```
<212> TYPE: DNA
<213> ORGANISM: Artificial
<220> FEATURE:
<223> OTHER INFORMATION: primer, based on Lactococcus lactis

<400> SEQUENCE: 55
gttcagaaac tgcctgatgg attttgtaat taatattttg agatttattt actgac          56

<210> SEQ ID NO 56
<211> LENGTH: 61
<212> TYPE: DNA
<213> ORGANISM: Artificial
<220> FEATURE:
<223> OTHER INFORMATION: primer, based on Lactococcus lactis

<400> SEQUENCE: 56
cattaaaata gctgagataa tcttttttt caattctttc tccacttcta ataaatttaa       60
c                                                                      61

<210> SEQ ID NO 57
<211> LENGTH: 43
<212> TYPE: DNA
<213> ORGANISM: Artificial
<220> FEATURE:
<223> OTHER INFORMATION: primer, based on Lactococcus lactis

<400> SEQUENCE: 57
gttcagaaac tgcctgatgg gctagataag ccttgaaaat ttc                         43

<210> SEQ ID NO 58
<211> LENGTH: 56
<212> TYPE: DNA
<213> ORGANISM: Artificial
<220> FEATURE:
<223> OTHER INFORMATION: primer, based on Lactococcus lactis

<400> SEQUENCE: 58
cattaaaata gctgagataa tcttttttt caagtgtttt ctcctctatt ttttag           56

<210> SEQ ID NO 59
<211> LENGTH: 51
<212> TYPE: DNA
<213> ORGANISM: Artificial
<220> FEATURE:
<223> OTHER INFORMATION: primer, based on Lactococcus lactis

<400> SEQUENCE: 59
ggttcagaaa ctgcctgatg gactaatcta tacgaaaatt gattttgaat g               51

<210> SEQ ID NO 60
<211> LENGTH: 59
<212> TYPE: DNA
<213> ORGANISM: Artificial
<220> FEATURE:
<223> OTHER INFORMATION: primer, based on Lactococcus lactis

<400> SEQUENCE: 60
cattaaaata gctgagataa tcttttttt cataactaac ctccattttt taaatatta        59

<210> SEQ ID NO 61
<211> LENGTH: 43
<212> TYPE: DNA
<213> ORGANISM: Artificial
<220> FEATURE:
<223> OTHER INFORMATION: primer, based on Lactococcus lactis

<400> SEQUENCE: 61
```

```
gttcagaaac tgcctgatgg ctaagttact gcaaatctgt ttc                    43
```

<210> SEQ ID NO 62
<211> LENGTH: 55
<212> TYPE: DNA
<213> ORGANISM: Artificial
<220> FEATURE:
<223> OTHER INFORMATION: primer, based on Lactococcus lactis

<400> SEQUENCE: 62

```
cattaaaata gctgagataa tctttttttt cattttgtgt ttttctccta taatg       55
```

<210> SEQ ID NO 63
<211> LENGTH: 42
<212> TYPE: DNA
<213> ORGANISM: Artificial
<220> FEATURE:
<223> OTHER INFORMATION: primer, based on Lactococcus lactis

<400> SEQUENCE: 63

```
gttcagaaac tgcctgatgg gataaatttc actgacgcaa gc                     42
```

<210> SEQ ID NO 64
<211> LENGTH: 55
<212> TYPE: DNA
<213> ORGANISM: Artificial
<220> FEATURE:
<223> OTHER INFORMATION: primer, based on Lactococcus lactis

<400> SEQUENCE: 64

```
cattaaaata gctgagataa tctttttttt cattttaatc caattctcct cattg       55
```

<210> SEQ ID NO 65
<211> LENGTH: 52
<212> TYPE: DNA
<213> ORGANISM: Artificial
<220> FEATURE:
<223> OTHER INFORMATION: primer, based on Lactococcus lactis

<400> SEQUENCE: 65

```
gttcagaaac tgcctgatgg aaattaagga tagatttttt ctatccttttt tc         52
```

<210> SEQ ID NO 66
<211> LENGTH: 61
<212> TYPE: DNA
<213> ORGANISM: Artificial
<220> FEATURE:
<223> OTHER INFORMATION: primer, based on Lactococcus lactis

<400> SEQUENCE: 66

```
cattaaaata gctgagataa tctttttttt cattttagtc tcctattat ttttaagtgc   60
g                                                                  61
```

<210> SEQ ID NO 67
<211> LENGTH: 44
<212> TYPE: DNA
<213> ORGANISM: Artificial
<220> FEATURE:
<223> OTHER INFORMATION: primer, based on Lactococcus lactis

<400> SEQUENCE: 67

```
gttcagaaac tgcctgatgg atttggttga cataatttgt caag                   44
```

<210> SEQ ID NO 68
<211> LENGTH: 58

```
<212> TYPE: DNA
<213> ORGANISM: Artificial
<220> FEATURE:
<223> OTHER INFORMATION: primer, based on Lactococcus lactis

<400> SEQUENCE: 68
cattaaaata gctgagataa tcttttttt catgctttac tctcctagtt aaattttc      58

<210> SEQ ID NO 69
<211> LENGTH: 49
<212> TYPE: DNA
<213> ORGANISM: Artificial
<220> FEATURE:
<223> OTHER INFORMATION: primer, based on Lactococcus lactis

<400> SEQUENCE: 69
gttcagaaac tgcctgatgg caaataaaaa gaactgatgt gagaaaatc              49

<210> SEQ ID NO 70
<211> LENGTH: 51
<212> TYPE: DNA
<213> ORGANISM: Artificial
<220> FEATURE:
<223> OTHER INFORMATION: primer, based on Lactococcus lactis

<400> SEQUENCE: 70
cattaaaata gctgagataa tcttttttt catagagcgt cttaattcac g            51

<210> SEQ ID NO 71
<211> LENGTH: 51
<212> TYPE: DNA
<213> ORGANISM: Artificial
<220> FEATURE:
<223> OTHER INFORMATION: primer, based on Lactococcus lactis

<400> SEQUENCE: 71
gttcagaaac tgcctgatgg gatattatct ttatcctcct tatatataat c           51

<210> SEQ ID NO 72
<211> LENGTH: 52
<212> TYPE: DNA
<213> ORGANISM: Artificial
<220> FEATURE:
<223> OTHER INFORMATION: primer, based on Lactococcus lactis

<400> SEQUENCE: 72
cattaaaata gctgagataa tcttttttt cataatcttc tccttgaagt ag           52

<210> SEQ ID NO 73
<211> LENGTH: 49
<212> TYPE: DNA
<213> ORGANISM: Artificial
<220> FEATURE:
<223> OTHER INFORMATION: primer, based on Lactococcus lactis

<400> SEQUENCE: 73
gttcagaaac tgcctgatgg ttactgtcaa acattattct caatgttac              49

<210> SEQ ID NO 74
<211> LENGTH: 59
<212> TYPE: DNA
<213> ORGANISM: Artificial
<220> FEATURE:
<223> OTHER INFORMATION: primer, based on Lactococcus lactis

<400> SEQUENCE: 74
cattaaaata gctgagataa tcttttttt cattttaag ctaatcagta aaaatttac     59
```

<210> SEQ ID NO 75
<211> LENGTH: 37
<212> TYPE: DNA
<213> ORGANISM: Artificial
<220> FEATURE:
<223> OTHER INFORMATION: primer, based on Lactococcus lactis

<400> SEQUENCE: 75
gttcagaaac tgcctgatgg gttgcttagc aaagctc                         37

<210> SEQ ID NO 76
<211> LENGTH: 55
<212> TYPE: DNA
<213> ORGANISM: Artificial
<220> FEATURE:
<223> OTHER INFORMATION: primer, based on Lactococcus lactis

<400> SEQUENCE: 76
cattaaaata gctgagataa tcttttttttt catttggaaa aattctcctt ataag    55

<210> SEQ ID NO 77
<211> LENGTH: 44
<212> TYPE: DNA
<213> ORGANISM: Artificial
<220> FEATURE:
<223> OTHER INFORMATION: primer, based on Lactococcus lactis

<400> SEQUENCE: 77
gttcagaaac tgcctgatgg gaataaaaat tactgtcagc ctgc                 44

<210> SEQ ID NO 78
<211> LENGTH: 55
<212> TYPE: DNA
<213> ORGANISM: Artificial
<220> FEATURE:
<223> OTHER INFORMATION: primer, based on Lactococcus lactis

<400> SEQUENCE: 78
cattaaaata gctgagataa tcttttttttt cattagtagt ttcctcctta taggg    55

<210> SEQ ID NO 79
<211> LENGTH: 49
<212> TYPE: DNA
<213> ORGANISM: Artificial
<220> FEATURE:
<223> OTHER INFORMATION: primer, based on Lactococcus lactis

<400> SEQUENCE: 79
gttcagaaac tgcctgatgg aaataaaaaa ttattggcta gtctgtcag            49

<210> SEQ ID NO 80
<211> LENGTH: 58
<212> TYPE: DNA
<213> ORGANISM: Artificial
<220> FEATURE:
<223> OTHER INFORMATION: primer, based on Lactococcus lactis

<400> SEQUENCE: 80
cattaaaata gctgagataa tcttttttttt catgtttaat aaaccttcct tgaatttg 58

<210> SEQ ID NO 81
<211> LENGTH: 53
<212> TYPE: DNA
<213> ORGANISM: Artificial
<220> FEATURE:
<223> OTHER INFORMATION: primer, based on Lactococcus lactis

```
<400> SEQUENCE: 81
gttcagaaac tgcctgatgg attgctcatt tataaatttt gaaattaaga agg          53

<210> SEQ ID NO 82
<211> LENGTH: 68
<212> TYPE: DNA
<213> ORGANISM: Artificial
<220> FEATURE:
<223> OTHER INFORMATION: primer, based on Lactococcus lactis

<400> SEQUENCE: 82
cattaaaata gctgagataa tctttttttt catatttta tccttcttaa tttcaaaatt    60
tataaatg                                                           68

<210> SEQ ID NO 83
<211> LENGTH: 40
<212> TYPE: DNA
<213> ORGANISM: Artificial
<220> FEATURE:
<223> OTHER INFORMATION: primer, based on Lactococcus lactis

<400> SEQUENCE: 83
gttcagaaac tgcctgatgg ggagaaagga attgagttcg                        40

<210> SEQ ID NO 84
<211> LENGTH: 53
<212> TYPE: DNA
<213> ORGANISM: Artificial
<220> FEATURE:
<223> OTHER INFORMATION: primer, based on Lactococcus lactis

<400> SEQUENCE: 84
cattaaaata gctgagataa tctttttttt cattatttat aagatgtgag ccc          53

<210> SEQ ID NO 85
<211> LENGTH: 44
<212> TYPE: DNA
<213> ORGANISM: Artificial
<220> FEATURE:
<223> OTHER INFORMATION: primer, based on Lactococcus lactis

<400> SEQUENCE: 85
gttcagaaac tgcctgatgg ttagtcactc ttgtcactaa tcac                   44

<210> SEQ ID NO 86
<211> LENGTH: 53
<212> TYPE: DNA
<213> ORGANISM: Artificial
<220> FEATURE:
<223> OTHER INFORMATION: primer, based on Lactococcus lactis

<400> SEQUENCE: 86
cattaaaata gctgagataa tctttttttt catgtatgtt ctcctctaaa gcg          53

<210> SEQ ID NO 87
<211> LENGTH: 50
<212> TYPE: DNA
<213> ORGANISM: Artificial
<220> FEATURE:
<223> OTHER INFORMATION: primer, based on Lactococcus lactis

<400> SEQUENCE: 87
gttcagaaac tgcctgatgg ctatcctctt tcttttcttt ttattcatag              50
```

```
<210> SEQ ID NO 88
<211> LENGTH: 55
<212> TYPE: DNA
<213> ORGANISM: Artificial
<220> FEATURE:
<223> OTHER INFORMATION: primer, based on Lactococcus lactis

<400> SEQUENCE: 88
cattaaaata gctgagataa tcttttttt caaaatggtt cctccaatat taatg        55

<210> SEQ ID NO 89
<211> LENGTH: 49
<212> TYPE: DNA
<213> ORGANISM: Artificial
<220> FEATURE:
<223> OTHER INFORMATION: primer, based on Lactococcus lactis

<400> SEQUENCE: 89
gttcagaaac tgcctgatgg gataagatta atagttttag ctattaatc              49

<210> SEQ ID NO 90
<211> LENGTH: 52
<212> TYPE: DNA
<213> ORGANISM: Artificial
<220> FEATURE:
<223> OTHER INFORMATION: primer, based on Lactococcus lactis

<400> SEQUENCE: 90
cattaaaata gctgagataa tcttttttt catttcaaaa ttcctccgaa ta           52

<210> SEQ ID NO 91
<211> LENGTH: 48
<212> TYPE: DNA
<213> ORGANISM: Artificial
<220> FEATURE:
<223> OTHER INFORMATION: primer, based on Lactococcus lactis

<400> SEQUENCE: 91
gttcagaaac tgcctgatgg gcttttcttg acaaaataag gattttg                 48

<210> SEQ ID NO 92
<211> LENGTH: 61
<212> TYPE: DNA
<213> ORGANISM: Artificial
<220> FEATURE:
<223> OTHER INFORMATION: primer, based on Lactococcus lactis

<400> SEQUENCE: 92
cattaaaata gctgagataa tcttttttt cataatttat gtcctccaaa tattttattt   60
g                                                                  61

<210> SEQ ID NO 93
<211> LENGTH: 46
<212> TYPE: DNA
<213> ORGANISM: Artificial
<220> FEATURE:
<223> OTHER INFORMATION: primer, based on Lactococcus lactis

<400> SEQUENCE: 93
gttcagaaac tgcctgatgg aaatcaaatc atttggcaat gatttc                 46

<210> SEQ ID NO 94
<211> LENGTH: 56
<212> TYPE: DNA
<213> ORGANISM: Artificial
<220> FEATURE:
<223> OTHER INFORMATION: primer, based on Lactococcus lactis
```

<400> SEQUENCE: 94
cattaaaata gctgagataa tcttttttt catagtaatt ctccttttaa gatgtg        56

<210> SEQ ID NO 95
<211> LENGTH: 42
<212> TYPE: DNA
<213> ORGANISM: Artificial
<220> FEATURE:
<223> OTHER INFORMATION: primer, based on Lactococcus lactis

<400> SEQUENCE: 95
gttcagaaac tgcctgatgg ctcaaaatat aagcttaatc gc        42

<210> SEQ ID NO 96
<211> LENGTH: 60
<212> TYPE: DNA
<213> ORGANISM: Artificial
<220> FEATURE:
<223> OTHER INFORMATION: primer, based on Lactococcus lactis

<400> SEQUENCE: 96
cattaaaata gctgagataa tcttttttt cattttactg tctgcttttt atatttttcc        60

<210> SEQ ID NO 97
<211> LENGTH: 34
<212> TYPE: DNA
<213> ORGANISM: Artificial
<220> FEATURE:
<223> OTHER INFORMATION: primer, based on Lactococcus lactis

<400> SEQUENCE: 97
gttcagaaac tgcctgatgg gcgtcgggct tgcg        34

<210> SEQ ID NO 98
<211> LENGTH: 62
<212> TYPE: DNA
<213> ORGANISM: Artificial
<220> FEATURE:
<223> OTHER INFORMATION: primer, based on Lactococcus lactis

<400> SEQUENCE: 98
cattaaaata gctgagataa tcttttttt cacaattcta cctctatatt attttaaatt        60
tc        62

<210> SEQ ID NO 99
<211> LENGTH: 43
<212> TYPE: DNA
<213> ORGANISM: Artificial
<220> FEATURE:
<223> OTHER INFORMATION: primer, based on Lactococcus lactis

<400> SEQUENCE: 99
gttcagaaac tgcctgatgg ctacaaacgc tttactgaaa acg        43

<210> SEQ ID NO 100
<211> LENGTH: 57
<212> TYPE: DNA
<213> ORGANISM: Artificial
<220> FEATURE:
<223> OTHER INFORMATION: primer, based on Lactococcus lactis

<400> SEQUENCE: 100
cattaaaata gctgagataa tcttttttt cataaaatat atgatacaaa actcagc        57

```
<210> SEQ ID NO 101
<211> LENGTH: 46
<212> TYPE: DNA
<213> ORGANISM: Artificial
<220> FEATURE:
<223> OTHER INFORMATION: primer, based on Lactococcus lactis

<400> SEQUENCE: 101
gttcagaaac tgcctgatgg cagcattaag ataaagagtt atgagc              46

<210> SEQ ID NO 102
<211> LENGTH: 51
<212> TYPE: DNA
<213> ORGANISM: Artificial
<220> FEATURE:
<223> OTHER INFORMATION: primer, based on Lactococcus lactis

<400> SEQUENCE: 102
cattaaaata gctgagataa tctttttttt cattttttc tcctcttgcc c          51

<210> SEQ ID NO 103
<211> LENGTH: 45
<212> TYPE: DNA
<213> ORGANISM: Artificial
<220> FEATURE:
<223> OTHER INFORMATION: primer, based on Lactococcus lactis

<400> SEQUENCE: 103
gttcagaaac tgcctgatgg taaatcataa aacctctgtc agagg                45

<210> SEQ ID NO 104
<211> LENGTH: 58
<212> TYPE: DNA
<213> ORGANISM: Artificial
<220> FEATURE:
<223> OTHER INFORMATION: primer, based on Lactococcus lactis

<400> SEQUENCE: 104
cattaaaata gctgagataa tctttttttt caagcaaaag tacctcctta aaatttc    58

<210> SEQ ID NO 105
<211> LENGTH: 48
<212> TYPE: DNA
<213> ORGANISM: Artificial
<220> FEATURE:
<223> OTHER INFORMATION: primer, based on Lactococcus lactis

<400> SEQUENCE: 105
gttcagaaac tgcctgatgg aatagaagat attttcagt agatatag              48

<210> SEQ ID NO 106
<211> LENGTH: 57
<212> TYPE: DNA
<213> ORGANISM: Artificial
<220> FEATURE:
<223> OTHER INFORMATION: primer, based on Lactococcus lactis

<400> SEQUENCE: 106
cattaaaata gctgagataa tctttttttt cattttttta cctccatttt attttgg    57

<210> SEQ ID NO 107
<211> LENGTH: 45
<212> TYPE: DNA
<213> ORGANISM: Artificial
<220> FEATURE:
<223> OTHER INFORMATION: primer, based on Lactococcus lactis

<400> SEQUENCE: 107
```

```
gttcagaaac tgcctgatgg ttataagcaa catcacttat atcgg          45

<210> SEQ ID NO 108
<211> LENGTH: 60
<212> TYPE: DNA
<213> ORGANISM: Artificial
<220> FEATURE:
<223> OTHER INFORMATION: primer, based on Lactococcus lactis

<400> SEQUENCE: 108
cattaaaata gctgagataa tctttttttt cattttaata ttctcctatt aattttttag    60

<210> SEQ ID NO 109
<211> LENGTH: 44
<212> TYPE: DNA
<213> ORGANISM: Artificial
<220> FEATURE:
<223> OTHER INFORMATION: primer, based on Lactococcus lactis

<400> SEQUENCE: 109
gttcagaaac tgcctgatgg aaaacgcctt aaaatggcat tttg          44

<210> SEQ ID NO 110
<211> LENGTH: 54
<212> TYPE: DNA
<213> ORGANISM: Artificial
<220> FEATURE:
<223> OTHER INFORMATION: primer, based on Lactococcus lactis

<400> SEQUENCE: 110
cattaaaata gctgagataa tctttttttt cattttagaa atgtcctcca tttg          54

<210> SEQ ID NO 111
<211> LENGTH: 50
<212> TYPE: DNA
<213> ORGANISM: Artificial
<220> FEATURE:
<223> OTHER INFORMATION: primer, based on Lactococcus lactis

<400> SEQUENCE: 111
gttcagaaac tgcctgatgg caaaagcttg atttttttat ttgaaaaatg    50

<210> SEQ ID NO 112
<211> LENGTH: 62
<212> TYPE: DNA
<213> ORGANISM: Artificial
<220> FEATURE:
<223> OTHER INFORMATION: primer, based on Lactococcus lactis

<400> SEQUENCE: 112
cattaaaata gctgagataa tctttttttt cattatattt acctcccatt agaatttta    60 tg                                                                  62

<210> SEQ ID NO 113
<211> LENGTH: 49
<212> TYPE: DNA
<213> ORGANISM: Artificial
<220> FEATURE:
<223> OTHER INFORMATION: primer, based on Lactococcus lactis

<400> SEQUENCE: 113
gttcagaaac tgcctgatgg taaatttgtt ccaaatgaag aaacaaata     49

<210> SEQ ID NO 114
<211> LENGTH: 57
```

```
<212> TYPE: DNA
<213> ORGANISM: Artificial
<220> FEATURE:
<223> OTHER INFORMATION: primer, based on Lactococcus lactis

<400> SEQUENCE: 114
cattaaaata gctgagataa tctttttttt cataattatt tctccttatt cttaacg      57

<210> SEQ ID NO 115
<211> LENGTH: 20
<212> TYPE: DNA
<213> ORGANISM: Artificial
<220> FEATURE:
<223> OTHER INFORMATION: primer, based on Lactococcus lactis

<400> SEQUENCE: 115
aaattaagga tagattttt                                                 20

<210> SEQ ID NO 116
<211> LENGTH: 40
<212> TYPE: DNA
<213> ORGANISM: Artificial
<220> FEATURE:
<223> OTHER INFORMATION: primer, based on Lactococcus lactis

<400> SEQUENCE: 116
ataataatga aaaggatag aaaaaatcta tccttaattt                           40

<210> SEQ ID NO 117
<211> LENGTH: 40
<212> TYPE: DNA
<213> ORGANISM: Artificial
<220> FEATURE:
<223> OTHER INFORMATION: primer, based on Lactococcus lactis

<400> SEQUENCE: 117 ctatccttt tcattattat tcaaatgata aaatttcaaa                           40

<210> SEQ ID NO 118
<211> LENGTH: 40
<212> TYPE: DNA
<213> ORGANISM: Artificial
<220> FEATURE:
<223> OTHER INFORMATION: primer, based on Lactococcus lactis

<400> SEQUENCE: 118
aaaaggtttt gcgcttacat tttgaaattt tatcatttga                          40

<210> SEQ ID NO 119
<211> LENGTH: 40
<212> TYPE: DNA
<213> ORGANISM: Artificial
<220> FEATURE:
<223> OTHER INFORMATION: primer, based on Lactococcus lactis

<400> SEQUENCE: 119
atgtaagcgc aaaacctttt gaagtttagg tttgcgaaga                          40

<210> SEQ ID NO 120
<211> LENGTH: 40
<212> TYPE: DNA
<213> ORGANISM: Artificial
<220> FEATURE:
<223> OTHER INFORMATION: primer, based on Lactococcus lactis

<400> SEQUENCE: 120
aaagattttt caagtgaaaa tcttcgcaaa cctaaacttc                          40
```

<210> SEQ ID NO 121
<211> LENGTH: 40
<212> TYPE: DNA
<213> ORGANISM: Artificial
<220> FEATURE:
<223> OTHER INFORMATION: primer, based on Lactococcus lactis

<400> SEQUENCE: 121
ttttcacttg aaaaatcttt caaaaaatag taaaatcaaa                    40

<210> SEQ ID NO 122
<211> LENGTH: 40
<212> TYPE: DNA
<213> ORGANISM: Artificial
<220> FEATURE:
<223> OTHER INFORMATION: primer, based on Lactococcus lactis

<400> SEQUENCE: 122
gtctgcactc ttaatacatc tttgatttta ctatttttg                     40

<210> SEQ ID NO 123
<211> LENGTH: 50
<212> TYPE: DNA
<213> ORGANISM: Artificial
<220> FEATURE:
<223> OTHER INFORMATION: primer, based on Lactococcus lactis

<400> SEQUENCE: 123
gatgtattaa gagtgcagac gcacttaaaa ataataagga gactaaaatg         50

<210> SEQ ID NO 124
<211> LENGTH: 30
<212> TYPE: DNA
<213> ORGANISM: Artificial
<220> FEATURE:
<223> OTHER INFORMATION: primer, based on Lactococcus lactis

<400> SEQUENCE: 124
cattttagtc tccttattat ttttaagtgc                               30

<210> SEQ ID NO 125
<211> LENGTH: 40
<212> TYPE: DNA
<213> ORGANISM: Artificial
<220> FEATURE:
<223> OTHER INFORMATION: primer, based on Lactococcus lactis

<400> SEQUENCE: 125
agagggttca gaaactgcct gatgggataa gattaatagt                    40

<210> SEQ ID NO 126
<211> LENGTH: 40
<212> TYPE: DNA
<213> ORGANISM: Artificial
<220> FEATURE:
<223> OTHER INFORMATION: primer, based on Lactococcus lactis

<400> SEQUENCE: 126
tttagctatt aatctttttt tatttttatt taagaatggc                    40

<210> SEQ ID NO 127
<211> LENGTH: 40
<212> TYPE: DNA
<213> ORGANISM: Artificial
<220> FEATURE:
<223> OTHER INFORMATION: primer, based on Lactococcus lactis

<400> SEQUENCE: 127
ttaataaagc ggttactttg gattttgtg agcttggact                           40

<210> SEQ ID NO 128
<211> LENGTH: 40
<212> TYPE: DNA
<213> ORGANISM: Artificial
<220> FEATURE:
<223> OTHER INFORMATION: primer, based on Lactococcus lactis

<400> SEQUENCE: 128
agaaaaaaac ttcacaaaat gctatactag gtaggtaaaa                          40

<210> SEQ ID NO 129
<211> LENGTH: 40
<212> TYPE: DNA
<213> ORGANISM: Artificial
<220> FEATURE:
<223> OTHER INFORMATION: primer, based on Lactococcus lactis

<400> SEQUENCE: 129
aaatattcgg aggaattttg aaatgaaaaa aaagattatc                          40

<210> SEQ ID NO 130
<211> LENGTH: 20
<212> TYPE: DNA
<213> ORGANISM: Artificial
<220> FEATURE:
<223> OTHER INFORMATION: primer, based on Lactococcus lactis

<400> SEQUENCE: 130
tcagctattt taatgtctac                                                20

<210> SEQ ID NO 131
<211> LENGTH: 40
<212> TYPE: DNA
<213> ORGANISM: Artificial
<220> FEATURE:
<223> OTHER INFORMATION: primer, based on Lactococcus lactis

<400> SEQUENCE: 131
gtagacatta aaatagctga gataatcttt ttttcattt                           40

<210> SEQ ID NO 132
<211> LENGTH: 40
<212> TYPE: DNA
<213> ORGANISM: Artificial
<220> FEATURE:
<223> OTHER INFORMATION: primer, based on Lactococcus lactis

<400> SEQUENCE: 132
caaaattcct ccgaatattt ttttacctac ctagtatagc                          40

<210> SEQ ID NO 133
<211> LENGTH: 40
<212> TYPE: DNA
<213> ORGANISM: Artificial
<220> FEATURE:
<223> OTHER INFORMATION: primer, based on Lactococcus lactis

<400> SEQUENCE: 133
attttgtgaa gttttttttct agtccaagct cacaaaaatc                         40

<210> SEQ ID NO 134
<211> LENGTH: 40

```
<212> TYPE: DNA
<213> ORGANISM: Artificial
<220> FEATURE:
<223> OTHER INFORMATION: primer, based on Lactococcus lactis

<400> SEQUENCE: 134
caaagtaacc gctttattaa gccattctta aataaaaata                          40

<210> SEQ ID NO 135
<211> LENGTH: 40
<212> TYPE: DNA
<213> ORGANISM: Artificial
<220> FEATURE:
<223> OTHER INFORMATION: primer, based on Lactococcus lactis

<400> SEQUENCE: 135
aaaaaagatt aatagctaaa actattaatc ttatcccatc                          40

<210> SEQ ID NO 136
<211> LENGTH: 20
<212> TYPE: DNA
<213> ORGANISM: Artificial
<220> FEATURE:
<223> OTHER INFORMATION: primer, based on Lactococcus lactis

<400> SEQUENCE: 136
aggcagtttc tgaccctct                                                 20

<210> SEQ ID NO 137
<211> LENGTH: 40
<212> TYPE: DNA
<213> ORGANISM: Artificial
<220> FEATURE:
<223> OTHER INFORMATION: primer, based on Lactococcus lactis

<400> SEQUENCE: 137
gggttcagaa actgcctgat ggtaaatttg ttccaaatga                          40

<210> SEQ ID NO 138
<211> LENGTH: 40
<212> TYPE: DNA
<213> ORGANISM: Artificial
<220> FEATURE:
<223> OTHER INFORMATION: primer, based on Lactococcus lactis

<400> SEQUENCE: 138
agaaacaaat atttcaaaat cctactattt gatagtagga                          40

<210> SEQ ID NO 139
<211> LENGTH: 40
<212> TYPE: DNA
<213> ORGANISM: Artificial
<220> FEATURE:
<223> OTHER INFORMATION: primer, based on Lactococcus lactis

<400> SEQUENCE: 139
tttttaatat attagtccaa aagctcaaaa aggctgattt                          40

<210> SEQ ID NO 140
<211> LENGTH: 40
<212> TYPE: DNA
<213> ORGANISM: Artificial
<220> FEATURE:
<223> OTHER INFORMATION: primer, based on Lactococcus lactis

<400> SEQUENCE: 140
aaagcagatg agtagacttt tcaattattt tgtaaagcac                          40
```

<210> SEQ ID NO 141
<211> LENGTH: 40
<212> TYPE: DNA
<213> ORGANISM: Artificial
<220> FEATURE:
<223> OTHER INFORMATION: primer, based on Lactococcus lactis

<400> SEQUENCE: 141
tttcaaaaaa atagataacg cttgcattat gaaaatgaaa                                40

<210> SEQ ID NO 142
<211> LENGTH: 40
<212> TYPE: DNA
<213> ORGANISM: Artificial
<220> FEATURE:
<223> OTHER INFORMATION: primer, based on Lactococcus lactis

<400> SEQUENCE: 142
acgttataat tatttttata aagaacgtta aattataaaa                                40

<210> SEQ ID NO 143
<211> LENGTH: 40
<212> TYPE: DNA
<213> ORGANISM: Artificial
<220> FEATURE:
<223> OTHER INFORMATION: primer, based on Lactococcus lactis

<400> SEQUENCE: 143
cgttaagaat aaggagaaat aattatgaaa aaaaagatta                                40

<210> SEQ ID NO 144
<211> LENGTH: 20
<212> TYPE: DNA
<213> ORGANISM: Artificial
<220> FEATURE:
<223> OTHER INFORMATION: primer, based on Lactococcus lactis

<400> SEQUENCE: 144
tctcagctat tttaatgtct                                                      20

<210> SEQ ID NO 145
<211> LENGTH: 40
<212> TYPE: DNA
<213> ORGANISM: Artificial
<220> FEATURE:
<223> OTHER INFORMATION: primer, based on Lactococcus lactis

<400> SEQUENCE: 145
agacattaaa atagctgaga taatcttttt tttcataatt                                40

<210> SEQ ID NO 146
<211> LENGTH: 40
<212> TYPE: DNA
<213> ORGANISM: Artificial
<220> FEATURE:
<223> OTHER INFORMATION: primer, based on Lactococcus lactis

<400> SEQUENCE: 146
atttctcctt attcttaacg ttttataatt taacgttctt                                40

<210> SEQ ID NO 147
<211> LENGTH: 40
<212> TYPE: DNA
<213> ORGANISM: Artificial
<220> FEATURE:
<223> OTHER INFORMATION: primer, based on Lactococcus lactis

<400> SEQUENCE: 147
tataaaaata attataacgt tttcattttc ataatgcaag                    40

<210> SEQ ID NO 148
<211> LENGTH: 40
<212> TYPE: DNA
<213> ORGANISM: Artificial
<220> FEATURE:
<223> OTHER INFORMATION: primer, based on Lactococcus lactis

<400> SEQUENCE: 148
cgttatctat tttttgaaa gtgctttaca aaataattga                     40

<210> SEQ ID NO 149
<211> LENGTH: 40
<212> TYPE: DNA
<213> ORGANISM: Artificial
<220> FEATURE:
<223> OTHER INFORMATION: primer, based on Lactococcus lactis

<400> SEQUENCE: 149
aaagtctact catctgcttt aaatcagcct ttttgagctt                    40

<210> SEQ ID NO 150
<211> LENGTH: 40
<212> TYPE: DNA
<213> ORGANISM: Artificial
<220> FEATURE:
<223> OTHER INFORMATION: primer, based on Lactococcus lactis

<400> SEQUENCE: 150
ttggactaat atattaaaaa tcctactatc aaatagtagg                    40

<210> SEQ ID NO 151
<211> LENGTH: 40
<212> TYPE: DNA
<213> ORGANISM: Artificial
<220> FEATURE:
<223> OTHER INFORMATION: primer, based on Lactococcus lactis

<400> SEQUENCE: 151
attttgaaat atttgtttct tcatttggaa caaatttacc                    40

<210> SEQ ID NO 152
<211> LENGTH: 20
<212> TYPE: DNA
<213> ORGANISM: Artificial
<220> FEATURE:
<223> OTHER INFORMATION: primer, based on Lactococcus lactis

<400> SEQUENCE: 152
atcaggcagt ttctgaaccc                                          20

<210> SEQ ID NO 153
<211> LENGTH: 155
<212> TYPE: DNA
<213> ORGANISM: Lactococcus lactis

<400> SEQUENCE: 153
tggatatttt ttataaatct ggtttgaaca aattatattg acatctcttt ttctatcctg    60
ataattctga gaggttattt tgggaaatac tattgaacca tatcgaggtg gtgtggtata   120
atgaagggaa ttaaaaaaga taggaaaatt tcatg                             155

```
<210> SEQ ID NO 154
<211> LENGTH: 56
<212> TYPE: DNA
<213> ORGANISM: Lactococcus lactis

<400> SEQUENCE: 154
tccggacatt cattgagtgc atgatgcaca gtaaccatag aaaggaagac acaatg        56

<210> SEQ ID NO 155
<211> LENGTH: 22
<212> TYPE: DNA
<213> ORGANISM: Artificial
<220> FEATURE:
<223> OTHER INFORMATION: primer, based on Lactococcus lactis

<400> SEQUENCE: 155
tggatatttt ttataaatct gg                                             22

<210> SEQ ID NO 156
<211> LENGTH: 28
<212> TYPE: DNA
<213> ORGANISM: Artificial
<220> FEATURE:
<223> OTHER INFORMATION: primer, based on Lactococcus lactis

<400> SEQUENCE: 156
catgaaattt tcctatcttt tttaattc                                       28

<210> SEQ ID NO 157
<211> LENGTH: 268
<212> TYPE: DNA
<213> ORGANISM: Lactococcus lactis

<400> SEQUENCE: 157
gctagataag ccttgaaaat ttctacaata aatagtataa tagaaataat ggtttgtcag    60
caaaatctgt gggatatatt gtccccatag gctttgtaag caacgaaaca ctactgtttt   120
cgttgctttt ttggcgtctt ttatattgaa taaatcagaa aagttattaa aaagacaaac   180
tactgaattt tcggttttttt taattaaaaa ttcatcaaaa acacagactt ttttaatcaa   240
atctaaaaaa tagaggagaa aacacttg                                      268

<210> SEQ ID NO 158
<211> LENGTH: 327
<212> TYPE: DNA
<213> ORGANISM: Lactococcus lactis

<400> SEQUENCE: 158
gttcagaaac tgcctgatgg gatattatct ttatcctcct tatatataat cttttttaaat   60 agtattttca gaataacata ataacctgta acaaggtagg taattaagat gccaataaaa   120
gctcgttatt agtgcagttt ttgaaacaat ataaaatgac tacctaataa ctgtgatact   180
tatttgagta aaatattttg aagggaaatt tactgatgaa agtggttaag aaaagttact   240
ttaattcata tttattagta cttattgcac catgttgagt aactatgata caatagataa   300
atatactact tcaaggagaa gattatg                                       327

<210> SEQ ID NO 159
<211> LENGTH: 180
<212> TYPE: DNA
<213> ORGANISM: Lactococcus lactis

<400> SEQUENCE: 159
aaccgctttc agaagaaggg gagttcattt gcttttgtag agcgctttct aaggtagttt     60
```

```
atgtttgcaa attttaaaaa aagtgttaaa ataaaagagt aagttaaatt gttaacttag    120
tcaatttaaa aggtttgcct tttataaaat ctaatccta taaggaggaa actactaatg    180
```

<210> SEQ ID NO 160
<211> LENGTH: 167
<212> TYPE: DNA
<213> ORGANISM: Lactococcus lactis

<400> SEQUENCE: 160

```
tgtcagtaat tttttattgt ataaaatcat taaaaatgca aacgcttttt atttgtaatt     60
gaaataaaaa aataactaag tgaatcatgg ctgaaaaaca caaagaaat tgtaattgtg    120 ttataattta accgtatttc aaattcaagg aaggtttatt aaacatg                 167
```

<210> SEQ ID NO 161
<211> LENGTH: 127
<212> TYPE: DNA
<213> ORGANISM: Lactococcus lactis

<400> SEQUENCE: 161

```
ggagaaagga attgagttcg tccttctaaa cagtcaacga taatctgaca tcagattatt     60
gctgtccctg aagtctaagc actaaagtgc taagacccta gggcgggctc acatcttata    120
aataatg                                                             127
```

<210> SEQ ID NO 162
<211> LENGTH: 210
<212> TYPE: DNA
<213> ORGANISM: Lactococcus lactis

<400> SEQUENCE: 162

```
ctatcctctt tcttttcttt ttattcatag tatttatgaa aaccattttc atttacaaat     60
tatatcatga actgtaaacc ttttcaacct tcaagtgtgt ttttttacgt gattttcaa    120 taaaaatagc gtagaatgga tatatagtgt tttttatttt caggagaatt tagaaaactt    180
attttcatta atattggagg aaccattttg                                    210
```

<210> SEQ ID NO 163
<211> LENGTH: 160
<212> TYPE: DNA
<213> ORGANISM: Lactococcus lactis

<400> SEQUENCE: 163

```
gataagatta atagttttag ctattaatct ttttttattt ttatttaaga atggcttaat     60
aaagcggtta ctttggattt ttgtgagctt ggactagaaa aaaacttcac aaaatgctat    120
actaggtagg taaaaaaata ttcggaggaa ttttgaaatg                         160
```

<210> SEQ ID NO 164
<211> LENGTH: 433
<212> TYPE: DNA
<213> ORGANISM: Lactococcus lactis

<400> SEQUENCE: 164

```
tcaaaatata ggcttaatcg ctttttaaaa aaggattgaa agtaaaaaag gaatgccagt     60 tccttttta caactattct aaaaaataga ttgacaatca ctataaaaaa tgatattata    120
ttaaacggta cttttactt tggactctca ggagaacttg tataagttgc taaacttctt    180
gtcagaactt ggcttaagcg accatatact gactaaaaaa ttgataaaag aaattgagtt    240
cgatttccca tattctagga aaatagacaa atgtttccaa ggaacttcgt tcctctccaa    300
```

```
cattttctaa ttttctacga atataaacgg tcaatctcac atcttaatca tccaataaaa      360
agaaaggaat gcttttgtat ttctcatcgc ttcgcagaaa tgtggaaaaa tataaaaagc      420
agacagtaaa atg                                                        433
```

<210> SEQ ID NO 165
<211> LENGTH: 271
<212> TYPE: DNA
<213> ORGANISM: Lactococcus lactis

<400> SEQUENCE: 165

```
tttttgcgtt gggcttgcgt cgttagcttt tgctttacat acgtcagtac gcttcagcat       60
ggacttcgtc ctaaaagctg cctagcaatc ctttagcaaa aaatgttatc cgtaattggt      120
ggtttgattt aggtcaaatt gccagtattt tgtcaatgct aactttgtta gacagacaaa      180
aactccccgc ttgctgatta ttttattaat cagtaagaaa atcgatggca aaaactatcg      240
aaatttaaaa taatatagag gtagaattgt g                                    271
```

<210> SEQ ID NO 166
<211> LENGTH: 170
<212> TYPE: DNA
<213> ORGANISM: Lactococcus lactis

<400> SEQUENCE: 166

```
ctacaaacgc tttactgaaa acgctataag gtcattttac cactttataa taaaaaaaaa       60
aaaatatttc gcttaaaaaa tgatagaata gaattgaaat ttaaaataaa ggaggagata      120
ctgacaaggc tgacttttat cggctgagtt ttgtatcata tattttatg                 170
```

<210> SEQ ID NO 167
<211> LENGTH: 162
<212> TYPE: DNA
<213> ORGANISM: Lactococcus lactis

<400> SEQUENCE: 167

```
cagcattaag ataaagagtt atgagctaaa aataagcact tgtcaaactt ctgataatct       60
gttatactta tttagtatgt ttttgcatac taataaaact gttcatccgc tgagcttaat      120
ttgctaaaag ctgcttatga tgggcaagag gagaaaaaaa tg                        162
```

<210> SEQ ID NO 168
<211> LENGTH: 305
<212> TYPE: DNA
<213> ORGANISM: Lactococcus lactis

<400> SEQUENCE: 168

```
taaatcataa aacctctgtc agaggttttt tattttaaat atgaaaaatg aaagataaaa       60
tttactgaca gaaagtcaa caagcttaaa aataaaaaga acacccgaa agcattgcca       120 taggtactct tatcagataa tctgaaaata aaaatggact caggctagaa aaataaaggc      180
ttttatgaaa gaaagacttg catttgttgt tgaaaaatgc taaaatacat aagtccgact      240
ttttagatat atttaaattt gtatttatat ctttcgggaa attttaagg aggtactttt       300 gcttg                                                                 305
```

<210> SEQ ID NO 169
<211> LENGTH: 245
<212> TYPE: DNA
<213> ORGANISM: Lactococcus lactis

<400> SEQUENCE: 169

-continued

```
tttttcagta gatatagatt aataaaagat aaatagattt caaagtaagt ttatccttgc      60
atttctaaaa aaactttgat atacttattt atggttctaa aagaactgac cgaagacagt    120
aggggacgaa agtcataaac ttcctaccga ggacaaatat caaatgata attgaactct     180 ctatgtcttt tgtgtgtaga gattttttgt ttctacaacc aaaataaaat ggaggtaaaa    240
aaatg                                                                245

<210> SEQ ID NO 170
<211> LENGTH: 72
<212> TYPE: DNA
<213> ORGANISM: Lactococcus lactis

<400> SEQUENCE: 170
ttataagcaa catcacttat atcggcggat ttacgcaaca aactaaaaaa ttaataggag     60
aatattaaaa tg                                                         72

<210> SEQ ID NO 171
<211> LENGTH: 244
<212> TYPE: DNA
<213> ORGANISM: Lactococcus lactis

<400> SEQUENCE: 171
taaatttgtt ccaaatgaag aaacaaatat ttcaaaatcc tactatttga tagtaggatt     60
tttaatatat tagtccaaaa gctcaaaaag gctgatttaa agcagatgag tagacttttc    120
aattattttg taaagcactt tcaaaaaata gataacgctt gcattatgaa aatgaaaacg    180
ttataattat ttttataaag aacgttaaat tataaaacgt taagaataag gagaaataat    240
tatg                                                                  244

<210> SEQ ID NO 172
<211> LENGTH: 191
<212> TYPE: DNA
<213> ORGANISM: Lactococcus lactis

<400> SEQUENCE: 172
tcaggataga aaatttttct tcctttgtta aaaacttagt ggagaatttt tcaaactcaa     60
actgttaaac ttttgaaaac atgcaaaggt aattttaaaa cttgcttatt catgctcaaa    120
aagtataact gcagtttaaa gctaaatagc cttgaactag taaaaaattt ctagaaggga    180
gcatattttt g                                                          191

<210> SEQ ID NO 173
<211> LENGTH: 222
<212> TYPE: DNA
<213> ORGANISM: Lactococcus lactis

<400> SEQUENCE: 173
atgataaaag ttgctgacag agttgccagt gactttttt gattctgtca gcaaaagaa       60 aagataattt taaaattgtg aataagcgtg tggtttaatt gctagcctgt cagtaatttg    120
tgcaaactgc ccaaaagatt taggcactta tcttattgtt tttagaaaac gtttacagta    180
gaatataaac aaagaacaaa agttactaga ggagaaataa tg                       222

<210> SEQ ID NO 174
<211> LENGTH: 91
<212> TYPE: DNA
<213> ORGANISM: Lactococcus lactis

<400> SEQUENCE: 174
```

```
cttatttcac aagcataacc ttaggaaatt tctccaaaaa atgataaatt tctaattata    60
gacacataaa atagaaaggg aatctattat g                                  91

<210> SEQ ID NO 175
<211> LENGTH: 164
<212> TYPE: DNA
<213> ORGANISM: Lactococcus lactis

<400> SEQUENCE: 175
tttaataaaa aactgaaaaa atcacaggta aactcttgtt ttactgtgat tttatgttaa    60
aataattaat gagtgtaatt gtatataaaa ttatctgtac acttacctaa tttattgaaa   120
aaaatatgaa tcgtgatgtg tgagggaaag gagtcgcttt tatg                    164

<210> SEQ ID NO 176
<211> LENGTH: 201
<212> TYPE: DNA
<213> ORGANISM: Lactococcus lactis

<400> SEQUENCE: 176
aattcgctca cttaccgcac gaagtaattt taaactatca acgtttttag attacaacac    60
ttaatcattt cctttgtaa ggaatttaat aggttaattt ttactgacag ttctgtcagt    120
aaattttcgt acgtcaaatc tacttagaaa ggaactgaat tcagtgagta atttacttgc   180
tgaatcgtat ttaatcttat g                                             201

<210> SEQ ID NO 177
<211> LENGTH: 395
<212> TYPE: DNA
<213> ORGANISM: Lactococcus lactis

<400> SEQUENCE: 177
ttctctcctc acaaactatt ttatttacta taattatttt atcacaaaaa aagcgttttc    60
agcaaaaata ttaattttat tcttagaaaa aaatgtaaaa atctccctta tggggattat   120
ataggcaaaa atattcgtta aatttgtcag acaacattga gatataaaaa acagaataaa   180
aagaaagggg agtaggatag ctttcattta ctcatattga taaaagaaat aaatgaatag   240
atgcttgcaa aagtagctta acaatgtat aatgagagag ttgctatgca accatctcgc   300
atttcgtctc gacaaagtcg tagtgtacgc aagtattgcg gctgcggatg acagatgaaa   360
gaggaaaaac tattttaaaa ggagacatta acatg                              395

<210> SEQ ID NO 178
<211> LENGTH: 292
<212> TYPE: DNA
<213> ORGANISM: Lactococcus lactis

<400> SEQUENCE: 178
tatttttatt ttattataat catttcatca tttaattatc attttgctaa atgatatgat    60 gcatttttgaa gataataaaa tgctagtaat aagagctggc ctaatattct aaaattgtat   120
tatatatatc taaataataa aattaatctt aaaagtcatc taaaacaatc agtcaaaagt   180
tgataaagaa ttagggcttg acaagttcta aaataattga tagaataata gagttgaaaa   240
gcagaagcac ccgcttctcg ccttagaggt tatagccctg ggcaaacaaa tg            292

<210> SEQ ID NO 179
<211> LENGTH: 1313
<212> TYPE: DNA
<213> ORGANISM: Lactococcus lactis
```

<400> SEQUENCE: 179

```
aaatcctcct atataaatag tttataaaac ctttaatcaa attatatcaa aaagtttaaa        60
gatgacaaag tgtgggttct tgtcttttc agtaaattca ttgattttat ttaaaatttt       120
aaagatata caaaagaac aggaaagaat gaaaaaagt ctaaaaagtc cttgacaagg         180
cacatctcct tgatagaat agacaagtgc tgttaaaaac agtatgtagc gatgaaacga       240
gaggttgcga cacacccgaa ggtattgcca tacctaacgt gtcggttttc ccgtggagct      300
agcctattga atacaataga cgagaggaga aaaaatggca actaaaaaaa ttcgcattcg      360
cttgaaagca tacgaacatc gtatccttga cgcagctgca gaaaaaatcg tagaaactgc     420
taaacgtaca aacgcagaag taagtggtcc aattccactt ccaactgacc gtagcgtcta    480
cactgttatc cgcgcgactc acaaatataa agactcacgc gaacaattcg aaatgcgtac    540
acacaaacgc ttgatcgaca tcatcgaacc aacacaaaaa actgttgatt cacttatgaa    600
actcgatttg ccaagtggtg taaacatcga aattaaactc taattaagaa aggtaattct    660
catgtcaaaa ggaatcttag ggaaaaaagt gggaatgact caaatcttca cagacaacgg    720
tgaattaatt cctgttactg tgatcgaagc gactccaaac acagttcttc aagttaaatc    780
tgtcgaaaca gacggttacg aagcaactca agttggtttc gatacacttc gtgaagtttt    840
gaccaacaaa cctgccaaag gtcatgctgc taaagctaat acgactccta agcgcttcgt    900
tcgtgaattc aaaggactcg aaggcgctga agtaggagca gaaatcactg ttgatacatt    960
tgcagccgga gatgttgttg atgttaccgg aacttctaaa ggtaaaggtt ccaaggccc    1020
aatcaaacgt catggtcaat cacgtggtcc tatggcccac ggttcacgtt accaccgtcg   1080
tcctggttca atgggtcctg ttgcagctaa caaagttcca aaaggtaaaa aacttgctgg   1140
acgtatgggt aacaaacgcg ttactgtaca aaaccttgtt attgcacaag tgcttcctga   1200
aaagaacgtt atccttgtaa aaggtaatgt cccaggtgct aagaaatcat tgattgttgt   1260
taaatcagca atcaaagcta ataagaagg aaaggagata gaaatctata atg          1313
```

<210> SEQ ID NO 180
<211> LENGTH: 110
<212> TYPE: DNA
<213> ORGANISM: Lactococcus lactis

<400> SEQUENCE: 180

```
aaatctaaat gttttctctt gactaaatct gaccattgag ataaaataag aatatgttag     60
cactcaacta ttaagagtgc taaaaataaa aaatggagga agtataatg               110
```

<210> SEQ ID NO 181
<211> LENGTH: 33
<212> TYPE: PRT
<213> ORGANISM: Homo sapiens

<400> SEQUENCE: 181

His Ala Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp

<210> SEQ ID NO 182
<211> LENGTH: 33
<212> TYPE: PRT
<213> ORGANISM: Artificial

-continued

```
<220> FEATURE:
<223> OTHER INFORMATION: Amino acid, based on homo sapiens

<400> SEQUENCE: 182

His Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp

<210> SEQ ID NO 183
<211> LENGTH: 102
<212> TYPE: DNA
<213> ORGANISM: Artificial
<220> FEATURE:
<223> OTHER INFORMATION: based on homo sapiens

<400> SEQUENCE: 183
cacggtgatg gttcattttc agatgaaatg aacactatcc ttgataacct tgctgctcgt      60
gattttatca actggcttat ccaaactaaa atcactgatt aa                       102

<210> SEQ ID NO 184
<211> LENGTH: 27
<212> TYPE: PRT
<213> ORGANISM: Lactococcus lactis

<400> SEQUENCE: 184

Met Lys Lys Lys Ile Ile Ser Ala Ile Leu Met Ser Thr Val Ile Leu
1               5                   10                  15

Ser Ala Ala Ala Pro Leu Ser Gly Val Tyr Ala
            20                  25

<210> SEQ ID NO 185
<211> LENGTH: 30
<212> TYPE: PRT
<213> ORGANISM: Artificial
<220> FEATURE:
<223> OTHER INFORMATION: Amino acid, based on Lactococcus lactis

<400> SEQUENCE: 185

Met Lys Lys Asn Ile Ile Ser Ala Ile Leu Met Ser Thr Val Ile Leu
1               5                   10                  15

Ser Ala Ala Ala Pro Leu Ser Gly Val Tyr Ala Asp Thr Asn
            20                  25                  30
```